United States Patent
Archambault et al.

(10) Patent No.: US 9,028,828 B2
(45) Date of Patent: May 12, 2015

(54) P97 PROTEIN AND USES THEREOF AS VACCINE ADJUVANT

(71) Applicant: Transfert Plus, S.E.C., Montreal (CA)

(72) Inventors: Denis Archambault, Longueuil (CA); Elodie Roques, Montreal (CA)

(73) Assignees: Denis Archambault, Longueuil (CA); Elodie Roques, Montreal (CA)

( * ) Notice: Subject to any disclaimer, the term of this patent is extended or adjusted under 35 U.S.C. 154(b) by 0 days.

(21) Appl. No.: 13/872,503

(22) Filed: Apr. 29, 2013

(65) Prior Publication Data

US 2013/0287816 A1    Oct. 31, 2013

Related U.S. Application Data

(60) Provisional application No. 61/639,127, filed on Apr. 27, 2012.

(51) Int. Cl.
*C07K 14/30* (2006.01)
*C07K 14/00* (2006.01)

(52) U.S. Cl.
CPC ............... *C07K 14/001* (2013.01); *C07K 14/30* (2013.01)

(58) Field of Classification Search
None
See application file for complete search history.

(56) References Cited

PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Adams et al.—In Vivo expression analysis of the P97 and P102 paralog families of mycoplasma hyopneumoniae. Infection and Immunity, Nov. 2005, vol. 73, No. 11, pp. 7784-7787.
Ahn et al.—Identification of Interleukin-1, tumor necrosis factor-α, and Interleukin-6 expression in lungs from pigs naturally infected with mycoplasma hyopneumoniae by in situ hybridization. J. Vet. Med. Sci. 71(4): 441-445, 2009.
Bandrick et al.—Passive transfer of maternal mycoplasma hyopneumoniae-specific cellular immunity to piglets. Clinical and Vaccine Immunology, Mar. 2008, vol. 15, No. 3, pp. 540-543.
Burnett et al.—P159 is a proteolytically processed, surface adhesin of mycoplasma hyopneumoniae: defined domains of P159 bind heparin and promote adherence to eukaryote cells. Molecular Microbiology (2006) 60(3), 669-686.
Chen et al.—Identification of a novel adhesin-like glycoprotein from mycoplasma hyopneumoniae. Veterinay Microbiology 62 (1998) 97-110.
Chen et al.—A recombinant chimera composed of repeat region RR1 of mycoplasma hyopneumoniae adhesin with pseudomonas exotoxin: in vivo evaluation of specific IgG response in mice and pigs. Veterinary Microbiology 80 (2001) 347-357.
Chen et al.—Evaluation of the immunogenicity of the P97R1 adhesin of mycoplasma hyopneumoniae as a mucosal vaccine in mice. Journal of Medical Microbiology (2006), 55, 923-929.
Chen et al.—Evaluation of immune response to recombinant potential protective antigens of mycoplasma hyopneumoniae delivered as cocktail DNA and/or recombinant protein vaccines in mice. Vaccine 26 (2008) 4372-4378.
Choi et al.—Expression of inflammatory cytokines in pigs experimentally infected with mycoplasma hyopneumoniae. J. Comp. Path. 2006, vol. 134, 40-46.
Conceiçao et al.—A recombinant chimera composed of R1 repaeat region of mycoplasma hyopneumoniae P97 adhesin with *Escherichia coli* heat-labile enterotoxin B subunit elicits immune response in mice. Vaccine 24 (2006) 5734-5743.
Damte et al.—Inflammatory responses to Mycoplasma hyopneumoniae in murine alveolar macrophage cell lines. New Zealand Veterinary Journal 2011;59(4):185-190.
Djordjevic et al.—Proteolytic processing of the Mycoplasma hyopneumoniae cilium adhesin. Infect Immun 2004;72 (5):2791-2802.
Feng et al.—Immune response to the attenuated mycoplasma hyopneumoniae 168 strain vaccine by intrapulmonic immunixation in piglets. Agricultural Sciences in China 2010, 9(3): 423-431.
Hsu et al.—Cloning and functional analysis of the P97 swine cilium adhesin gene of Mycoplasma hyopneumoniae. J Bacteriol 1997;179(4):1317-23.
Hsu et al.—Identification of the cilium binding epitope of the Mycoplasma hyopneumoniae P97 adhesin. Infect Immun 1998;66(10):4762-4766.
Hwang et al.—Surfacin C inhibits mycoplasma hyopnemoniae-induced transcription of proinflammatory cytokines and nitric oxide in murine de production RAW 264.7 cells. Biotechnol Lett (2008) 30:229-233.
Hwang et al.—Mycoplasma hyopneumoniae induces pro-inflammatory cytokine and nitric oxide production through NFkappaB and MAPK pathways in RAW264.7 cells. Vet Res Commun 2011;35(1):21-34.
Jenkins et al.—Two domains within the mycoplasma hyopneumoniae cilium adhesin bind herapin. Infection and Immunity, Jan. 2006, vol. 74, No. 1, pp. 481-487.
Maes et al.—Control of mycoplasma hyopneumoniae infections in pigs. Veterinary Microbiology 126 (2008) 297-309.
Minion et al.—R1 region of P97 mediates adherence of mycoplasma hyopneumonia to Swine Cilia. Infection and Immunity, May 2000, vol. 68, No. 5, pp. 3056-3060.
Minion, F. Chris—Molecular pathogenesis of mycoplasma anmial respiratory pathogens. Frontiers in Bioscience 7, d1410-1422, Jun. 1, 2002.

(Continued)

*Primary Examiner* — Brian J Gangle
(74) *Attorney, Agent, or Firm* — Goudreau Gage Dubuc; Alain Dumont

(57) ABSTRACT

Immunogenic compositions comprising a p97 adhesin adjuvant polypeptide, or a nucleic acid encoding said p97 adhesin adjuvant polypeptide, and a heterologous antigen are disclosed. Uses of the p97 adhesin adjuvant polypeptide or nucleic acid, or immunogenic compositions comprising same, for inducing an immune response against a heterologous antigen in a subject are also disclosed.

12 Claims, 23 Drawing Sheets

(56) References Cited

PUBLICATIONS

Minion et al.—The genome sequence of Mycoplasma hyopneumoniae strain 232, the agent of swine mycoplasmosis. J Bacteriol 2004;186(21):7123-7133.

Muneta et al.—Immune response of gnotobiotic piglets agains mycoplasma hyopneumoniae. J. Vet. Med. Sci. 70 (10): 1065-1071, 2008.

Ogawa et al.—Oral vaccination against mycoplasma pneumonia of swine using a live erysipelothrix rhusiopathiae vaccine strain as a vector. Vaccine 27 (2009) 4543-4550.

Okamba et al.—Immune responses induced by replication-defective adenovirus expressing the C-terminal portion of the Mycoplasma hyopneumoniae P97 adhesin. Clin Vaccine Immunol 2007;14(6):767-774.

Okamba et al.—Potential use of a recombinant replication-defective adenovirus vector carrying the C-terminal portion of the P97 adhesin protein as a vaccine against mycoplasma hyopneumoniae in swine. Vaccine 28 (2010) 4802-4809.

Opriessnig et al.—Experimental reproduction of postweaning multisystemic wasting syndrome in pigs by dual infection with Mycoplasma hyopneumoniae and porcine circovirus type 2. Vet Pathol 2004;41(6):624-40.

Razin et al.—Molecular biology and pathogenicity of mycoplasmas. Microbiology and Molecular Biology Reviews, Dec. 1998, vol. 62, No. 4, pp. 1094-1156.

Shimoji et al.—Vaccine efficacy of the attenuated erysipelothrix rhusiopathiae YS-19 expressing a recombinant protein of mycoplasma hyopneumoniae P97 adhesin against mycoplasmal pneumonia of swine. Vaccine 21 (2003) 532-537.

Sibila et al.—Chronological study of mycoplasma hyopneumoniae infection, seroconversion and associated lung lesions in vaccinated and non-vaccinated pigs. Veterinary Microbiology 122 (2007) 97-107.

Sibila et al.—Curretn perspectives on the diagnosis and epidemiology of mycoplasma hyopneumoniae infection. The Veterinary Journal 181 (2009) 221-231.

Thacker et al.—Mycoplasma hyopneumoniae potentiation of porcine reproductive and respiratory syndrome virus-induced pneumonia. J Clin Microbiol 1999;37(3):620-627.

Thacker et al.—Effect of vaccination on the potentiation of porcine reproductive and respiratory syndrome virus (PRRSV)-induced pneumonia by mycoplasma hyopneumoniae. Vaccine 18 (2000) 1244-1252.

Wallgren et al.—Humoral immune responses to mycoplasma hyopneumoniae in sows and offspring following an outbreak of mycoplasmosis. Veterinary Microbiology 60 (1998) 193-205.

Wilton et al.—Reiterated repeat region variablility in the ciliary adhesin gene of mycoplasma hyopneumoniae. Microbiology (1998), 144, 1931-1943.

\* cited by examiner

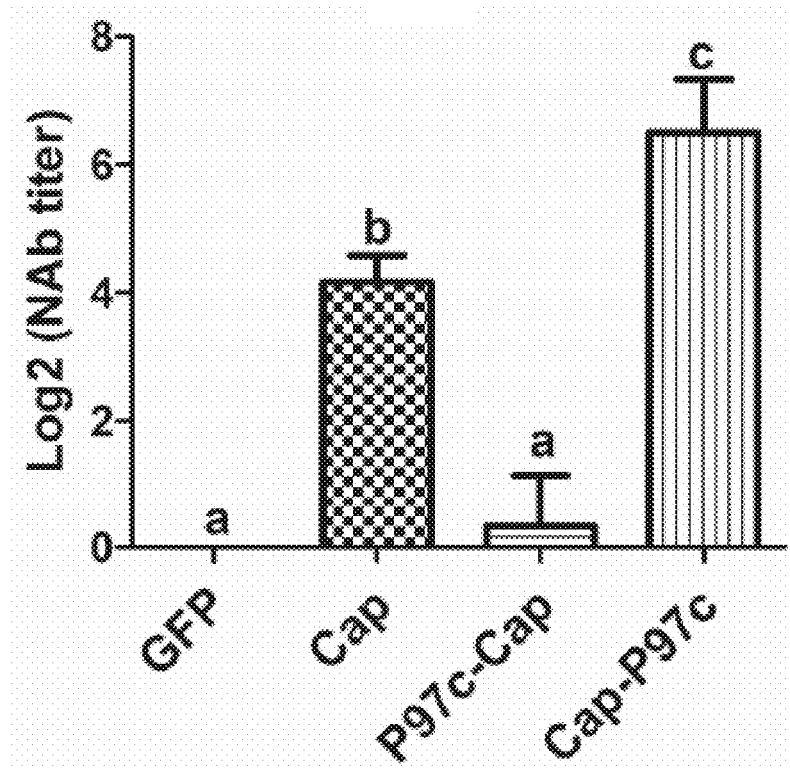

FIG. 5

```
   1 mskksktfki gltagivglg vfgltvglss lakyrsespr kiandfaakv stlafspyaf
  61 etdsdykivk rwlvdsnnni rnkekvidsf sfftkngdql ekinfqdpey tkakitfeil
 121 eiipddvnqn fkvkfqalqk lhngdiaksd iyeqtvafak qsnllvaefn fslkkitekl
 181 nqqienlstk itnfadekts sqkdpstlra idfqydlnta rnpedldikl anyfpviknl
 241 inrlnnapen klpnnlgnif efsfakdsst nqyvsiqnqi pslflkadls qsareilasp
 301 devqpvinil rlmkkdnssy flnfedfvnn ltlknmqked lnakgqnlsa yefladiksg
 361 ffpgdkrssh tkaeisnlln kkeniydfgk yngkfndrln spnleyslda asasldkkdk
 421 sivlipyrle ikdkffaddl ypdtkdnilv kegilkltgf kkgskidlpn inqqifktey
 481 lpffekgkee qakldygnil npyntqlakv evealfkgnk nqeiyqaldg nyayefgafk
 541 svinswtgki qhpekadiqr ftrhleqvki gsnsvlnqpq ttkeqvissl ksnnffkngh
 601 qvasyfqdll tkdkltilet lydlakkwgl etnraqfpkg vfqytkdifa eadklkfiel
 661 kkkdpynqik eihqlsfnil arndviksdg fygvlllpqs vktelegkne aqifealkky
 721 sliensafkt tildknlleg tdfktfgdfl kafflkaaqf nnfapwakld dnlqysfeai
 781 kkgettkegk reevdkkvke ldnkikgilp qppaakpeaa kpvaakpett kpvaakpeaa
 841 kpeaakpvaa kpeaakpvaa kpeaakpvaa kpeaakpvaa kpeaakpvat ntgfsltnkp
 901 kedyfpmafs ykleytdenk lslktpeinv flelvhqsey eeqeiikeld ktvlnlqyqf
 961 qevkvtsdqy qklshpmmte qssnqgkkse gtpnqgkkae gapnqgkkae gtpnqgkkae
1021 gapsqqsptt eltnylpdlg kkideiikkq gknwktevel iedniagdak llyfilrdds
1081 ksgdpkkssl kvkitvkqsn nnqepesk
```

FIG. 6A

```
   1 maknnknsll vtataivgva vfattvglvt rirykgenpr aeleslvskv qnvafksdvf
  61 dnsttykqik allfdetqkl rpgidlnkfi sfytavnski qkfevsfapn kpffefinli
 121 pddknqtftl qfrakhqldn nytayssils kkiayaqrsq faladfnanh rkitksfqtn
 181 iqnlretdfs vdfsssqtsl asqkipfltr vedfaadink sgnqeeaisr iskyfpdfqr
 241 yihelkddpn nvlpfkkgki fdfsitrrag tndfislsan sepsflikar ltneakfelr
 301 glnieeaeml eeiklvpvdq fvvnletdlk pgqapeksqk pqseqteikk tyfaeidkil
 361 skitmrklql sdfkvapqts ssqpkvkas vsawsnldqg qenrilvpvs qqssnpqqhq
 421 qqqpqpqsqp qpqpqsqpqs qpqpnaqtqp kaqaqsspka pvqkpatpdp sksfkirtkr
 481 ardflkefnk tfyrsnklks qkleekinse ylsnkigidl gvlkkyinnn qgieytfdia
 541 nakirdaqdg itshieipvt islwssffgd sdnvllkskt etfiipyfqk ettseskdqk
 601 vqhtqkeldl nqkliyqlse lpgtsaqgss gssaqteqik evklptltaf iskqeleali
 661 dgdknlasqp tsqavsvsqe vkttefqqqe anstnsspss pspsptspsp aspssspspt
 721 spknldenig vpnprfeeik kiisseftyk ynfraneall dawvgkqnfp slkdisqfrs
 781 dqrlakdykl vnlksnkflk edydvlafya nlvqkdprev lqylfeiaka nnligpeekl
 841 dlnqieddgi frrakaikli dkssnnqgiy gfsfnnqflk fhergwmstl ylpneaktkl
 901 adyqnllsag isdtkifsel nkiqpldlni kvqssdssds ksdssdssda kttstkqdll
 961 skltslksqi eaivkkyete sknylqtenn nssssssgteq kgssipeenk kfilentakl
1021 dnladlllaf yyqakrlnfa swsqlqdedl dyqiqfekea nntessssss sssssssssss
1081 sssssetdtn kpenaveykl tyyykiynkt tkkvvyttpk tiiklylass nigvkekqer
1141 elmnklvlsi psaysifylk qseweqvktn ngqqmgqtgs sqgfeslepf kkiqeivhkn
1201 nkdydlkvvt irddayaena kivhlrvvrk eeqqaeqkek ekekekekeq ketssqgqvp
1261 qsafffqvrl ikddyqgaea snqqtsrqam qmpnmesqns gssssapaaa aaakaar
```

FIG. 6B

```
   1 mklaklllkp fwlittiagi slslsaavgt vvginsynks yysylnqips qlkvaknaki
  61 sqekfdsivl nlkikdnfkk wsaktvltaa ksdlyrynlv safdlselin ndylvsfdle
 121 navvdqnsik nvviyaksdk dqityskqiv lkgfgnteqa rtnfdfsqid ssksfvdlsr
 181 anltlmefqi llaqnfener gsnwfsrler alvaskasls lynslgepvf lgpdyqldpv
 241 ldrkklltll nkdgklvlgl nlvqistkkt mnlnlevrga isnqeiskil kswletnlqg
 301 klktkddlqm alvkdkisls dywgspnsk vntsqiltks kefkdlfdls etnfflntki
 361 gtvylsiipk lldpsqisvv dkkklvenqk irfeitaslk rkaidkkfii qdlpvfvdlk
 421 vdfnkyqaav aqmfgtikav kefsmpedqd aktlssneik qrvdrlfela ktvtnlenps
 481 eevlksiyll ntgkylvdqd qekvkqelkt vieglkskan tqkteknspt qpkkpevsla
 541 kttensaktv kvstfaeeak gqsqsqqtqp vstsspqtsq nslpnstsss nsvlenekfg
 601 tsiwtafnfa niynlentks eyeistlgnk lffdfklvdk tnqnlilaqs kislnniins
 661 nksaydiikk fnpdvfldqt inyqngkdk kefilkdlsd nklifkseda iqtdqglelk
 721 kplklqskss npekeistsl ytgaiylvfd aknisdgnwi nlladrkgkg lvikvqnsnn
 781 nvpktkeive ngtylyeila gkdsikvnsy ffptkypkrv krlkfeinpk dtlpnffttle
 841 wfhldwyqig pgeqnkkpqq nakkeptiil ktlaifndks faekgsltkr selinglirn
 901 yvkk
```

FIG. 6C

```
   1 mskltksktf kiglvgsiig lgvfgltvgl sslakyrseh prkvvndfat kvstlsfspd
  61 affansdywt iknhlldskn qiknsekvlk sfsffskngd qlekinledp eyknagisfh
 121 ileiipddvn qnfkvkfqlw qkfangdiak sdiyqeesva fikqsnllva efnfslkkit
 181 dklnqqvgnl slkstnfadd lakitkptss yknpasfrvl dfqedlnqar nseelvkkla
 241 iyfpsldnli tklnessenk lpgnsghife fslrksqatn qyvsvqnqip flfleadlsq
 301 sardligqdf nfrpivssik lqkqdnssyf ldfnqflgnl klkdisktdf neqglktsay
 361 eilstirsgf fdnndlrsdq akesinkilk nkikfdfgkl daifsdkgns eslqyyldvk
 421 kasldktdks tilipfrlkv desffktstn lpeniiarkd gifkltgfdq glnnqlpkin
 481 qeiyktkyls ffekgkenqd lvdfgsepin gplliskvea dalfkenkpe aihkvletny
 541 nyqfnpyqsl ldswtgnlvq pklenikaln enekaavsea giaeilsrdf fldghqvasf
 601 yqdlltkdrl tvietlyelg kkwglhtnta nfprwkfrna knifeeatqy kfllgkkgke
 661 nfrkitkltf nglyrnekgq gfyatlvipk eikdklankt daevfaelkk hslidssgfk
 721 tinidknlle gedfenfgdl lkafflkaaq fnnfapwakl ddnlkysfvp kkgdqekegk
 781 kaeidkkvke ltdkisspgs vlpkseagkp vaakpeaakp sssttssvss aslegnylpi
 841 sfefklsyrd gakseiktpe ikvflelqtd kdyqenkiik eldktvleiq sefkewride
 901 safssltfpk sqksegtqnq gkkaegapnq skkseensnk lteyiqelgt kvekslkskg
 961 knysaeveki ieafsggykf ldfalveqtp kpetpkteaa kpettkpvaa rpeaakvaak
1021 psaakpvssp apkkstlyvr vlirkkenkq vk
```

FIG. 6D

```
   1 mkkqirnkai ivlaglsfig itagvglavq nsalrssyln qfkndksate llspindtel
  61 skiisnfslk enwskisagq afelhknply afkltdaidf skidkkfahl ffnvqvndnt
 121 kvegnsirnl tvfvfdaitk kevatrafht slsgfssvak edfienfvae sstyeldkdq
 181 lkknfateiv lpsafsikfq dvllthlrkt spesfqetkt iqvraltnsi tefqqqqqeg
 241 gsggsgtsgg ssggsssgst dqkgqtsqss ekesksekek gkdqqstqgs eqkqdqkqqk
 301 pkeaekpaqe kpaqekpaet pkvkapviep vkklvfenek lnqalletik dfgglkllaa
 361 sgiqgllpne ytllpvssdk slikldiddq agtasihlkl ldknkkeknl ilpinglasi
 421 gaikdkvfsq ifrnqnaylt irpqineylr knprkkiqev iwsfsrekfd qlrggnevek
 481 fleelynptq tsqspqksks sdsaknnvat iqaspetapk ttttnsntqs sststnnqss
 541 ngsqqmaspq tesslstakt seasnssees ssetkgtkeq ansetnpmgk sqakpeakpe
 601 ekqinledqa ktelkeilki hgwnyrtllk dqnqkvilpd ninfwfdlrn krssyenykl
 661 efdlvkktgq iqagdvidan kirlnlkisp lanlklevds knkqyidagq igdyvefdkq
 721 gkklveqgks ldlkvgasaa nsifspeiry sayelkgwty pididikgnp iqqeleklvg
 781 nfhkvginkn nqyqiystdi dkifaqakld kyfelsqeek qaskkylqek lnpiseitiv
 841 klppkeevlp pleeekkpeq dqkaqekqed kqnqkqqekq edkkeqdqqk hsqspdqkte
 901 tqthdqekdk qtssetspsn tnessgtqnt aqnsqtnqan sgqgqsqqaa ssstsyqthk
 961 ittfqddqkd qtneqtekei epeklafgdy lvkyldifet fkvgpdqkls igrwynapqr
1021 tynvifrvld keniqvaasl fqlhgisatn ialeksirya pdifidgtsg leykqdtgdk
1081 pylqgrqfvs ainsinntks syrvhklfdn lplseessqg lrlkssslvyd yqkndpytfq
1141 askealrkta ltkgvlylaf kpeqilgikg sktapgrnyk llsttnvhfk slyglsnlel
1201 vktkyqenlk lvwkliqakp vnddkilppq vadlprhrst eiilledskp gassspqtke
1261 nsqnkeaetf nldirqtkpn qieplehylg qtwlmeirid desatitiip eqqeredskl
1321 kvwkseikik dknkyqnqdt nwetelasvl grgfdygqig dttpqasnpq drvgmtfkgf
1381 avfkgdklln dkarlnvrka fmdqyfknys
```

FIG. 6E

```
   1 mknkkstlll ataaaiigst vfgtvvglas kvkyrgvnpt qgvisqlgli dsvafkpsia
  61 nftsdyqsvk kallngktfd pksseftdfv skfdfltnng rtvleipkky qvvisefspe
 121 ddkerfrlgf hikekledgn iaqsatkfiy llpldmpkaa lgqysyivdk nfnnliihpl
 181 snfsaqsikp laltrssdfi aklnqfknqd elwvylekff dlealkanir lqtadfsfek
 241 gnlvdpfvys firnpqngke wasdlnqdqk tvrlylrtef spqaktilkd ykykdetfls
 301 sidlkasngt slfanendlk dqldvdlldv sdyfggqset itsnsqvkpv paserslkdr
 361 vkfkkdqqkp riekfslyey dalsfysqlq elvskpnsik dlvnatlarn lrfslgkynf
 421 lfddlashld ytflvskaki kqssitkklf ielpikislk ssilgdqepn iktlfekevt
 481 fkldnfrdve iekafgllyp gvneeleqar reqrasleke kakkglkefs qqkdenlkai
 541 nnqdgleedd niterlpens piqyqqekaq lgsspdkpym ikdvqnqryy laksqiqeli
 601 kakdytklak llsnrhtyni slrlkeqlfe vnpripssrd ienakfvldk teknkywqiy
 661 ssaspafqnk wslfgyyryl lgldpkqtih elvklgqkaq lqfegyenlp sdfnledlkn
 721 iriktplfsq kdnfklslld fnnyydgeik apefglplfl pkelrknssn igssqnsnsp
 781 weqeiisqfk dqnlsnqdql aqfstkiwek iigdenefdq nnrlqykllk dlqeswinkt
 841 rdnlywtylg dklkvkpknn ldakfrqisn lqelltafyt saalsnnwny yqdsgaksti
 901 ifeeiaeldp kvkekvgadv yqlkfhyaig fddnagkfnq evirsssrti ylktsgkskl
 961 eadtidqlnq avenaplglq sfyldterfg vfqklatsla vqhkqkekpl pkklnndgyt
1021 lihdklkkpv ipqissspek dwfegklnqn gqsqnvnvst fgsiiespyf stnfqeeadl
1081 dqegqddskq gnksldnqea glikqklail lgnqfiqyyq qndkeiefei invekvsels
1141 frvefklakt ledngktirv lsdetmsliv nttiekapem saapevfdtk wveqydprtp
1201 laaktkfvlk fkdqipvdas gnisdkwlas iplvihqqml rlspvvktir elglkteqgq
1261 qqqqqqkka vrkeeelety npkdefniln pltkahrltl snlvnndpny kiedlkvikn
1321 eagdhqlefs lrannikrlm ntpitfadyn pffyfnedwr nidkylnnkg nvssqqqqqq
1381 qqqpgggnqg sgliqrlnkn ikpetftpal ialkrdnntn lsnysdkiim ikpkylvers
1441 igvpwstqld gyiqseqlkg qtssngqkrf kqdfiqalgl knteyhgklg lsirifdpgn
1501 elakikdasn kkgeekllks ydlfknylne yekkspkiak gwtnihpdqk eypnpnqklp
1561 enylnlvlnq pwkvtlynss dfitnlfvep egsdrgsqak lkqviqkqvn nnyadwgsay
1621 ltfwydkdii tnqpnvitan iadvfikdvk eledntklia pnitqwwpni sgskekfykp
1681 tvffgnwene nsnmnsqgqt ptwekiregf alqalkssfd qktrtfvltt naplplwkyg
1741 plgfqngpnf ktqdwrlvfq nddnqiaalr vqeqdrpeks sedkdkqkwi kfkvvipeem
1801 fnsgnirfvg vmqiqgpntl wlpvinssvi ydfyrgtgds ndvanlnvap wqvktiaftn
1861 nafnnvfkef niskkive
```

FIG. 6F

```
MSKKSKTFKIGLTAGIVGLGVFGLTVGLSSLAKYRSESPRKIAN
DFAAKVSTLAFSPYAFETDSDYKIVKRWLVDSNNNIRNKEKVIDSFSFFTKNGDQLEK
NFQDPEYTKAKITFEILEIIPDDVNQNFKVKFQALQKLHNGDIAKSDIYEQTVAFAK
QSNLLVAEFNFSLKKITEKLNQQIENLSTKITNFADEKTSSQKDPSTLRAIDFQYDLN
TARNAEDLDIKLANYFPVLKNLINRLNNAPENKLPNNLGNIFEFSFAKDSSTNQYVSI
QNQIPSLFLKADLSQSAREILASPDEVQPVINILRLMKKDNSSYFLNFEDFVNNLTLK
NMQKEDLNAKGQNLSAYEFLADIKSGFFPGDKRSSHTKAEISNLLNKKENIYDFGKYN
GKFNDRLNSPNLEYSLDAASASLDKKDKSIILIPYRLEIKDKFFADDLYPDTKDNILV
KEGILKLTGFKKGPKIDLPNINQQIFKTEYLPFFEKGKEEQAKLDYGNILNPYNTQLA
KVEVEALFKGNKNQEIYQALDGNYAYEFGAFKSVLNSWTGKIQHPEKADIQRFTRHLE
QVKLGSNSVLNQPQTTKEQVISSLKSNNFFKNGHQVASYFQDLLTKDKLTVLETLYDL
AKKWGLETNRAQFPKEVFQYTKDIFAEADKLKFLEGKKKDPYNQIKEIHQLSFNILAR
NDVIKSDGFYGVLLLPQSVKTELEGKNEAQIFEALKKYSLIENSAFKTTILDKNLLEG
TDFKTFGDFLKAFFLKAAQFNNFAPWAKLDDNLQYSFEAIKKGETTKEGKREEVDKKV
KELDNKIKGILPQPPAAKPEAAKPVAAKPEAAKPETTKPVAAKPEAAKPVAAKPVAAK
PVATNTNTNTGFSLTNKPKEDYFPMAFSYKLEYTDENKLSLKTPEINVFLELVHQSEY
EEQKIIKELDKTVLNLQYQFQEVKVTSEQYQKLSHPMMTEGSPNQGKKAEGAPNQGKK
AEGAPSQGKKAEGAPNQGKKAEGAPSQGKKAEGASNQQSTTTELTNYLPELGKKIDEI
IKKQGKNWKTEVELIEDNIAGDAKLLYFVLRDDSKSGDPKKSSLKVKITVKQSNNNQE
LKSK
```

FIG. 6G

```
                        at gagtaaaaaa tcaaaaacat ttaaaattgg tttgactgcc
ggaattgttg gtcttggagt ttttggtcta actgtcggac ttagcagctt ggcaaaatac
agatcagaaa gtccacgaaa gattgcaaat gattttgccg caaaagtttc aacattagct
tttagtcctt atgcttttga gactgattct gattataaaa tagtcaaaag gtgactagtt
gattctaata acaatattag aaataaagaa aaagttattg attcctttc ctttttact
aaaaacggtg atcagttaga aaaaattaat tttcaagatc ctgaatatac caaggcgaag
ataactttg agattcttga aattatccct gatgatgtca atcaaaattt taaggtaaaa
tttcaggcat tacaaaaact tcataatggt gatattgcca aatctgatat ttatgagcaa
acagttgctt ttgccaaaca gtcaaatctt ttagttgccg aatttaattt ttcgcttaaa
aaaattaccg aaaaattaaa tcaacaaatt gaaaatttat caacaaaaat tacaaatttt
gctgatgaaa aaacaagcag ccaaaaagat ccctcaactc taagagctat tgacttccaa
tacgatttaa atacagcgcg aaatcctgag gatttagata taagcttgc taattatttt
ccagtactta aaaatttaat aaacagacta ataatgctc ctgagaataa attacctaat
aatttgggta atattttga atttagcttt gcaaaagata gttcaactaa tcaatatgta
agtatccaga accaaattcc ttcgctgttt ttaaaagcag atcttagtca aagtgcccgt
gaaattttag ctagcccaga tgaagttcag ccagttatta acattttaag attaatgaaa
aaagataatt cttcttattt tctaaatttt gaggattttg ttaataattt aacactgaaa
aatatgcaaa aagaagattt aaatgcaaag ggtcaaaatc tttctgccta tgaatttcta
gcagatatta aatctggatt tttccctgga gacaagagat ccagtcatac caaggcagaa
attagtaatc ttttaaataa aaaagaaaat atttatgact ttggtaaata caatggaaaa
ttcaacgacc gtcttaactc gccaaattta gaatatagcc tagatgcagc aagcgcaagt
cttgataaaa aagataaatc aatagtttta attccctacc gccttgaaat taaagataaa
ttttttgccg atgatttata tccagataca aaagataata ttctcgtaaa agaagggatt
cttaaattaa ctggatttaa aaaaggctca aaaattgatc tccctaatat caatcagcaa
atttttaaaa ccgaatattt accattttt gaaaaaggta aagaagaaca agcaaaatta
gactatggta atatcttaaa tccatataat actcaacttg ccaaagttga agttgaagct
ctttttaaag ggaataaaaa ccaagaaatc tatcaagcac ttgatggaaa ttatgcctat
gaattcgggg cctttaaatc cgtgcttaat tcctgaacag gaaaaattca gcatcctgaa
aaagctgata tccaaagatt tacaagacat ttagaacaag ttaaaattgg ttctaattca
gttttaaatc aaccacaaac aacaaaagaa caagtaattt caagtcttaa aagtaataac
ttttttaaaa atggacatca agttgcaagt tatttccagg atttactcac caaggacaaa
ttaacaattt tagagactct ttatgatcta gcaaaaaaat ggggactaga aactaacaga
gcacaattcc caaaaggggt tttccaatat acaaaagata tttttgcaga agcagataaa
ttaaaatttt tggaattgaa gaaaaaggat ccttacaatc agataaaaga aattcaccaa
ctttccttta atatttagc ccgtaacgat gtaataaaat ctgatggatt ttacggagtt
ttattattgc cccaaagtgt aaaaactgaa ttagaaggca aaaatgaggc gcaaattttt
gaagcgctta aaaagtattc tttaattgag aactcggctt taaaactac tattttagat
aaaaatttac ttgaagggac tgattttaaa accttcggtg attttttaaa agcatttttc
cttaaagcag cccaatttaa taattttgct ccttgagcaa aattagacga taatcttcag
tattcatttg aagctatcaa aaaaggggaa actacaaaag aaggtaaaag agaagaagta
gataaaaaag ttaaggaatt ggataataaa ataaaaggta tattgcctca gccccagca
gcaaaaccag aagcagcaaa accagtagcg gctaaaccag aaacaacaaa accagtagca
gctaaacctg aagcagctaa acctgaagca gcaaaaccag tagcggctaa accagaagca
gcaaaaccag tagcggctaa accagaagca gcaaaaccag tagcggctaa accagaagca
gcaaaaccag tagcggctaa accagaagca gcaaaaccag ttgctactaa tactggcttt
tcacttacaa ataaaccaaa agaagactat ttcccaatgg cttttagtta taaattagaa
tatactgacg aaaataaatt aagcctaaaa acaccggaaa ttaatgtatt tttagaacta
gttcatcaaa gcgagtatga agaacaagaa ataataaagg aactagataa aactgtttta
aatcttcaat atcaattcca ggaagtcaag gtaactagtg accaatatca gaaacttagc
cacccaatga tgaccgaagg atcttcaaat caaggtaaaa aaagcgaagg aactcctaac
caaggtaaaa aagcagaagg cgcgcctaac caaggtaaaa aagccgaagg aactcctaac
caagggaaaa aagcagaggg agcacctagt caacaaagcc caactaccga attaactaat
taccttcctg acttaggtaa aaaaattgac gaaatcatta aaaacaaggg taaaaattga
aaaacagagg ttgaactaat cgaggataat atcgctggag atgctaaatt gctatacttt
atcctaaggg atgattcaaa atccggtgat cctaaaaaat caagtctaaa agttaaaata
acagtaaaac aaagtaataa taatcaggaa ccagaatcta aataa
```

FIG. 7A

```
   1 atggctaaga ataataagaa ttcattatta gtaacagcaa cagccattgt cggagttgca
  61 gtatttgcaa caacagttgg gcttgtaacg cgaattcgtt ataaaggtga aaatccccgc
 121 gctgaacttg aaagttaagt ttcaaaagtt caaaatgttg cctttaaatc cgatgtcttt
 181 gataattcaa ctacatataa acaaataaaa gcattacttt tcgatgaaac aggaaaatta
 241 agacccggaa ttgatcttaa taaatttatc tcttttata cagcggtaaa ttcaaaaatt
 301 caaaaatttg aggtcagttt tgccccaaat aaaccttttt ttgagtttat taatttaatt
 361 cctgatgata aaaatcaaac atttacccct caatttcggg caaaacacca attagataat
 421 aattataccg catattcatc aattttaagt aaaaaaattg cttatgctca acgttcccag
 481 tttgccttag ctgattttaa tgcaaatcat agaaaaatca ccaaaagttt caaacaaat
 541 atccaaaatc ttcgggaaac tgatttttca gtcgactttt cttcaagtca aacctcatta
 601 gcatcacaaa aaattccttt tcttacccgc gttgaagatt ttgccgcaga tattaacaaa
 661 tccggaaacc aagaagaggc aatttcaaga atttcgaaat acttccctga ttttcaaaga
 721 tatattcatg agttaaaaga tgatcctaat aatgttttac cttttaaaaa aggtaaaatt
 781 tttgactta gtattacaag acgtgctggt acaaatgatt ttattagtct aagtgctaat
 841 tctgaaccaa gttttttaat aaaagcaaga ctcacaaatg aggctaaatt tgaacttcgt
 901 ggccttaata ttgaagaagc agaaatgctg gaagagatta aattagttcc agttgatcaa
 961 tttgttgtta atcttgaaac cgatctaaaa ccaggtcaag cccagaaaa gtcacaaaaa
1021 cctcaaagtg aacaaaccga gattaaaaaa acttattttg ccgaaattga taaaatttta
1081 agtaaaataa caatgcgcaa acttcaactt gcgacttta aggtagctcc acagacaagt
1141 tcttcgcaac caaagcaagt taaagcaagt gtttcagctt gatctaactt agatcaaggg
1201 caagaaaata gaattttagt tccggttagt cagcaaagtt cgaatccaca acaacaccaa
1261 caacaacaac ctcaacctca aagtcagccc caacctcaac ctcagagtca acctcaatct
1321 cagccgcagc ctaatgctca aactcagcct aaggctcaag ctcaaagctc tcctaaagcg
1381 ccagtccaaa aaccggcaac tcctgatcca tctaaatcat ttaaaattag aacaaaacgt
1441 gccagagact ttcttaaaga gtttaataaa acattttata ggtctaataa acttaaatca
1501 caaaaactgt aagaaaaaat taattctgaa tatttatcta ataaaattgg aattgatctt
1561 ggcgttctaa aaaaatatat taataataat caagggattg aatatacttt tgatattgca
1621 aatgcaaaaa taagggatgc tcaagatgga attacaagcc atattgaaat tccagtaaca
1681 attagtcttt gatcaagttt ctttggtgat tcagataatg ttttactaaa atcaaaaaca
1741 gaaactttca tcatcccta tttccaaaag gaaactacat ctgaatcaaa agaccaaaaa
1801 gtaggacata cccaaaaaga actcgatcta atcagaaac taatttatca actcagtgaa
1861 ctaccaggaa caagcgccca aggttcttct ggatctagtg cacaaacaga acaaattaaa
1921 gaagttaaac tcccaacact aactgctttt atttcaaaac aagaactaga agctctaatt
1981 gatgggata agaatttagc tagtcagcca acaagtcagg cagtatctgt ttctcaagaa
2041 gttaaaacaa ccgagttcca acaacaagag gcaaattcaa ctaattctag tccaagtagt
2101 ccaagccta gtccaactag tccaagtcca gctagtccaa gttcaagccc tagtccaact
2161 agtcctaaaa atctcgatga aaatatagga gtgccaaatc ctagatttga ggaaattaaa
2221 aaataatta gttccgagtt tacttataag tataatttc gtgctaacga ggcacttttta
2281 gatgcttgag ttggaaaaca aaattttccca agtctaaaag atatttccca gtttagatca
2341 gatcaaagat tagcaaaaga ttatatactt gttaacttaa aatctaataa attcctaaaa
2401 gaagattatg atgttcttgc ttttttatgct aatttagtcc agaaagatcc aagagaagtt
2461 cttcaatatt tatttgaaat tgcaaaagct aataatttaa ttggtcctga agaaaaatta
2521 gatcttaacc agatcgaaga tgatggcatc tttagacgag ctaaggcaat taaacttata
2581 gataaatcaa gtaataacca aggaattta ggattttct ttaataacca gtttttaaaa
2641 ttccacgaac gtggatggat gtcaacttta tatttaccta atgaggcaaa aactaaatta
2701 gcagattatc aaaatctttt atccgctggg ataagcgata ccaagatttt tagtgaactt
2761 aataaaattc aacctttaga tctaaatatt aaagtccaaa gtagtgattc aagtgattca
2821 aaatcagatt caagtgattc ttcagatgct aagaccactt ctacaaagca agatcttcta
2881 agtaaattaa ctagccttaa atctcaaata gaggctatag ttaaaaata tgaaacagag
2941 tctaaaaatt atttagggac cgaaaataat aatagtagca gcagctcagg tactgaacag
3001 aagggctcat ctatccctga agaaaataaa aaattcatct tggaaaaatac agcaaaactt
3061 gataattag ccgatctact tttagctttc tattatcagg ctaaaagatt aaattttgca
3121 agttgaagtc aactccaaga cgaagatctt gactatcaaa tacaatttga gaaagaggct
3181 aataacactg agtcttcatc ctcttcatct tcttcatcct cttcatcttc atcttcttct
3241 tcttcatctt cttctgaaac cgatacaaac aaacctgaga atgcagttga atataaacta
3301 acttattatt ataaaattta taataaaact actaagaaag tagtttatac tacacctaaa
```

FIG. 7B

```
3361 acaattatca agctttatct tgcaagttct aatatcggag ttaaagaaaa acaagaacgt
3421 gaattaatga ataaattagt tttatctatc ccttcagctt attcaatttt ctatctaaaa
3481 caaagtgaat gagaacaagt taaaacaaat aatggccaac aaatgggtca gactggttcg
3541 agtcaagggt ttgagtctct tgaaccattt aagaaaatcc aagagatagt ccataaaaat
3601 aataaagact atgatctcaa agttgtaact atccgcgatg atgcttatgc agaaaatgct
3661 aaaattgttc acttaagggt ggttagaaaa gaagaacagc aagcagaaca aaaagagaaa
3721 gagaaggaaa aagaaaagga aaaggaacaa aaagaaacaa gttcccaagg ccaagttccc
3781 cagtcagcat ttttcttcca agttagactt ataaaagatg attatcaagg agcagaggcc
3841 tcaaatcagc aaacaagtag gcaagcgatg caaatgccaa acatggaaag ccaaaattca
3901 ggatcttctt ctagtgctcc ggcagcagct gctgctgcta aggcggcgag gtaa
```

FIG. 7B (continued)

```
atgaag ttagcaaaat tacttaaaaa acctttttga
ttaataacaa caattgccgg aattagtctt agtttatcag ccgctgttgg tacagttgtc
ggaattaatt cttataataa atcatattat tcttatctaa atcagatccc gagtcagcta
aaagtagcaa aaaatgctaa aattagtcag gaaaaatttg attcaattgt tttaaatctt
aaaattaaag ataattttaa aaaatgatcg gcaaaaacag ttttaactgc tgccaaaagt
gatctttatc gttataatct tgtttctgct tttgatttaa gtgaactaat aaacaatgat
tatttagtaa gttttgatct tgaaaatgca gtagttgatc aaaattcaat taaaaatgtt
gttatttatg caaaatctga taaggatcaa ataacttatt caaaacaaat tgtacttaaa
ggctttggaa atacagaaca agctagaact aattttgatt ttagtcaaat tgattcaagc
aagtcttttg ttgatctttc aagagcaaat ctaactttga tggaattcca aattttgctt
gcccaaaatt ttgaaaatga agaggaagt aattgatttt cacgacttga aagagctttg
gttgcatcaa aagcgagtct ttcactttat aattccttag gagaacccgt attttttaggc
ccagattatc aattagaccc agttttggac cgaaaaaaat tattaacttt gttaaataaa
gatggaaaat tagttcttgg acttaattta gtgcaaattt caactaaaaa aactatgaat
ttaaatcttg aagttcgcgg cgcgatttca aatcaggaaa tttctaaaat tctaaaatcc
tgacttgaaa caaatcttca aggcaaatta aaaaccaaag atgatttgca atggcacta
gtaaaagata aaattagcct ctctgattat tgatatggat ctccgaattc aaaagtaaat
acatcccaaa ttttaacaaa aagtaaagaa tttaaagatc ttttttgattt aagtgagaca
aattttttc ttaataccaa aatcggaact gtctatttaa gtattattcc caaacttta
gatccaagtc agatttctgt tgttgataag aaaaaactag ttgaaaatca aaaaattcgc
tttgaaatta ctgcttcttt aaaacgaaaa gctattgata aaaaatttat catccaggat
cttccagttt tgttgatct aaaagttgat tttaataaat accaagccgc tgttgcccaa
atgtttggaa cgataaaagc agttaaagaa ttttcaatgc ctgaagatca agatgcaaaa
actttatcct caaatgaaat aaaacagcga gttgatcgac ttttttgaact agcaaaaaca
gtgactaatt tggaaaatcc aagtgaagaa gttcttaaaa gcatttattt attaaatacg
ggaaaatatt tagtcgacca agaccaggaa aaagtaaaac aagagctaaa aaccgtgatt
gagggcttaa aatcaaaggc aaatactcaa aaaacagaaa aaaatagccc cacacaaccg
aaaaaaccag aggtttcact agctaaaaca acagaaaatt cagcaaaaac agtcaaggta
agcacttttg cagaagaagc taagggtcaa agtcaaagtc agcaaacaca accagtttcc
acttcatcgc ctcaaactag tcaaaattca cttcctaatt ccacaagcag ctcaaattct
gtattagaaa atgaaaaatt tgggacaagc atttgaacag cttttaattt cgctaatatt
tataatcttg aaaatacaaa aagcgaatat gagatctcaa ctttaggaaa taagctattt
tttgatttta aattagttga taaaactaat caaaatctaa ttttggctca gtccaaaatt
agtcttaata atattattaa ttctaataaa tctgcctatg atataattaa gaaattcaat
cccgatgtgt tttagatgg aacaattaat tatcaaaatc aaggaaaaga taaaaaagaa
tttatcctaa aagatttaag tgataataaa ttaatattta atcagaaga tgcaattcaa
actgatcaag gtttagagct aaagaaacct ttgaaattac agtcaaaatc gtctaatcca
gaaaaagaaa tatcaacttc tttatatacc ggagcaattt atttagtttt tgatgcaaaa
aatatttccg atggtaattg gattaatctt ttagccgata gaaaaggaaa agggcttgta
attaaagttc aaaattcaaa taataatgta cctaaaacca aagaaattgt tgagaatggt
acctatttat atgaaattct tgctggcaag gattcgatta aggtaaattc ttattttttt
ccaacaaagt acccaaaacg tgtaaaacgt cttaaattcg agattaaccc taaagacacc
ttgccaaatt tctttacttt agaatgattt catcttgatt ggtatcaaat cggcccaggc
gaacaaaata aaaaaccaca acaaaacgct aaaaagaac ctacaattat attaaaaacg
ctggcaatat ttaatgataa atcatttgca gagaaaggaa gtttaacaaa aagaagtgaa
ttaattaacg ggttgattag aaactatgtt aaaaagtaa
```

FIG. 7C

```
atgagtaaat tgacaaaatc gaaaactttt aaaattggtt tggttgggtc tattattggt
cttggagttt ttggtctaac tgtcggactt agcagcttgg caaaatacag atcagagcat
ccgcggaaag ttgtaaatga ttttgctaca aaagtttcaa ctttatcctt tagtccggat
gcttttttg ctaattctga ctattgaaca atcaaaaatc acctttaga ttccaagaac
caaatcaaaa atagcgaaaa ggttctaaaa tcctttttct tttttctaa aaacggtgat
cagttagaaa aaattaacct tgaagatcca gaatataaaa atgccggaat ttcctttcat
attcttgaaa ttatccctga tgatgtcaat caaaattta aagtcaaatt tcaattatga
caaaaatttg caaacgggga tatagcaaaa tctgatattt atcaagaaga aagtgtcgct
tttataaagc agtcaaatct tttagttgcc gaatttaatt tttcacttaa gaaaatcact
gataaattaa atcagcaagt aggaaatcta tccctaaaat ctacaaattt tgccgatgat
ttagcaaagt taacaaaacc gacatcctct tataaaaatc cggcaagttt tcgtgtactt
gattttcaag aagatctaaa tcaggcacga aattccgaag aattagtcaa aaaacttgct
atttatttc cttcacttga taatttaata acaaagctaa atgaatcttc agaaaataaa
ctaccggaa attctgggca tattttcgaa tttagtcttc gcaaatcaca ggcaactaat
caatatgtca gcgttcagaa ccaaattcca tttctatttt tagaagcaga tcttagtcaa
agtgctcgtg atttaattgg tcaagatttt aattttcgcc caatagtttc atcaattaaa
ctacaaaaac aagacaattc ctcctacttt ttagatttta atcagttttt aggcaactta
aagttaaaag atattagcaa aactgatttt aatgagcaag gtttaaaaac ttcggcctat
gaaattctta gtacaattag gtctggtttt tttgataata acgatcttcg ttctgatcaa
gccaaagaat caattaataa aatattaaaa aataaaatta aatttgattt tggcaagtta
gatgcaattt tttctgacaa gggaaattct gaaagtcttc aatattatct agatgtaaaa
aaggcaagtc ttgataaaac tgataaatca acaatttaa ttccttttcg tctaaaagtt
gatgaaagtt ttttcaaaac ttcaactaat ttaccagaga atatcattgc tcgaaaagat
ggaatttta aactaaccgg atttgaccaa gggctaaata atcaacttcc aaaaataaat
caagaaattt ataaaacaaa atatttatca tttttcgaaa aaggtaagga aatcaagat
ttagttgatt ttgggagtga accgataaat ggtcctcttt taatttctaa agttgaagcc
gatgcacttt ttaaagaaaa caaaccagaa gcaattcata aagtacttga aactaattat
aattatcaat ttaatcctta tcagtcttta cttgattctt gaacaggaaa tttagtacag
ccaaaacttg aaaacattaa agctttaaat gaaaatgaaa aagcggcagt atccgaagcc
ggaattgctg aaatttttatc acgtgatttt tttctagatg ggcatcaagt tgctagtttt
tatcaggatt tactaacaaa agatcggcta acagttatcg aaactcttta tgaattaggt
aaaaaatggg gccttcatac aaatacagct aatttcccac gctgaaaatt tagaaatgca
aaaaacattt tcgaggaagc aacacagtat aaattcctac tgggtaaaaa aggtaaagaa
aattttagaa aaataaccaa acttactttt aatggtttat atcgcaatga aaaaggtcaa
ggatttttatg ctactttagt tctgccaaaa gaaattaagg ataaattagc aaataaaact
gatgctgagg ttttttgcaga attaaaaaaa cattcttaa ttgattcttc cgggtttaaa
actataaata ttgacaaaaa tctttttagaa ggggaagact ttgaaaattt tggtgattta
ttaaaagctt ttttccttaa agctgcccaa tttaataatt ttgctccttg agcaaaatta
gatgataatc ttaaatattc gtttgtgccg aaaaaaggag atcaagaaaa agagggcaaa
aaagctgaaa ttgataaaaa agttaaggaa ttaacagata aaattagttc accggggtca
gttctgccaa aatcagaagc aggtaaaccc gtggcggcta accagaagc tgcaaaacct
tcaagctcaa caacaagttc agttcctcg gcttcattag aaggaaatta tcttccaatt
tcatttgaat ttaaactttc ttatcgtgat ggagcaaaat cggagttaaa aacaccggaa
attaaagtat ttttagaact tcagaccgat aaagattatc aagaaaataa aattatcaaa
gaattagata aaacggtatt agaactccaa agcgaattta agaatgaag attagatgag
tctgcatttt cttctttaac ttttcctaaa agccaaaaaa gtgaaggaac tcaaaatcaa
ggtaaaaaag ccgaaggtgc tcctaaccaa tctaaaaaat cagaggaaaa tagcaataag
ctaacagaat atattcaaga attaggtaca aaagtagaaa atcccttaa atcaaaagga
aaaaactact ctgctgaggt tgaaaaaatt atagaagcat ttctgggggg atataaattc
cttgactttg cattagtaga acaaactcca aaacctgaaa ctccaaaaac agaagcagca
aagcctgaaa ctacaaaacc agttgccgcc cgtcctgagg cagcaaaagt tgctgccaaa
ccttcagcgg ccaagcccgt tagttcccca gcgccaaaaa aatcaacact ttatgttcgc
gttctcatta gaaaaaaaga aaataaacaa gtcaaataa
```

FIG. 7D

```
atgaaga aacaaattcg caacaaagca ataatcgttc tagcaggtct tagttttatt
gggataaccg cggggagtggg tctggctgtt caaaattcag cgcttagatc ctcttatctt
aatcaattta aaaatgataa atctgcaact gaattattgt caccaataaa tgatactgaa
ttatccaaga taatcagtaa ttttagctta aaagaaaact gaagtaaaat atcagctggt
caagcttttg aactccataa aaatccttta tatgccttta aattaacaga tgcaatcgat
ttttccaaaa tcgataagaa attcgcgcat ctatttttta atgttcaggt taatgataat
actaaagttg aaggtaattc aattagaaat ttaactgttt ttgtttttga tgcaattaca
aaaaaagaag tcgctactcg agctttcat acaagtctta gtgggttttc aagtgttgca
aagaagatt ttatcgaaaa tttcgttgct gaatcttcaa cttacgaact tgataaagat
caattaaaga aaaattttgc taccgaaata gttctaacct cagcttttc tattaaattc
caagatgttt tactaactca tctaagaaaa acttccccag aaagttttca agaaacaaaa
actatccaag ttagagcact aactaattca attactgagt tcaacaaca acaacaagag
ggcggatctg gaggatctgg gacatctggg ggatccagtg ggggaagttc ttcaggttca
acagatcaaa aagggcaaac aagtcaaagc tcagaaaagg aatctaagtc cgaaaaggaa
aaggaaaag atcagcaaag cactcaaggc tcagaacaaa aacaagatca aaagcaacag
aagcctaaag aagcagaaaa gccagctcaa gaaaaaccag ctcaagaaaa gccagctgag
acaccaaaag ttaaagcccc agttattgag cctgtgaaaa aattagtatt tgaaaatgaa
aaattaaatc aagcattact tgagacacta aaagattttg gtggccttaa attactagcg
gcttccggac ttcaaggctt attaccaaat gaatatactt tattaccagt ttcttctgat
aaatcattaa taaaacttga tatagatgac caggcaggaa cagcatcaat tcatcttaaa
ttattagata aaaataagaa ggaaaaaaat ctaatcctgc aataaacgg gcttgcttca
attggtgcga tcaaagataa agtgtttagc cagatattta gaaccagaa tgcttattta
actataagac ctcagattaa tgaatatcta agaaaaaatc ctagaaaaaa aattcaggaa
gtaatttgaa gtttttcaag ggaaaaattt gatcaactcc gtgggcaaaa tgaagtagaa
aaattcttag aggaactttta taatccaacc cagacaagcc aaagccctca gaaaagtaaa
agttctgatt ctgcgaaaaa caatgtagca acaattcaag cttcaccaga cagcacca
aaaacaacaa caacaaattc taatacccag tcaagttcta cttcaacaaa taatcaatct
tctaatggta gccaacaaat ggcaagtcct caaactgaat cctcacttag tactgcgaag
acctcagagg caagtaattc ttctgaagaa tctagttcag agaccaaagg gacaaaagag
caagctaact cagagacaaa cccaatggga aaatcccagg caaaaccgga agcaaaacca
gaggaaaaac aaattaattt agaggatcaa gcaaaaacag agctaaaaga aattctaaaa
attcatggtt gaaattatag aacacttta aaagatcaaa accaaaaagt aattcttcct
gataatatta atttttggtt tgatcttaga aataaaagat catctatga aaattataaa
ttagaatttg atcttgttaa aaaacaggt cagattcaag caggtgatgt aattgatgca
aataaaatcc gccttaattt aaaaattagt cctctagcta atcttaaatt agaagtagat
tcaaaaaata aacaatatat tgacgccgga caaataggcg actatgttga atttgacaaa
caagggaaaa aactagtaga gcaagggaaa tctttagatc ttaaagttgg agcttcagct
gcaaattcaa tatttagtcc agaaattcgt tattcagctt atgaattaaa gggttgaact
tatccaattg atattgatat taaaggaaat ccaattcaac aagaacttga aaaattagtt
ggtaattttc acaaagttgg aattaataaa aataatcaat accaaattta ttcaacagac
attgacaaga ttttttgtca agctaaactt gataaatatt ttgagctaag tcaagaagaa
aaacaagcct caaaaaaata tcttcaagaa aaacttaatc caattagtga ataaccatt
gtaaaactcc ctccaaaaga agaagttctt cccccactag aagaagagaa aaaaccagag
caggaccaaa aagcacaaga aaacaagaa gataaacaaa accaaaaaca acaagaaaaa
caagaagata aaaagaaca agaccaacaa aaacattctc aaagccctga ccaaaaaact
gaaactcaaa ctcatgacca agaaaagat aaacaaacta gtcagaaac tagtccttca
aatactaatg agtcttcagg gacacaaaat actgctcaaa attcccagac aaatcaggca
aattctggac aaggtcaaag ccaacaagca gcatcatctt caacttcata ccaaactcac
aaaataacaa cttccaagat gatcaaaaa gatcaaacta tgaacaaac agaaaaagaa
attgaacctg aaaattagc ctttggtgat tatcttgtta aatatcttga tatttttgaa
actttaaag ttggcccaga tcagaaatta tcaattggta gatgatataa tgcgccccaa
agaacttata atgttatatt ccgggtactt gataaggaaa atattcaagt agctgcatcc
cttttccaat tacatggtat atcagcaact aatattgccc ttgaaaaatc acttcgttat
gctcctgata ttttccttga tggaacttcc ggtcttgaat ataaacaaga tacaggggac
aagccatatc ttcaaggaag gcaatttgtt tcggcaatta attcaattaa taatactaaa
tcttcctatc gggtacataa acttttttgat aatctacctt tatcagaaga atcaagtcag
```

FIG. 7E

```
ggtctaagac ttaaatcttc acttgtttat gactatcaaa aaaatgatcc ttatactttc
caggcatcca aagaagctct aagaaaaact gcacttacta aaggagtttt atatttagca
tttaaacctg aacaatttt aggaataaaa ggatcaaaga cagctccagg aagaaactat
aaactttat caacaaccaa tgttcatttt aaatctttat atggactctc taatcttgaa
ctagtaaaaa ccaaatacca agaaaacctt aaattagtct gaaaactaat cggggcaaaa
ccagttaatg atgataagat cttacctcca caagtagcag atcttcctag acatagatca
actgagatta ttcttttaga agattcaaaa ccaggtgcat cttcatcgcc tcaaactaaa
gaaaatagcc aaaataaaga agctgagacc ttcaatttag atattagaca aactaaacca
aatcagatcg aaccacttga acattatctt ggtcaaactt gattaatgga ataagaatt
gatgatgaaa gtgcaacaat tacgataatt cctgaacaac aagaaagaga agatagcaaa
ctaaaagttt gaaaatccga aattaagatc aaagataaaa ataaataccaa aaaccaggat
acaaactgag aaaccgagct agcttctgtt ttaggtagag gatttgacta tggacagatc
ggtgatacaa ccccacaagc ttctaatccc caagaccgag tgggtatgac ctttaaaggg
tttgccgtat ttaaaggcga taaactctta aatgataaag caagactaaa tgtgcgcaaa
gcctttatgg atcaatattt taagaattat tcttag
```

FIG. 7E (continued)

```
   1 atgaaaaaca aaaaatcaac attactatta gccacagcgg cggcaattat tggttcaact
  61 gttttggga cagttgttgg cttggcttca aaagttaaat atcggggtgt aaatccaact
 121 caaggagtaa tatctcaatt aggactgatt gattctgttg catttaaacc ttcgattgca
 181 aattttacaa gcgattatca aagtgttaaa aaagcacttt taaatgggaa aacctttgat
 241 ccaaaaagtt cagaatttac tgattttgtc tcaaaatttg actttttgac taataatggg
 301 agaaccgttt tggagatccc gaaaaaatat caggtggtta tctcggaatt tagccccgag
 361 gatgataaag aacgttttcg tcttggattt catctaaaag aaaaacttga agatggaaat
 421 atagctcaat cagcaactaa atttatttat cttttaccac ttgatatgcc caaagcggcc
 481 ctgggtcaat attcttatat cgttgataaa aattttaata atttaattat ccatccttta
 541 tctaattttt ctgctcaatc aataaagccg cttgcactga cccgttcaag tgatttata
 601 gcaaaactta atcagtttaa aaatcaggac gaactttgag tttatcttga aaaattcttt
 661 gatcttgaag ctctaaaagc aaatattcgt ttgcagacag ccgattttag ttttgaaaaa
 721 ggcaatttag ttgatccttt tgtttattct tttattagaa atcgcaaaaa tggaaaagaa
 781 tgagctagtg atcttaatca agatcaaaaa accgtcagac tttatcttcg aaccgaattt
 841 agtcctcagg ctaaaaccat tttaaaagac tataaataca aagatgagac tttcttaagt
 901 agtatcgatt taaaagcaag taatggaact agtttatttg ctaatgaaaa tgatctaaaa
 961 gatcaattag atgttgatct tttagatgtc tctgattatt tggaggcca atcagagaca
1021 attactagta attcccaagt taaacctgtc ctgctagtg agagatcttt aaaagatcgg
1081 gttaaattta aaaagatca gcaaaaacca agaattgaga aatttagttt atatgaatat
1141 gatgctctaa gttttttatc ccaacttcag gaattagttt ctaaacctaa ttcaattaaa
1201 gatttagtta atgcaacttt agctcgtaat cttcggtttt cattaggaaa atataatttt
1261 cttttgatg atttagccag tcatcttgat tatactttt tagtttcaaa agcaaaaatt
1321 aaacaaagtt caattacaaa aaaattattc attgaattac caatcaaaat tagtcttaaa
1381 tcttcaattt taggtgatca agaacctaat attaaaactt tattcgaaaa agaagtaact
1441 tttaaattag ataacttccg tgatgttgaa atcgaaaaag cttttggact tttatatcca
1501 ggtgttaatg aagaacttga acaagccgga agagagcaaa gagcaagttt ggaaaaagaa
1561 aaagcgaaaa agggtcttaa agaatttagc cagcaaaaag atgagaattt aaaagcaata
1621 aataatcaag atggtcttga agaagatgat aatattactg aaagacttcc tgagaattcc
1681 ccgattcaat atcagcaaga aaaggccggt ttaggttcaa gtccggataa accttatatg
1741 ataaggatg tccaaaatca acgttattat ctagcaaaat cacaaattca gaactaatt
1801 aaggccaaag attataccaa attagccaaa cttttatcca atagacatac ttataatatt
1861 tctttaagat taaaagaaca acttttgaa gtaaatccaa gaattccaag ctctagagat
1921 atagaaaatg caaaattgtc tctagataaa accgaaaaaa ataaatactg gcagattat
1981 tcaagtgctt ctcctgcttt ccaaaataaa tgatcacttt ttggatatta ccgttattta
2041 ttaggtcttg atccaaaaca aacaatccac gaattagtaa aattaggaca aaaagcgggt
```

FIG. 7F

```
1981 tcaagtgctt ctcctgcttt ccaaaataaa tgatcacttt ttggatatta ccgttattta
2041 ttaggtcttg atccaaaaca aacaatccac gaattagtaa aattaggaca aaaagcggt
2101 cttcaatttg aaggatatga aaatcttcct tctgatttca atcttgaaga tcttaagaat
2161 attaggatta aaacaccttt atttagtcaa aaagataatt tcaaattatc tttacttgat
2221 tttaataatt attatgatgg tgaaattaaa gccccagaat ttggtcttcc tttatttta
2281 ccaaaagaat taagaaaaaa tagttcaaat attggtagtt ctcaaaactc taatagccct
2341 tgagaacaag aaattattag ccaatttaaa gatcaaaatc tatctaatca ggatcagtta
2401 gcccagttta gtactaaaat ctgggaaaaa atcattggtg atgaaaacga atttgatcaa
2461 aataacaggc ttcagtataa acttttaaaa gatcttcaag aatcttgaat taacaaaact
2521 cgcgataatc tttattggac ttatctaggt gataaactta agttaaacc aaaaaataat
2581 ttagatgcta aatttagaca aatttccaat ttacaagagc ttttaactgc tttttatacc
2641 tcagctgctc tttctaataa ctgaaattat tatcaagatt cagggcaaa gtcaactatt
2701 attttgaag aaatagctga gctagatcca aaagtaaaag aaaaagtagg agctgatgtt
2761 tatcaattaa aattccatta tgcaatcggt tttgatgata atgctggcaa gtttaatcaa
2821 gaagtaattc gttcttcaag tagaacaatt tatcttaaaa cctcagggaa atccaaatta
2881 gaagcagata caattgatca acttaatcaa gcagttgaaa atgcaccttt aggtcttcaa
2941 agttttatc ttgatactga aagatttggg gttttccaaa aattagcaac ttccttagca
3001 gttcaacata aacaaaaaga aaaaccacta cctaaaaaac taaataatga tggctatact
3061 ttaattcatg ataaacttaa aaaaccagta attccccaaa ttagttcaag tcccgaaaaa
3121 gattgatttg aaggtaaatt aaatcaaaac gggcaaagcc aaaatgtaaa tgtctcaact
3181 tttggttcaa taatcgagtc cccttatttt agtactaatt tccaagaaga agctgattta
3241 gaccaagaag acaagatga ttcaaaacaa ggaaataaga gcctagataa tcaagaagca
3301 ggtcttttaa aacaaaaact ggcaatttta ttagggaatc aatttatcca atattatcaa
3361 caaaatgata aagaaattga attcgagatt atcaatgttg agaaagtttc agagcttagt
3421 ttccgcgttg aatttaaatt agcaaaaact cttgaagaca acggaaaaac tattcgagtt
3481 ttatcagatg agacaatgtc attaattgtt aatactacaa ttgaaaaagc accagaaatg
3541 agtgctgctc ccgaagtatt cgatactaaa tgggttgagc aatatgatcc aagaaccccg
3601 cttgcggcta agacaaagtt tgtcttaaaa ttcaaagatc aaataccagt tgatgccagc
3661 ggaaatattt ctgataaatg actagcaagt attcctttgg tgattcacca gcaaatgttg
3721 cgtcttagcc cggtagttaa aacaataaga gagcttggtc taaaaactga acaacaacaa
3781 caacaacaac aacaacaaca aagaaagct gttagaaaag aagaagaact ggaaacctat
3841 aatccaaaag acgagtttaa tattcttaat cctttaacaa agctcaccg tcttacctta
3901 tcaaatttag taaataatga tccaaattat aaaattgaag atttaaaagt aatcaaaaat
3961 gaagcaggtg atcatcaatt agaatttct ctaagagcta ataatatcaa aagattaatg
4021 aatacaccaa ttactttttgc tgattataat cccttttttct attttaatga ggactgaaga
4081 aatatagata aatatttaaa taataaagga aatgtgagtt ctcaacaaca acaacaacaa
4141 caacaacaac caggcggggg taatcaaggc tcgggtctaa tccaaagact taataaaaat
4201 attaagcccg aaacttttac ccccgcactc atagctctta aacgagataa taatactaat
4261 cttttctaact attctgataa aataataatg atcaaaccaa atatttggt tgaacgatca
4321 attggtgttc cctgatcaac cggccttgat ggttatattg gttcagaaca actcaagggc
4381 ggaacttcct caaacggtca aaagcgattt aagcaagatt ttattcaggc tttaggtctt
4441 aaaaacactg aatatcatgg taaactaggt cttcaattga attttttga tcctggaaat
4501 gaactagcaa aaattaagga tgcttcaaat aaaaaagggg aagaaaact gttaaaatca
4561 tatgatttat ttaaaaacta tttaaatgaa tatgagaaaa atcccctaa aattgctaag
4621 ggatgaacaa atattcatcc tgatcaaaaa gaatatccaa atccaaatca aaaactacct
4681 gaaaattatc ttaacctagt tttaaatcaa ccttgaaagg ttactttata taattcaagt
4741 gatttatta ctaatttatt tgttgaacct gaaggctcag atcggggatc tggagcaaaa
4801 ttaaaacaag taatccagaa gcaagttaat aataactatg ctgactgggg gtctgcatat
4861 ctcacgttct ggtatgataa agatatcatt accaatcagc aaatgttat aactgctaac
4921 attgctgatg tctttattaa agatgtaaag gaacttgaag ataatacaaa actaattgct
4981 ccaaatatta ctcaatgatg gccaaatatt agcggctcaa aggagaaatt ttataagcca
5041 acagtgtttt ttggtaattg agaaaatgaa aacagcaata tgaattccca ggggcagacc
5101 cctacctggg agaagatcag agaaggattt gctctccaag cgcttaaatc cagctttgat
5161 caaaaaacaa ggacatttgt ccttacaaca aatgctcctt tacctttatg aaaatacgga
5221 ccattaggtt tccaaaatgg gccgaatttc aaaacacaag attgaaggct tgttttccaa
5281 aatgatgata accaaatagc cgcgctaaga gtccaggagc aagatcgccc agaaaaatca
```

```
5341 agcgaagata aagacaagca aaaatggatt aaatttaaag ttgttatccc tgaagaaatg
5401 tttaattccg gtaatatacg ttttgttggg gtaatgcaga tccaaggtcc taatacttta
5461 tgacttccag tgattaattc ttcggttatc tatgacttct atcgcggaac aggagattct
5521 aacgatgtcg ccaatcttaa tgtagctcct tgacaggtta aaacaatcgc atttacaaat
5581 aacgccttta ataatgtttt caaagagttt aatatctcta aaaaatagt agaataa
```

FIG. 7F (continued)

```
   1 atgagtaaaa aatcaaaaac atttaaaatt ggtttgactg ccggaattgt tggtcttgga
  61 gttttttggcc taactgtcgg acttagcagc ttggcaaaat acagatcaga aagcccacga
 121 aagattgcaa atgattttgc cgcaaaagtt tcaacattag cttttagtcc ttatgctttt
 181 gagactgatt ctgattataa aatagtcaaa aggtgactag ttgattctaa taacaatatt
 241 agaaataaag aaaaagttat tgattccttt tcctttttta ctaaaaacgg tgatcagtta
 301 gaaaaaatta attttcaaga tcctgaatat accaaagcga aaataacttt tgagattctt
 361 gaattatcc ctgatgatgt caatcaaaat tttaaggtaa aatttcaggc attacaaaaa
 421 cttcataatg gtgatattgc caaatctgat atttatgagc aaacagttgc ttttgccaaa
 481 cagtcaaatc ttttagttgc cgaatttaat ttttcgctta aaaaaattac cgaaaaatta
 541 aatcaacaaa ttgaaaattt atcaacaaaa attacaaatt tgctgatga aaaaacaagc
 601 agccaaaaag atccctcaac tctaagagct attgatttcc aatacgattt aaatacagcg
 661 cgaaatgctg aggatttaga tataaagctt gctaattatt ttccagtact taaaaattta
 721 ataaacagac taaataatgc tcctgagaat aaattaccta ataatttagg taatattttt
 781 gaatttagct ttgcaaaaga tagttcaact aatcaatatg taagtatcca gaaccaaatt
 841 ccttcgctgt ttttaaaagc agatcttagt caaagtgccc gtgaaatttt agctagccca
 901 gatgaagttc agccagttat taacatttta agattaatga aaaagataa ttcttcttat
 961 tttctaaatt ttgaggattt tgttaataat ttaacactga aaaatatgca aaaagaagat
1021 ttaaatgcaa agggtcaaaa tctttctgcc tatgaatttc tagcagatat taaatctgga
1081 ttttttccctg gagacaagag atccagtcat accaaggcag aaattagtaa tctttttaaat
1141 aaaaagaaa atatttatga ctttggtaaa tacaatggaa aattcaacga ccgtcttaac
1201 tcgccaaatt tagaatatag cctagatgca gcaagcgcaa gtcttgataa aaaagataaa
1261 tcaataattt taattcccta ccgccttgaa attaaagata aatttttgc cgatgattta
1321 tatccagata caaaagataa tattcttgta aagaaggga ttcttaaatt aactggattt
1381 aaaaaaggtc caaaaattga tctccctaat atcaatcagc aaattttttaa aaccgaatat
1441 ttaccatttt ttgaaaaagg taaagaagaa caagcaaaat tagactatgg taatatctta
1501 aatccatata atactcaact tgccaaagtt gaagttgaag ctcttttttaa agggaataaa
1561 aaccaagaaa tctatcaagc acttgatgga aattatgcct atgaattcgg ggcctttaaa
1621 tccgtgctta attcctgaac aggaaaaatt cagcatcctg aaaaagctga tatccaaaga
1681 tttacaagac atttagaaca agttaaattg ggttctaatt cagtttttaaa tcaaccacaa
1741 acaacaaaag aacaagtaat ttcaagtctt aaaagtaata cttttttttaa aaatggacat
1801 caagttgcta gttatttcca ggattactc accaaggaca aattaacagt tctagagact
1861 ctttatgatc tagcaaaaaa atggggacta gaaactaaca gggcgcaatt cccgaaagag
1921 gttttccaat atacaaaaga tatttttgca gaagcagata aattaaaatt tttggaaggg
1981 aaaaaaaagg atccttacaa tcagataaaa gaaattcacc aactttcctt taatatttta
2041 gctcgtaatg atgtaataaa atctgatgga ttttacggag tttattatt gccccaaagt
2101 gtaaaaactg aattagaagg caaaatgag gcgcaaattt tgaagctct aaaaaatat
2161 tctttaattg agaactcggc ttttaaaact actattttag ataaaatct acttgaaggg
2221 actgattttta aaaccttcgg tgatttttta aaagcatttt tcctaaagc agcccaattt
2281 aataattttg ctccttgagc aaaattagac gataatcttc agtattcatt tgaagctatc
2341 aaaaaagggg aaactacaaa agaaggtaaa agagaagaag tagataaaaa agttaaagaa
2401 ttagataata aaataaaagg tatattacct cagcccccag cagctaaacc tgaagcggct
2461 aaaccagtag cagcaaaacc tgaagcagct aaacctgaaa caacaaaacc agtagcagct
2521 aaacctgaag cagcaaaacc agtagcagca aaaccagtag cagcaaaacc agttgctact
2581 aatactaata ctaatactgg ctttttcactt acaaatauac caaaagaaga ctatttccca
```

FIG. 7G

```
2641 atggcttta gttataaatt agaatatact gacgaaata aattaagcct aaaaacaccg
2701 gaattaatg tatttttaga actagttcat caaagcgagt atgaagaaca aaaaataata
2761 aaggaactag ataaaactgt tttaaatctt caatatcaat tccaggaagt caaggtaact
2821 agtgaacaat atcagaaact tagccaccca atgatgaccg agggatctcc taatcaaggt
2881 aaaaaagccg aaggcgctcc taaccaaggc aaaaagccg aaggcgcacc tagtcaaggg
2941 aaaaaagccg aaggcgctcc taaccaaggc aaaaagccg aaggcgcacc tagtcaaggg
3001 aaaaaagcag agggtgcttc taatcaacaa agcacaacta ccgaattaac taattacctt
3061 cctgaattag gtaaaaaaat tgacgaaatc attaaaaaac aaggtaaaaa ttggaaaaca
3121 gaggttgaac taatcgagga taatatcgct ggagtgcta aattgctata ctttgtccta
3181 agggatgatt caaaatccgg tgatcctaaa aaatcaagtc taaaagttaa aataacagta
3241 aaacaaagta ataataatca ggaattaaaa tctaaataa
```

FIG. 7G (continued)

ATGAAAGAGCTGGACAACAAGATCAAGGGCATCCTGCCACAGCCCCCA*GCCGCCAAGCC
CGAGGCCGCCAAACCAGTGGCCGCCAAGCCTGAG*ACAACAAAGCCTGTG*GCCGCCAAAC
CTGAAGCCGCCAAGCCAGAGGCCGCCAAGCCCGTGGCCGCCAAGCCCGAAGCCGCCAAG
CCTGTGGCCGCCAAGCCAGAGGCCGCCAAACCTGTGGCCGCCAAACCCGAAGCCGCCAAA
CCCGTGGCCGCCAAACCTGAGGCCGCCAAGCCCGT*GGCCACAAACACCGGCTTCTCCCTG
ACCAACAAGCCCAAAGAGGACTACTTCCCCATGGCCTTCAGCTACAAGCTGGAATACAC
CGACGAGAACAAGCTGTCCCTGAAAACCCCCGAGATCAACGTGTTTCTGGAACTGGTCC
ACCAGTCCGAGTACGAGGAACAGGAAATCATCAAAGAACTGGACAAGACCGTGCTGAA
CCTGCAGTACCAGTTCCAGGAAGTGAAAGTCACCTCCGACCAGTACCAGAAACTGTCCC
ACCCCATGATGACCGAGGGCTCCTCCAACCAGGGCAAGAAGTCCGA*GGGGACCCCCAAC
CAGGGGAAAAAGGCCGAAGGCGCCCCAAACCAGGGAAAGAAAGCCGAGGGCACACCT
AATCAGGGCAAAAAAGCCGAAGGGGCTCCTTCCCAGCAGTCCCCAACCACCGAGCTGAC
CAACTACCTGCCCGACCTGGGCAAGAAGATCGACGAGATCATCAAGAAGCAGGGGAAG
AACTGGAAAACCGAGGTGGAGCTGATCGAGGACAATATCGCCGGCGACGCCAAGCTGC
TGTACTTCATCCTGCGCGACGACTCCAAGTCCGGCGACCCCAAGAAATCCTCCCTGAAA
GTGAAGATCACCGTGAAGCAGTCCAACAACAACCAGGAACCCGAGTCCAAG

FIG. 8A

MKELDNKIKGILPQPP*AAKPEAAKPVAAKPE*TTKP*VAAKPEAAKPEAAKPVAAKPEAAKPVAA
KPEAAKPVAAKPEAAKPVAAKPEAAKPV*ATNTGFSLTNKPKEDYFPMAFSYKLEYTDENKLS
LKTPEINVFLELVHQSEYEEQEIIKELDKTVLNLQYQFQEVKVTSDQYQKLSHPMMTEGSSN
QGKKSE*GTPNQGKKAEGAPNQGKKAEGTPNQGKKAEGAPSQQSPTTELTNYLPDLGKKIDE
IIKKQGKNWKTEVELIEDNIAGDAKLLYFILRDDSKSGDPKKSSLKVKITVKQSNNNQEPESK

FIG. 8B

ATGTTGGGGAAATGCTTGACCGCGGGCTGTTGCTCGCAATTGCCTTTTTTGTGGTGTA
TCGTGCCGTTCTGTTTTGCTGCGCTCGTCAACGCCAGCAGCAGCAGCAGCTCCCAATT
GCAGTCGATTTATAACCTGACGATATGTGAGCTGAATGGCACAGATTGGCTGAATAA
AAATTTTGATTGGGCAGTGGAGACTTTTGTTATCTTTCCTGTGTTGACTCACATTGTC
TCCTATGGCGCCCTCACCACCAGCCATTTCCTTGACGCAGTCGGTCTGATCACTGTGT
CTACCGCCGGATATTACCACGGGCGGTATGTCTTGAGTAGCGTCTACGCTGTCTGCG
CCTTGGCTGCGCTGATTTGCTTCGTCATTAGGTTGACGAAAAACTGCATGTCCTGGCG
CTACTCATGTACCAGATATACCAACTTTCTTCTGGACTCCAAGGGCAAACTCTATCGT
TGGCGGTCACCCGTCATCATAGAGAAAGGGGGTAAAGTTGAGGTTGATGGTCATCTG
ATCGACCTCAAGAGAGTTGTGCTTGATGGTTCCGCGGCAACCCCTGTAACCAAAGTT
TCAGCGGAACAATGGTGTCGTCCCTAG

FIG. 9A

MLGKCLTAGCCSQLPFLWCIVPFCFAALVNASSSSSSQLQSIYNLTICELNGTDWLNKNF
DWAVETFVIFPVLTHIVSYGALTTSHFLDAVGLITVSTAGYYHGRYVLSSVYAVCALAA
LICFVIRLTKNCMSWRYSCTRYTNFLLDSKGKLYRWRSPVIIEKGGKVEVDGHLIDLKRV
VLDGSAATPVTKVSAEQWCRP

FIG. 9B

ATGAATGGCATCTTCAACACCCGCCTATCCCGCACCTTCGGATATACTATCAAGCGA
ACCACAGTCAGAACGCCCTCCTGGGCGGTGGACATGATGAGATTCAATATTAATGAC
TTTCTTCCCCCAGGAGGGGGCTCAAACCCCCGCTCTGTGCCCTTTGAATACTACAGA
ATAAGAAAGGTTAAGGTTGAATTCTGGCCCTGCTCCCCGATCACCCAGGGTGACAGG
GGAGTGGGCTCCAGTGCTGTTATTCTAGATGATAACTTTGTAACAAAGGCCACAGCC
CTCACCTATGACCCCTATGTAAACTACTCCTCCCGCCATACCATAACCCAGCCCTTCT
CCTACCACTCCCGCTACTTTACCCCCAAACCTGTCCTAGATTCCACTATTGATTACTT
CCAACCAAACAACAAAAGAAACCAGCTGTGGCTGAGACTACAAACTGCTGGAAATG
TAGACCACGTAGGCCTCGGCACTGCATTCGAAAACAGTATATACGACCAGGAATAC
AATATCCGTGTAACCATGTATGTACAATTCAGAGAATTTAATCTTAAAGACCCCCCA
CTTAACCCTTAA

FIG. 10A

MNGIFNTRLSRTFGYTIKRTTVRTPSWAVDMMRFNINDFLPPGGGSNPRSVPFEYYRIRK
VKVEFWPCSPITQGDRGVGSSAVILDDNFVTKATALTYDPYVNYSSRHTITQPFSYHSRY
FTPKPVLDSTIDYFQPNNKRNQLWLRLQTAGNVDHVGLGTAFENSIYDQEYNIRVTMYV
QFREFNLKDPPLNP

FIG. 10B

ATGGAATTCGGGGCCTTTAAATCCGTGCTTAATTCCTGGACAGGAAAAATTCAGCAT
CCTGAAAAAGCTGATATCCAAAGATTTACAAGACATTTAGAACAAGTTAAATTGGGT
TCTAATTCAGTTTTAAATCAACCACAAACAACAAAAGAACAAGTAATTTCAAGTCTT
AAAAGTAATAACTTTTTTAAAAATGGACATCAAGTTGCTAGTTATTTCCAGGATTTAC
TCACCAAGGACAAATTAACAGTTCTAGAGACTCTTTATGATCTAGCAAAAAAATGGG
GACTAGAAACTAACAGGGCGCAATTCCCGAAAGAGGTTTTCCAATATACAAAAGAT
ATTTTTGCAGAAGCAGATAAATTAAAATTTTTGGAAGGGAAAAAAAAGGATCCTTAC
AATCAGATAAAAGAAATTCACCAACTTTCCTTTAATATTTTAGCTCGTAATGATGTAA
TAAAATCTGATGGATTTTACGGAGTTTTATTATTGCCCCAAAGTGTAAAAACTGAATT
AGAAGGCAAAAATGAGGCGCAAATTTTTGAAGCTCTTAAAAAATATTCTTTAATTGA
GAACTCGGCTTTTAAAACTACTATTTTAGATAAAAATCTACTTGAAGGGACTGATTTT
AAAACCTTCGGTGATTTTTTAAAAGCATTTTTCCTTAAAGCAGCCCAATTTAATAATT
TTGCTCCTTGGGCAAAATTAGACGATAATCTTCAGTATTCATTTGAAGCTATCAAAA
AAGGGGAAACTACAAAAGAAGGTAAAAGAGAAGAAGTAGATAAAAAAGTTAAAGA
ATTAGATAATAAAATAAAAGGTATATTACCTCAGCCCCCAGCAGCTAAACCTGAAGC
GGCTAAACCAGTAGCAGCAAAACCTGAAGCAGCTAAACCTGAAACAACAAAACCAG
TAGCAGCTAAACCTGAAGCAGCAAAACCAGTAGCAGCAAAACCAGTAGCAGCAAAA
CCAGTTGCTACTAATACTAATACTAATACTGGCTTTTCACTTACAAATAAACCAAAA
GAAGACTATTTCCCAATGGCTTTTAGTTATAAATTAGAATATACTGACGAAAATAAA
TTAAGCCTAAAAACACCGGAAATTAATGTATTTTTAGAACTAGTTCATCAAAGCGAG
TATGAAGAACAAAAAATAATAAAGGAACTAGATAAAACTGTTTTAAATCTTCAATAT
CAATTCCAGGAAGTCAAGGTAACTAGTGAACAATATCAGAAACTTAGCCACCCAAT
GATGACCGAGGGATCTCCTAATCAAGGTAAAAAAGCCGAAGGCGCTCCTAACCAAG
GCAAAAAAGCCGAAGGCGCACCTAGTCAAGGGAAAAAAGCCGAAGGCGCTCCTAAC
CAAGGCAAAAAAGCCGAAGGCGCACCTAGTCAAGGGAAAAAAGCAGAGGGTGCTT
CTAATCAACAAAGCACAACTACCGAATTAACTAATTACCTTCCTGAATTAGGTAAAA
AAATTGACGAAATCATTAAAAAACAAGGTAAAAATTGGAAAACAGAGGTTGAACTA
ATCGAGGATAATATCGCTGGAGATGCTAAATTGCTATACTTTGTCCTAAGGGATGAT
TCAAAATCCGGTGATCCTAAAAAATCAAGTCTAAAAGTTAAAATAACAGTAAAACA
AAGTAATAATAATCAGGAATTAAAATCTAAATAA

FIG. 11A

MEFGAFKSVLNSWTGKIQHPEKADIQRFTRHLEQVKLGSNSVLNQPQTTKEQVISSLKSN
NFFKNGHQVASYFQDLLTKDKLTVLETLYDLAKKWGLETNRAQFPKEVFQYTKDIFAE
ADKLKFLEGKKKDPYNQIKEIHQLSFNILARNDVIKSDGFYGVLLLPQSVKTELEGKNEA
QIFEALKKYSLIENSAFKTTILDKNLLEGTDFKTFGDFLKAFFLKAAQFNNFAPWAKLDD
NLQYSFEAIKKGETTKEGKREEVDKKVKELDNKIKGILPQPPAAKPEAAKPVAAKPEAA
KPETTKPVAAKPEAAKPVAAKPVAAKPVATNTNTNTGFSLTNKPKEDYFPMAFSYKLEY
TDENKLSLKTPEINVFLELVHQSEYEEQKIIKELDKTVLNLQYQFQEVKVTSEQYQKLSH
PMMTEGSPNQGKKAEGAPNQGKKAEGAPSQGKKAEGAPNQGKKAEGAPSQGKKAEG
ASNQQSTTTELTNYLPELGKKIDEIIKKQGKNWKTEVELIEDNIAGDAKLLYFVLRDDSK
SGDPKKSSLKVKITVKQSNNNQELKSK

FIG. 11B

SEQUENCE LISTING

```
<160> NUMBER OF SEQ ID NOS: 25

<210> SEQ ID NO 1
<211> LENGTH: 1108
<212> TYPE: PRT
<213> ORGANISM: Mycoplasma hyopneumoniae

<400> SEQUENCE: 1

Met Ser Lys Lys Ser Lys Thr Phe Lys Ile Gly Leu Thr Ala Gly Ile
1               5                   10                  15

Val Gly Leu Gly Val Phe Gly Leu Thr Val Gly Leu Ser Ser Leu Ala
            20                  25                  30

Lys Tyr Arg Ser Glu Ser Pro Arg Lys Ile Ala Asn Asp Phe Ala Ala
        35                  40                  45

Lys Val Ser Thr Leu Ala Phe Ser Pro Tyr Ala Phe Glu Thr Asp Ser
    50                  55                  60

Asp Tyr Lys Ile Val Lys Arg Trp Leu Val Asp Ser Asn Asn Asn Ile
65                  70                  75                  80

Arg Asn Lys Glu Lys Val Ile Asp Ser Phe Ser Phe Thr Lys Asn
                85                  90                  95

Gly Asp Gln Leu Glu Lys Ile Asn Phe Gln Asp Pro Glu Tyr Thr Lys
            100                 105                 110

Ala Lys Ile Thr Phe Glu Ile Leu Glu Ile Ile Pro Asp Asp Val Asn
        115                 120                 125

Gln Asn Phe Lys Val Lys Phe Gln Ala Leu Gln Lys Leu His Asn Gly
    130                 135                 140

Asp Ile Ala Lys Ser Asp Ile Tyr Glu Gln Thr Val Ala Phe Ala Lys
145                 150                 155                 160

Gln Ser Asn Leu Leu Val Ala Glu Phe Asn Phe Ser Leu Lys Lys Ile
```

```
                165                 170                 175
Thr Glu Lys Leu Asn Gln Gln Ile Glu Asn Leu Ser Thr Lys Ile Thr
            180                 185                 190
Asn Phe Ala Asp Glu Lys Thr Ser Ser Gln Lys Asp Pro Ser Thr Leu
        195                 200                 205
Arg Ala Ile Asp Phe Gln Tyr Asp Leu Asn Thr Ala Arg Asn Pro Glu
    210                 215                 220
Asp Leu Asp Ile Lys Leu Ala Asn Tyr Phe Pro Val Leu Lys Asn Leu
225                 230                 235                 240
Ile Asn Arg Leu Asn Asn Ala Pro Glu Asn Lys Leu Pro Asn Asn Leu
                245                 250                 255
Gly Asn Ile Phe Glu Phe Ser Phe Ala Lys Asp Ser Ser Thr Asn Gln
            260                 265                 270
Tyr Val Ser Ile Gln Asn Gln Ile Pro Ser Leu Phe Leu Lys Ala Asp
        275                 280                 285
Leu Ser Gln Ser Ala Arg Glu Ile Leu Ala Ser Pro Asp Glu Val Gln
    290                 295                 300
Pro Val Ile Asn Ile Leu Arg Leu Met Lys Lys Asp Asn Ser Ser Tyr
305                 310                 315                 320
Phe Leu Asn Phe Glu Asp Phe Val Asn Asn Leu Thr Leu Lys Asn Met
                325                 330                 335
Gln Lys Glu Asp Leu Asn Ala Lys Gly Gln Asn Leu Ser Ala Tyr Glu
            340                 345                 350
Phe Leu Ala Asp Ile Lys Ser Gly Phe Phe Pro Gly Asp Lys Arg Ser
        355                 360                 365
Ser His Thr Lys Ala Glu Ile Ser Asn Leu Leu Asn Lys Lys Glu Asn
    370                 375                 380
Ile Tyr Asp Phe Gly Lys Tyr Asn Gly Lys Phe Asn Asp Arg Leu Asn
385                 390                 395                 400
Ser Pro Asn Leu Glu Tyr Ser Leu Asp Ala Ala Ser Ala Ser Leu Asp
                405                 410                 415
Lys Lys Asp Lys Ser Ile Val Leu Ile Pro Tyr Arg Leu Glu Ile Lys
            420                 425                 430
Asp Lys Phe Phe Ala Asp Asp Leu Tyr Pro Asp Thr Lys Asp Asn Ile
        435                 440                 445
Leu Val Lys Glu Gly Ile Leu Lys Leu Thr Gly Phe Lys Lys Gly Ser
    450                 455                 460
Lys Ile Asp Leu Pro Asn Ile Asn Gln Gln Ile Phe Lys Thr Glu Tyr
465                 470                 475                 480
Leu Pro Phe Phe Glu Lys Gly Lys Glu Glu Gln Ala Lys Leu Asp Tyr
                485                 490                 495
Gly Asn Ile Leu Asn Pro Tyr Asn Thr Gln Leu Ala Lys Val Glu Val
            500                 505                 510
Glu Ala Leu Phe Lys Gly Asn Lys Asn Gln Glu Ile Tyr Gln Ala Leu
        515                 520                 525
Asp Gly Asn Tyr Ala Tyr Glu Phe Gly Ala Phe Lys Ser Val Leu Asn
    530                 535                 540
Ser Trp Thr Gly Lys Ile Gln His Pro Glu Lys Ala Asp Ile Gln Arg
545                 550                 555                 560
Phe Thr Arg His Leu Glu Gln Val Lys Ile Gly Ser Asn Ser Val Leu
                565                 570                 575
Asn Gln Pro Gln Thr Thr Lys Glu Gln Val Ile Ser Ser Leu Lys Ser
            580                 585                 590
```

```
Asn Asn Phe Phe Lys Asn Gly His Gln Val Ala Ser Tyr Phe Gln Asp
        595                 600                 605

Leu Leu Thr Lys Asp Lys Leu Thr Ile Leu Glu Thr Leu Tyr Asp Leu
610                 615                 620

Ala Lys Lys Trp Gly Leu Glu Thr Asn Arg Ala Gln Phe Pro Lys Gly
625                 630                 635                 640

Val Phe Gln Tyr Thr Lys Asp Ile Phe Ala Glu Ala Asp Lys Leu Lys
                645                 650                 655

Phe Leu Glu Leu Lys Lys Lys Asp Pro Tyr Asn Gln Ile Lys Glu Ile
            660                 665                 670

His Gln Leu Ser Phe Asn Ile Leu Ala Arg Asn Asp Val Ile Lys Ser
        675                 680                 685

Asp Gly Phe Tyr Gly Val Leu Leu Pro Gln Ser Val Lys Thr Glu
    690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
            740                 745                 750

Phe Phe Leu Lys Ala Ala Gln Phe Asn Asn Phe Ala Pro Trp Ala Lys
        755                 760                 765

Leu Asp Asp Asn Leu Gln Tyr Ser Phe Glu Ala Ile Lys Lys Gly Glu
770                 775                 780

Thr Thr Lys Glu Gly Lys Arg Glu Glu Val Asp Lys Val Lys Glu
785                 790                 795                 800

Leu Asp Asn Lys Ile Lys Gly Ile Leu Pro Gln Pro Ala Ala Lys
                805                 810                 815

Pro Glu Ala Ala Lys Pro Val Ala Ala Lys Pro Glu Thr Thr Lys Pro
            820                 825                 830

Val Ala Ala Lys Pro Glu Ala Ala Lys Pro Glu Ala Ala Lys Pro Val
        835                 840                 845

Ala Ala Lys Pro Glu Ala Ala Lys Pro Val Ala Ala Lys Pro Glu Ala
    850                 855                 860

Ala Lys Pro Val Ala Ala Lys Pro Glu Ala Ala Lys Pro Val Ala Ala
865                 870                 875                 880

Lys Pro Glu Ala Ala Lys Pro Val Ala Thr Asn Thr Gly Phe Ser Leu
                885                 890                 895

Thr Asn Lys Pro Lys Glu Asp Tyr Pro Met Ala Phe Ser Tyr Lys
            900                 905                 910

Leu Glu Tyr Thr Asp Glu Asn Lys Leu Ser Leu Lys Thr Pro Glu Ile
        915                 920                 925

Asn Val Phe Leu Glu Leu Val His Gln Ser Glu Tyr Glu Glu Gln Glu
    930                 935                 940

Ile Ile Lys Glu Leu Asp Lys Thr Val Leu Asn Leu Gln Tyr Gln Phe
945                 950                 955                 960

Gln Glu Val Lys Val Thr Ser Asp Gln Tyr Gln Lys Leu Ser His Pro
                965                 970                 975

Met Met Thr Glu Gly Ser Ser Asn Gln Gly Lys Lys Ser Glu Gly Thr
            980                 985                 990

Pro Asn Gln Gly Lys Lys Ala Glu  Gly Ala Pro Asn Gln  Gly Lys Lys
        995                 1000                 1005
```

-continued

```
Ala Glu  Gly Thr Pro Asn Gln  Gly Lys Lys Ala Glu  Gly Ala Pro
    1010                 1015                 1020

Ser Gln  Gln Ser Pro Thr Thr  Glu Leu Thr Asn Tyr  Leu Pro Asp
    1025                 1030                 1035

Leu Gly  Lys Lys Ile Asp Glu  Ile Ile Lys Lys Gln  Gly Lys Asn
    1040                 1045                 1050

Trp Lys  Thr Glu Val Glu Leu  Ile Glu Asp Asn Ile  Ala Gly Asp
    1055                 1060                 1065

Ala Lys  Leu Leu Tyr Phe Ile  Leu Arg Asp Asp Ser  Lys Ser Gly
    1070                 1075                 1080

Asp Pro  Lys Lys Ser Ser Leu  Lys Val Lys Ile Thr  Val Lys Gln
    1085                 1090                 1095

Ser Asn  Asn Asn Gln Glu Pro  Glu Ser Lys
    1100                 1105

<210> SEQ ID NO 2
<211> LENGTH: 1317
<212> TYPE: PRT
<213> ORGANISM: Mycoplasma hyopneumoniae

<400> SEQUENCE: 2

Met Ala Lys Asn Asn Lys Asn Ser Leu Leu Val Thr Ala Thr Ala Ile
1               5                   10                  15

Val Gly Val Ala Val Phe Ala Thr Thr Val Gly Leu Val Thr Arg Ile
            20                  25                  30

Arg Tyr Lys Gly Glu Asn Pro Arg Ala Glu Leu Glu Ser Leu Val Ser
        35                  40                  45

Lys Val Gln Asn Val Ala Phe Lys Ser Asp Val Phe Asp Asn Ser Thr
    50                  55                  60

Thr Tyr Lys Gln Ile Lys Ala Leu Leu Phe Asp Glu Thr Gly Lys Leu
65                  70                  75                  80

Arg Pro Gly Ile Asp Leu Asn Lys Phe Ile Ser Phe Tyr Thr Ala Val
                85                  90                  95

Asn Ser Lys Ile Gln Lys Phe Glu Val Ser Phe Ala Pro Asn Lys Pro
            100                 105                 110

Phe Phe Glu Phe Ile Asn Leu Ile Pro Asp Asp Lys Asn Gln Thr Phe
        115                 120                 125

Thr Leu Gln Phe Arg Ala Lys His Gln Leu Asp Asn Asn Tyr Thr Ala
    130                 135                 140

Tyr Ser Ser Ile Leu Ser Lys Lys Ile Ala Tyr Ala Gln Arg Ser Gln
145                 150                 155                 160

Phe Ala Leu Ala Asp Phe Asn Ala Asn His Arg Lys Ile Thr Lys Ser
                165                 170                 175

Phe Gln Thr Asn Ile Gln Asn Leu Arg Glu Thr Asp Phe Ser Val Asp
            180                 185                 190

Phe Ser Ser Ser Gln Thr Ser Leu Ala Ser Gln Lys Ile Pro Phe Leu
        195                 200                 205

Thr Arg Val Glu Asp Phe Ala Ala Asp Ile Asn Lys Ser Gly Asn Gln
    210                 215                 220

Glu Glu Ala Ile Ser Arg Ile Ser Lys Tyr Phe Pro Asp Phe Gln Arg
225                 230                 235                 240

Tyr Ile His Glu Leu Lys Asp Asp Pro Asn Asn Val Leu Pro Phe Lys
                245                 250                 255

Lys Gly Lys Ile Phe Asp Phe Ser Ile Thr Arg Arg Ala Gly Thr Asn
            260                 265                 270
```

```
Asp Phe Ile Ser Leu Ser Ala Asn Ser Glu Pro Ser Phe Leu Ile Lys
        275                 280                 285

Ala Arg Leu Thr Asn Glu Ala Lys Phe Glu Leu Arg Gly Leu Asn Ile
    290                 295                 300

Glu Glu Ala Glu Met Leu Glu Glu Ile Lys Leu Val Pro Val Asp Gln
305                 310                 315                 320

Phe Val Val Asn Leu Glu Thr Asp Leu Lys Pro Gly Gln Ala Pro Glu
                325                 330                 335

Lys Ser Gln Lys Pro Gln Ser Glu Gln Thr Glu Ile Lys Lys Thr Tyr
                340                 345                 350

Phe Ala Glu Ile Asp Lys Ile Leu Ser Lys Ile Thr Met Arg Lys Leu
                355                 360                 365

Gln Leu Ser Asp Phe Lys Val Ala Pro Gln Thr Ser Ser Ser Gln Pro
    370                 375                 380

Lys Gln Val Lys Ala Ser Val Ser Ala Trp Ser Asn Leu Asp Gln Gly
385                 390                 395                 400

Gln Glu Asn Arg Ile Leu Val Pro Val Ser Gln Ser Ser Asn Pro
                405                 410                 415

Gln Gln His Gln Gln Gln Pro Gln Pro Gly Ser Gln Pro Gln Pro
                420                 425                 430

Gln Pro Gln Ser Gln Pro Gln Ser Gln Pro Gln Pro Asn Ala Gln Thr
                435                 440                 445

Gln Pro Lys Ala Gln Ala Gln Ser Ser Pro Lys Ala Pro Val Gln Lys
    450                 455                 460

Pro Ala Thr Pro Asp Pro Ser Lys Ser Phe Lys Ile Arg Thr Lys Arg
465                 470                 475                 480

Ala Arg Asp Phe Leu Lys Glu Phe Asn Lys Thr Phe Tyr Arg Ser Asn
                485                 490                 495

Lys Leu Lys Ser Gln Lys Leu Glu Glu Lys Ile Asn Ser Glu Tyr Leu
                500                 505                 510

Ser Asn Lys Ile Gly Ile Asp Leu Gly Val Leu Lys Lys Tyr Ile Asn
                515                 520                 525

Asn Asn Gln Gly Ile Glu Tyr Thr Phe Asp Ile Ala Asn Ala Lys Ile
    530                 535                 540

Arg Asp Ala Gln Asp Gly Ile Thr Ser His Ile Glu Ile Pro Val Thr
545                 550                 555                 560

Ile Ser Leu Trp Ser Ser Phe Phe Gly Asp Ser Asp Asn Val Leu Leu
                565                 570                 575

Lys Ser Lys Thr Glu Thr Phe Ile Ile Pro Tyr Phe Gln Lys Glu Thr
                580                 585                 590

Thr Ser Glu Ser Lys Asp Gln Lys Val Gly His Thr Gln Lys Glu Leu
                595                 600                 605

Asp Leu Asn Gln Lys Leu Ile Tyr Gln Leu Ser Glu Leu Pro Gly Thr
    610                 615                 620

Ser Ala Gln Gly Ser Ser Gly Ser Ser Ala Gln Thr Glu Gln Ile Lys
625                 630                 635                 640

Glu Val Lys Leu Pro Thr Leu Thr Ala Phe Ile Ser Lys Gln Glu Leu
                645                 650                 655

Glu Ala Leu Ile Asp Gly Asp Lys Asn Leu Ala Ser Gln Pro Thr Ser
                660                 665                 670

Gln Ala Val Ser Val Ser Gln Glu Val Lys Thr Thr Glu Phe Gln Gln
                675                 680                 685
```

-continued

Gln Glu Ala Asn Ser Thr Asn Ser Ser Pro Ser Ser Pro Ser Pro Ser
690                 695                 700

Pro Thr Ser Pro Ser Pro Ala Ser Pro Ser Ser Ser Pro Ser Pro Thr
705                 710                 715                 720

Ser Pro Lys Asn Leu Asp Glu Asn Ile Gly Val Pro Asn Pro Arg Phe
            725                 730                 735

Glu Glu Ile Lys Lys Ile Ile Ser Ser Glu Phe Thr Tyr Lys Tyr Asn
            740                 745                 750

Phe Arg Ala Asn Glu Ala Leu Leu Asp Ala Trp Val Gly Lys Gln Asn
            755                 760                 765

Phe Pro Ser Leu Lys Asp Ile Ser Gln Phe Arg Ser Asp Gln Arg Leu
770                 775                 780

Ala Lys Asp Tyr Lys Leu Val Asn Leu Lys Ser Asn Lys Phe Leu Lys
785                 790                 795                 800

Glu Asp Tyr Asp Val Leu Ala Phe Tyr Ala Asn Leu Val Gln Lys Asp
                805                 810                 815

Pro Arg Glu Val Leu Gln Tyr Leu Phe Glu Ile Ala Lys Ala Asn Asn
            820                 825                 830

Leu Ile Gly Pro Glu Glu Lys Leu Asp Leu Asn Gln Ile Glu Asp Asp
            835                 840                 845

Gly Ile Phe Arg Arg Ala Lys Ala Ile Lys Leu Ile Asp Lys Ser Ser
850                 855                 860

Asn Asn Gln Gly Ile Tyr Gly Phe Ser Phe Asn Asn Gln Phe Leu Lys
865                 870                 875                 880

Phe His Glu Arg Gly Trp Met Ser Thr Leu Tyr Leu Pro Asn Glu Ala
                885                 890                 895

Lys Thr Lys Leu Ala Asp Tyr Gln Asn Leu Leu Ser Ala Gly Ile Ser
            900                 905                 910

Asp Thr Lys Ile Phe Ser Glu Leu Asn Lys Ile Gln Pro Leu Asp Leu
            915                 920                 925

Asn Ile Lys Val Gln Ser Ser Asp Ser Ser Asp Ser Lys Ser Asp Ser
            930                 935                 940

Ser Asp Ser Ser Asp Ala Lys Thr Thr Ser Thr Lys Gln Asp Leu Leu
945                 950                 955                 960

Ser Lys Leu Thr Ser Leu Lys Ser Gln Ile Glu Ala Ile Val Lys Lys
                965                 970                 975

Tyr Glu Thr Glu Ser Lys Asn Tyr Leu Gly Thr Glu Asn Asn Asn Ser
            980                 985                 990

Ser Ser Ser Ser Gly Thr Glu Gln Lys Gly Ser Ser Ile Pro Glu Glu
            995                 1000                1005

Asn Lys Lys Phe Ile Leu Glu Asn Thr Ala Lys Leu Asp Asn Leu
    1010                1015                1020

Ala Asp Leu Leu Leu Ala Phe Tyr Tyr Gln Ala Lys Arg Leu Asn
    1025                1030                1035

Phe Ala Ser Trp Ser Gln Leu Gln Asp Glu Asp Leu Asp Tyr Gln
    1040                1045                1050

Ile Gln Phe Glu Lys Glu Ala Asn Asn Thr Glu Ser Ser Ser Ser
    1055                1060                1065

Ser Ser Ser Ser Ser Ser Ser Ser Ser Ser Ser Ser Ser Ser Ser
    1070                1075                1080

Ser Ser Glu Thr Asp Thr Asn Lys Pro Glu Asn Ala Val Glu Tyr
    1085                1090                1095

Lys Leu Thr Tyr Tyr Tyr Lys Ile Tyr Asn Lys Thr Thr Lys Lys

-continued

```
    1100                1105                1110

Val Val  Tyr Thr Thr Pro Lys  Thr Ile Ile Lys Leu  Tyr Leu Ala
    1115                1120                1125

Ser Ser  Asn Ile Gly Val Lys  Glu Lys Gln Glu Arg  Glu Leu Met
    1130                1135                1140

Asn Lys  Leu Val Leu Ser Ile  Pro Ser Ala Tyr Ser  Ile Phe Tyr
    1145                1150                1155

Leu Lys  Gln Ser Glu Trp Glu  Gln Val Lys Thr Asn  Asn Gly Gln
    1160                1165                1170

Gln Met  Gly Gln Thr Gly Ser  Ser Gln Gly Phe Glu  Ser Leu Glu
    1175                1180                1185

Pro Phe  Lys Lys Ile Gln Glu  Ile Val His Lys Asn  Asn Lys Asp
    1190                1195                1200

Tyr Asp  Leu Lys Val Val Thr  Ile Arg Asp Asp Ala  Tyr Ala Glu
    1205                1210                1215

Asn Ala  Lys Ile Val His Leu  Arg Val Val Arg Lys  Glu Glu Gln
    1220                1225                1230

Gln Ala  Glu Gln Lys Glu Lys  Glu Lys Glu Lys Glu  Lys Glu Lys
    1235                1240                1245

Glu Gln  Lys Glu Thr Ser Ser  Gln Gly Gln Val Pro  Gln Ser Ala
    1250                1255                1260

Phe Phe  Phe Gln Val Arg Leu  Ile Lys Asp Asp Tyr  Gln Gly Ala
    1265                1270                1275

Glu Ala  Ser Asn Gln Gln Thr  Ser Arg Gln Ala Met  Gln Met Pro
    1280                1285                1290

Asn Met  Glu Ser Gln Asn Ser  Gly Ser Ser Ser Ser  Ala Pro Ala
    1295                1300                1305

Ala Ala  Ala Ala Ala Lys Ala  Ala Arg
    1310                1315

<210> SEQ ID NO 3
<211> LENGTH: 904
<212> TYPE: PRT
<213> ORGANISM: Mycoplasma hyopneumoniae

<400> SEQUENCE: 3

Met Lys Leu Ala Lys Leu Leu Lys Lys Pro Phe Trp Leu Ile Thr Thr
1               5                   10                  15

Ile Ala Gly Ile Ser Leu Ser Leu Ser Ala Ala Val Gly Thr Val Val
            20                  25                  30

Gly Ile Asn Ser Tyr Asn Lys Ser Tyr Tyr Ser Tyr Leu Asn Gln Ile
        35                  40                  45

Pro Ser Gln Leu Lys Val Ala Lys Asn Ala Lys Ile Ser Gln Glu Lys
    50                  55                  60

Phe Asp Ser Ile Val Leu Asn Leu Lys Ile Lys Asp Asn Phe Lys Lys
65                  70                  75                  80

Trp Ser Ala Lys Thr Val Leu Thr Ala Ala Lys Ser Asp Leu Tyr Arg
                85                  90                  95

Tyr Asn Leu Val Ser Ala Phe Asp Leu Ser Glu Leu Ile Asn Asn Asp
            100                 105                 110

Tyr Leu Val Ser Phe Asp Leu Glu Asn Ala Val Val Asp Gln Asn Ser
        115                 120                 125

Ile Lys Asn Val Val Ile Tyr Ala Lys Ser Asp Lys Asp Gln Ile Thr
    130                 135                 140
```

```
Tyr Ser Lys Gln Ile Val Leu Lys Gly Phe Gly Asn Thr Glu Gln Ala
145                 150                 155                 160

Arg Thr Asn Phe Asp Phe Ser Gln Ile Asp Ser Ser Lys Ser Phe Val
            165                 170                 175

Asp Leu Ser Arg Ala Asn Leu Thr Leu Met Glu Phe Gln Ile Leu Leu
        180                 185                 190

Ala Gln Asn Phe Glu Asn Glu Arg Gly Ser Asn Trp Phe Ser Arg Leu
    195                 200                 205

Glu Arg Ala Leu Val Ala Ser Lys Ala Ser Leu Ser Leu Tyr Asn Ser
210                 215                 220

Leu Gly Glu Pro Val Phe Leu Gly Pro Asp Tyr Gln Leu Asp Pro Val
225                 230                 235                 240

Leu Asp Arg Lys Lys Leu Leu Thr Leu Leu Asn Lys Asp Gly Lys Leu
            245                 250                 255

Val Leu Gly Leu Asn Leu Val Gln Ile Ser Thr Lys Lys Thr Met Asn
        260                 265                 270

Leu Asn Leu Glu Val Arg Gly Ala Ile Ser Asn Gln Glu Ile Ser Lys
    275                 280                 285

Ile Leu Lys Ser Trp Leu Glu Thr Asn Leu Gln Gly Lys Leu Lys Thr
290                 295                 300

Lys Asp Asp Leu Gln Met Ala Leu Val Lys Asp Lys Ile Ser Leu Ser
305                 310                 315                 320

Asp Tyr Trp Tyr Gly Ser Pro Asn Ser Lys Val Asn Thr Ser Gln Ile
            325                 330                 335

Leu Thr Lys Ser Lys Glu Phe Lys Asp Leu Phe Asp Leu Ser Glu Thr
        340                 345                 350

Asn Phe Phe Leu Asn Thr Lys Ile Gly Thr Val Tyr Leu Ser Ile Ile
    355                 360                 365

Pro Lys Leu Leu Asp Pro Ser Gln Ile Ser Val Val Asp Lys Lys Lys
370                 375                 380

Leu Val Glu Asn Gln Lys Ile Arg Phe Glu Ile Thr Ala Ser Leu Lys
385                 390                 395                 400

Arg Lys Ala Ile Asp Lys Lys Phe Ile Ile Gln Asp Leu Pro Val Phe
            405                 410                 415

Val Asp Leu Lys Val Asp Phe Asn Lys Tyr Gln Ala Ala Val Ala Gln
        420                 425                 430

Met Phe Gly Thr Ile Lys Ala Val Lys Glu Phe Ser Met Pro Glu Asp
    435                 440                 445

Gln Asp Ala Lys Thr Leu Ser Ser Asn Glu Ile Lys Gln Arg Val Asp
450                 455                 460

Arg Leu Phe Glu Leu Ala Lys Thr Val Thr Asn Leu Glu Asn Pro Ser
465                 470                 475                 480

Glu Glu Val Leu Lys Ser Ile Tyr Leu Leu Asn Thr Gly Lys Tyr Leu
            485                 490                 495

Val Asp Gln Asp Gln Glu Lys Val Lys Gln Glu Leu Lys Thr Val Ile
        500                 505                 510

Glu Gly Leu Lys Ser Lys Ala Asn Thr Gln Lys Thr Glu Lys Asn Ser
    515                 520                 525

Pro Thr Gln Pro Lys Lys Pro Glu Val Ser Leu Ala Lys Thr Thr Glu
530                 535                 540

Asn Ser Ala Lys Thr Val Lys Val Ser Thr Phe Ala Glu Glu Ala Lys
545                 550                 555                 560

Gly Gln Ser Gln Ser Gln Gln Thr Gln Pro Val Ser Thr Ser Ser Pro
```

-continued 565 570 575

Gln Thr Ser Gln Asn Ser Leu Pro Asn Ser Thr Ser Ser Ser Asn Ser
580 585 590

Val Leu Glu Asn Glu Lys Phe Gly Thr Ser Ile Trp Thr Ala Phe Asn
595 600 605

Phe Ala Asn Ile Tyr Asn Leu Glu Asn Thr Lys Ser Glu Tyr Glu Ile
610 615 620

Ser Thr Leu Gly Asn Lys Leu Phe Phe Asp Phe Lys Leu Val Asp Lys
625 630 635 640

Thr Asn Gln Asn Leu Ile Leu Ala Gln Ser Lys Ile Ser Leu Asn Asn
645 650 655

Ile Ile Asn Ser Asn Lys Ser Ala Tyr Asp Ile Ile Lys Lys Phe Asn
660 665 670

Pro Asp Val Phe Leu Asp Gly Thr Ile Asn Tyr Gln Asn Gln Gly Lys
675 680 685

Asp Lys Lys Glu Phe Ile Leu Lys Asp Leu Ser Asp Asn Lys Leu Ile
690 695 700

Phe Lys Ser Glu Asp Ala Ile Gln Thr Asp Gln Gly Leu Glu Leu Lys
705 710 715 720

Lys Pro Leu Lys Leu Gln Ser Lys Ser Ser Asn Pro Glu Lys Glu Ile
725 730 735

Ser Thr Ser Leu Tyr Thr Gly Ala Ile Tyr Leu Val Phe Asp Ala Lys
740 745 750

Asn Ile Ser Asp Gly Asn Trp Ile Asn Leu Leu Ala Asp Arg Lys Gly
755 760 765

Lys Gly Leu Val Ile Lys Val Gln Asn Ser Asn Asn Asn Val Pro Lys
770 775 780

Thr Lys Glu Ile Val Glu Asn Gly Thr Tyr Leu Tyr Glu Ile Leu Ala
785 790 795 800

Gly Lys Asp Ser Ile Lys Val Asn Ser Tyr Phe Phe Pro Thr Lys Tyr
805 810 815

Pro Lys Arg Val Lys Arg Leu Lys Phe Glu Ile Asn Pro Lys Asp Thr
820 825 830

Leu Pro Asn Phe Phe Thr Leu Glu Trp Phe His Leu Asp Trp Tyr Gln
835 840 845

Ile Gly Pro Gly Glu Gln Asn Lys Lys Pro Gln Gln Asn Ala Lys Lys
850 855 860

Glu Pro Thr Ile Ile Leu Lys Thr Leu Ala Ile Phe Asn Asp Lys Ser
865 870 875 880

Phe Ala Glu Lys Gly Ser Leu Thr Lys Arg Ser Glu Leu Ile Asn Gly
885 890 895

Leu Ile Arg Asn Tyr Val Lys Lys
900

<210> SEQ ID NO 4
<211> LENGTH: 1052
<212> TYPE: PRT
<213> ORGANISM: Mycoplasma hyopneumoniae

<400> SEQUENCE: 4

Met Ser Lys Leu Thr Lys Ser Lys Thr Phe Lys Ile Gly Leu Val Gly
1 5 10 15

Ser Ile Ile Gly Leu Gly Val Phe Gly Leu Thr Val Gly Leu Ser Ser
20 25 30

```
Leu Ala Lys Tyr Arg Ser Glu His Pro Arg Lys Val Asn Asp Phe
        35                  40                  45
Ala Thr Lys Val Ser Thr Leu Ser Phe Ser Pro Asp Ala Phe Phe Ala
 50                  55                  60
Asn Ser Asp Tyr Trp Thr Ile Lys Asn His Leu Leu Asp Ser Lys Asn
 65                  70                  75                  80
Gln Ile Lys Asn Ser Glu Lys Val Leu Lys Ser Phe Ser Phe Phe Ser
                 85                  90                  95
Lys Asn Gly Asp Gln Leu Glu Lys Ile Asn Leu Glu Asp Pro Glu Tyr
                100                 105                 110
Lys Asn Ala Gly Ile Ser Phe His Ile Leu Glu Ile Ile Pro Asp Asp
                115                 120                 125
Val Asn Gln Asn Phe Lys Val Lys Phe Gln Leu Trp Gln Lys Phe Ala
130                 135                 140
Asn Gly Asp Ile Ala Lys Ser Asp Ile Tyr Gln Glu Glu Ser Val Ala
145                 150                 155                 160
Phe Ile Lys Gln Ser Asn Leu Leu Val Ala Glu Phe Asn Phe Ser Leu
                165                 170                 175
Lys Lys Ile Thr Asp Lys Leu Asn Gln Gln Val Gly Asn Leu Ser Leu
                180                 185                 190
Lys Ser Thr Asn Phe Ala Asp Asp Leu Ala Lys Leu Thr Lys Pro Thr
                195                 200                 205
Ser Ser Tyr Lys Asn Pro Ala Ser Phe Arg Val Leu Asp Phe Gln Glu
                210                 215                 220
Asp Leu Asn Gln Ala Arg Asn Ser Glu Glu Leu Val Lys Lys Leu Ala
225                 230                 235                 240
Ile Tyr Phe Pro Ser Leu Asp Asn Leu Ile Thr Lys Leu Asn Glu Ser
                245                 250                 255
Ser Glu Asn Lys Leu Pro Gly Asn Ser Gly His Ile Phe Glu Phe Ser
                260                 265                 270
Leu Arg Lys Ser Gln Ala Thr Asn Gln Tyr Val Ser Val Gln Asn Gln
                275                 280                 285
Ile Pro Phe Leu Phe Leu Glu Ala Asp Leu Ser Gln Ser Ala Arg Asp
                290                 295                 300
Leu Ile Gly Gln Asp Phe Asn Phe Arg Pro Ile Val Ser Ser Ile Lys
305                 310                 315                 320
Leu Gln Lys Gln Asp Asn Ser Ser Tyr Phe Leu Asp Phe Asn Gln Phe
                325                 330                 335
Leu Gly Asn Leu Lys Leu Lys Asp Ile Ser Lys Thr Asp Phe Asn Glu
                340                 345                 350
Gln Gly Leu Lys Thr Ser Ala Tyr Glu Ile Leu Ser Thr Ile Arg Ser
                355                 360                 365
Gly Phe Phe Asp Asn Asn Asp Leu Arg Ser Asp Gln Ala Lys Glu Ser
                370                 375                 380
Ile Asn Lys Ile Leu Lys Asn Lys Ile Lys Phe Asp Phe Gly Lys Leu
385                 390                 395                 400
Asp Ala Ile Phe Ser Asp Lys Gly Asn Ser Glu Ser Leu Gln Tyr Tyr
                405                 410                 415
Leu Asp Val Lys Lys Ala Ser Leu Asp Lys Thr Asp Lys Ser Thr Ile
                420                 425                 430
Leu Ile Pro Phe Arg Leu Lys Val Asp Glu Ser Phe Phe Lys Thr Ser
                435                 440                 445
Thr Asn Leu Pro Glu Asn Ile Ile Ala Arg Lys Asp Gly Ile Phe Lys
```

```
            450                 455                 460
Leu Thr Gly Phe Asp Gln Gly Leu Asn Asn Gln Leu Pro Lys Ile Asn
465                 470                 475                 480

Gln Glu Ile Tyr Lys Thr Lys Tyr Leu Ser Phe Phe Glu Lys Gly Lys
                    485                 490                 495

Glu Asn Gln Asp Leu Val Asp Phe Gly Ser Glu Pro Ile Asn Gly Pro
                500                 505                 510

Leu Leu Ile Ser Lys Val Glu Ala Asp Ala Leu Phe Lys Glu Asn Lys
                515                 520                 525

Pro Glu Ala Ile His Lys Val Leu Glu Thr Asn Tyr Asn Tyr Gln Phe
530                 535                 540

Asn Pro Tyr Gln Ser Leu Leu Asp Ser Trp Thr Gly Asn Leu Val Gln
545                 550                 555                 560

Pro Lys Leu Glu Asn Ile Lys Ala Leu Asn Glu Asn Glu Lys Ala Ala
                565                 570                 575

Val Ser Glu Ala Gly Ile Ala Glu Ile Leu Ser Arg Asp Phe Phe Leu
                580                 585                 590

Asp Gly His Gln Val Ala Ser Phe Tyr Gln Asp Leu Leu Thr Lys Asp
                595                 600                 605

Arg Leu Thr Val Ile Glu Thr Leu Tyr Glu Leu Gly Lys Lys Trp Gly
610                 615                 620

Leu His Thr Asn Thr Ala Asn Phe Pro Arg Trp Lys Phe Arg Asn Ala
625                 630                 635                 640

Lys Asn Ile Phe Glu Glu Ala Thr Gln Tyr Lys Phe Leu Leu Gly Lys
                645                 650                 655

Lys Gly Lys Glu Asn Phe Arg Lys Ile Thr Lys Leu Thr Phe Asn Gly
                660                 665                 670

Leu Tyr Arg Asn Glu Lys Gly Gln Gly Phe Tyr Ala Thr Leu Val Leu
                675                 680                 685

Pro Lys Glu Ile Lys Asp Lys Leu Ala Asn Lys Thr Asp Ala Glu Val
690                 695                 700

Phe Ala Glu Leu Lys Lys His Ser Leu Ile Asp Ser Ser Gly Phe Lys
705                 710                 715                 720

Thr Ile Asn Ile Asp Lys Asn Leu Leu Glu Gly Asp Phe Glu Asn
                725                 730                 735

Phe Gly Asp Leu Leu Lys Ala Phe Phe Leu Lys Ala Ala Gln Phe Asn
                740                 745                 750

Asn Phe Ala Pro Trp Ala Lys Leu Asp Asp Asn Leu Lys Tyr Ser Phe
                755                 760                 765

Val Pro Lys Lys Gly Asp Gln Glu Lys Glu Gly Lys Lys Ala Glu Ile
770                 775                 780

Asp Lys Lys Val Lys Glu Leu Thr Asp Lys Ile Ser Ser Pro Gly Ser
785                 790                 795                 800

Val Leu Pro Lys Ser Glu Ala Gly Lys Pro Val Ala Ala Lys Pro Glu
                805                 810                 815

Ala Ala Lys Pro Ser Ser Ser Thr Thr Ser Ser Val Ser Ser Ala Ser
                820                 825                 830

Leu Glu Gly Asn Tyr Leu Pro Ile Ser Phe Glu Phe Lys Leu Ser Tyr
                835                 840                 845

Arg Asp Gly Ala Lys Ser Glu Leu Lys Thr Pro Glu Ile Lys Val Phe
850                 855                 860

Leu Glu Leu Gln Thr Asp Lys Asp Tyr Gln Glu Asn Lys Ile Ile Lys
865                 870                 875                 880
```

-continued

```
Glu Leu Asp Lys Thr Val Leu Glu Leu Gln Ser Glu Phe Lys Glu Trp
                885                 890                 895

Arg Leu Asp Glu Ser Ala Phe Ser Ser Leu Thr Phe Pro Lys Ser Gln
            900                 905                 910

Lys Ser Glu Gly Thr Gln Asn Gln Gly Lys Lys Ala Glu Gly Ala Pro
        915                 920                 925

Asn Gln Ser Lys Lys Ser Glu Glu Asn Ser Asn Lys Leu Thr Glu Tyr
    930                 935                 940

Ile Gln Glu Leu Gly Thr Lys Val Glu Lys Ser Leu Lys Ser Lys Gly
945                 950                 955                 960

Lys Asn Tyr Ser Ala Glu Val Glu Lys Ile Ile Glu Ala Phe Ser Gly
                965                 970                 975

Gly Tyr Lys Phe Leu Asp Phe Ala Leu Val Glu Gln Thr Pro Lys Pro
            980                 985                 990

Glu Thr Pro Lys Thr Glu Ala Ala  Lys Pro Glu Thr Thr  Lys Pro Val
        995                 1000                1005

Ala Ala  Arg Pro Glu Ala Ala  Lys Val Ala Ala Lys  Pro Ser Ala
    1010                 1015                 1020

Ala Lys  Pro Val Ser Ser Pro  Ala Pro Lys Lys Ser  Thr Leu Tyr
    1025                 1030                 1035

Val Arg  Val Leu Ile Arg Lys  Lys Glu Asn Lys Gln  Val Lys
    1040                 1045                 1050

<210> SEQ ID NO 5
<211> LENGTH: 1410
<212> TYPE: PRT
<213> ORGANISM: Mycoplasma hyopneumoniae

<400> SEQUENCE: 5

Met Lys Lys Gln Ile Arg Asn Lys Ala Ile Ile Val Leu Ala Gly Leu
1               5                   10                  15

Ser Phe Ile Gly Ile Thr Ala Gly Val Gly Leu Ala Val Gln Asn Ser
            20                  25                  30

Ala Leu Arg Ser Ser Tyr Leu Asn Gln Phe Lys Asn Asp Lys Ser Ala
        35                  40                  45

Thr Glu Leu Leu Ser Pro Ile Asn Asp Thr Glu Leu Ser Lys Ile Ile
    50                  55                  60

Ser Asn Phe Ser Leu Lys Glu Asn Trp Ser Lys Ile Ser Ala Gly Gln
65                  70                  75                  80

Ala Phe Glu Leu His Lys Asn Pro Leu Tyr Ala Phe Lys Leu Thr Asp
                85                  90                  95

Ala Ile Asp Phe Ser Lys Ile Asp Lys Lys Phe Ala His Leu Phe Phe
            100                 105                 110

Asn Val Gln Val Asn Asp Asn Thr Lys Val Glu Gly Asn Ser Ile Arg
        115                 120                 125

Asn Leu Thr Val Phe Val Phe Asp Ala Ile Thr Lys Lys Glu Val Ala
    130                 135                 140

Thr Arg Ala Phe His Thr Ser Leu Ser Gly Phe Ser Ser Val Ala Lys
145                 150                 155                 160

Glu Asp Phe Ile Glu Asn Phe Val Ala Glu Ser Ser Thr Tyr Glu Leu
                165                 170                 175

Asp Lys Asp Gln Leu Lys Lys Asn Phe Ala Thr Glu Ile Val Leu Pro
            180                 185                 190

Ser Ala Phe Ser Ile Lys Phe Gln Asp Val Leu Leu Thr His Leu Arg
```

```
            195                 200                 205
Lys Thr Ser Pro Glu Ser Phe Gln Glu Thr Lys Thr Ile Gln Val Arg
210                 215                 220

Ala Leu Thr Asn Ser Ile Thr Glu Phe Gln Gln Gln Gln Gln Glu Gly
225                 230                 235                 240

Gly Ser Gly Gly Ser Gly Thr Ser Gly Ser Ser Gly Gly Ser Ser
                245                 250                 255

Ser Gly Ser Thr Asp Gln Lys Gly Gln Thr Ser Gln Ser Ser Glu Lys
            260                 265                 270

Glu Ser Lys Ser Glu Lys Glu Lys Gly Lys Asp Gln Gln Ser Thr Gln
        275                 280                 285

Gly Ser Glu Gln Lys Gln Asp Gln Lys Gln Gln Lys Pro Lys Glu Ala
    290                 295                 300

Glu Lys Pro Ala Gln Glu Lys Pro Ala Gln Glu Lys Pro Ala Glu Thr
305                 310                 315                 320

Pro Lys Val Lys Ala Pro Val Ile Glu Pro Val Lys Lys Leu Val Phe
                325                 330                 335

Glu Asn Glu Lys Leu Asn Gln Ala Leu Leu Glu Thr Leu Lys Asp Phe
            340                 345                 350

Gly Gly Leu Lys Leu Leu Ala Ala Ser Gly Leu Gln Gly Leu Leu Pro
        355                 360                 365

Asn Glu Tyr Thr Leu Leu Pro Val Ser Ser Asp Lys Ser Leu Ile Lys
    370                 375                 380

Leu Asp Ile Asp Asp Gln Ala Gly Thr Ala Ser Ile His Leu Lys Leu
385                 390                 395                 400

Leu Asp Lys Asn Lys Lys Glu Lys Asn Leu Ile Leu Pro Ile Asn Gly
                405                 410                 415

Leu Ala Ser Ile Gly Ala Ile Lys Asp Lys Val Phe Ser Gln Ile Phe
            420                 425                 430

Arg Asn Gln Asn Ala Tyr Leu Thr Ile Arg Pro Gln Ile Asn Glu Tyr
        435                 440                 445

Leu Arg Lys Asn Pro Arg Lys Lys Ile Gln Glu Val Ile Trp Ser Phe
    450                 455                 460

Ser Arg Glu Lys Phe Asp Gln Leu Arg Gly Gln Asn Glu Val Glu Lys
465                 470                 475                 480

Phe Leu Glu Glu Leu Tyr Asn Pro Thr Gln Thr Ser Gln Ser Pro Gln
                485                 490                 495

Lys Ser Lys Ser Ser Asp Ser Ala Lys Asn Asn Val Ala Thr Ile Gln
            500                 505                 510

Ala Ser Pro Glu Thr Ala Pro Lys Thr Thr Thr Asn Ser Asn Thr
        515                 520                 525

Gln Ser Ser Ser Thr Ser Asn Asn Gln Ser Ser Asn Gly Ser Gln
    530                 535                 540

Gln Met Ala Ser Pro Gln Thr Glu Ser Ser Leu Ser Thr Ala Lys Thr
545                 550                 555                 560

Ser Glu Ala Ser Asn Ser Ser Glu Glu Ser Ser Glu Thr Lys Gly
                565                 570                 575

Thr Lys Glu Gln Ala Asn Ser Glu Thr Asn Pro Met Gly Lys Ser Gln
            580                 585                 590

Ala Lys Pro Glu Ala Lys Pro Glu Glu Lys Gln Ile Asn Leu Glu Asp
        595                 600                 605

Gln Ala Lys Thr Glu Leu Lys Glu Ile Leu Lys Ile His Gly Trp Asn
    610                 615                 620
```

```
Tyr Arg Thr Leu Leu Lys Asp Gln Asn Gln Lys Val Ile Leu Pro Asp
625                 630                 635                 640

Asn Ile Asn Phe Trp Phe Asp Leu Arg Asn Lys Arg Ser Ser Tyr Glu
                645                 650                 655

Asn Tyr Lys Leu Glu Phe Asp Leu Val Lys Lys Thr Gly Gln Ile Gln
                660                 665                 670

Ala Gly Asp Val Ile Asp Ala Asn Lys Ile Arg Leu Asn Leu Lys Ile
            675                 680                 685

Ser Pro Leu Ala Asn Leu Lys Leu Glu Val Asp Ser Lys Asn Lys Gln
690                 695                 700

Tyr Ile Asp Ala Gly Gln Ile Gly Asp Tyr Val Glu Phe Asp Lys Gln
705                 710                 715                 720

Gly Lys Lys Leu Val Glu Gln Gly Lys Ser Leu Asp Leu Lys Val Gly
                725                 730                 735

Ala Ser Ala Ala Asn Ser Ile Phe Ser Pro Glu Ile Arg Tyr Ser Ala
                740                 745                 750

Tyr Glu Leu Lys Gly Trp Thr Tyr Pro Ile Asp Ile Asp Ile Lys Gly
            755                 760                 765

Asn Pro Ile Gln Gln Glu Leu Glu Lys Leu Val Gly Asn Phe His Lys
770                 775                 780

Val Gly Ile Asn Lys Asn Asn Gln Tyr Gln Ile Tyr Ser Thr Asp Ile
785                 790                 795                 800

Asp Lys Ile Phe Ala Gln Ala Lys Leu Asp Lys Tyr Phe Glu Leu Ser
                805                 810                 815

Gln Glu Glu Lys Gln Ala Ser Lys Lys Tyr Leu Gln Glu Lys Leu Asn
                820                 825                 830

Pro Ile Ser Glu Ile Thr Ile Val Lys Leu Pro Pro Lys Glu Glu Val
            835                 840                 845

Leu Pro Pro Leu Glu Glu Lys Lys Pro Glu Gln Asp Gln Lys Ala
850                 855                 860

Gln Glu Lys Gln Glu Asp Lys Gln Asn Gln Lys Gln Gln Glu Lys Gln
865                 870                 875                 880

Glu Asp Lys Lys Glu Gln Asp Gln Gln Lys His Ser Gln Ser Pro Asp
                885                 890                 895

Gln Lys Thr Glu Thr Gln Thr His Asp Gln Glu Lys Asp Lys Gln Thr
            900                 905                 910

Ser Ser Glu Thr Ser Pro Ser Asn Thr Asn Glu Ser Ser Gly Thr Gln
            915                 920                 925

Asn Thr Ala Gln Asn Ser Gln Thr Asn Gln Ala Asn Ser Gly Gln Gly
            930                 935                 940

Gln Ser Gln Gln Ala Ala Ser Ser Ser Thr Ser Tyr Gln Thr His Lys
945                 950                 955                 960

Ile Thr Thr Phe Gln Asp Asp Gln Lys Asp Gln Thr Asn Glu Gln Thr
                965                 970                 975

Glu Lys Glu Ile Glu Pro Glu Lys Leu Ala Phe Gly Asp Tyr Leu Val
                980                 985                 990

Lys Tyr Leu Asp Ile Phe Glu Thr Phe Lys Val Gly Pro Asp Gln Lys
            995                 1000                1005

Leu Ser Ile Gly Arg Trp Tyr Asn Ala Pro Gln Arg Thr Tyr Asn
    1010                1015                1020

Val Ile Phe Arg Val Leu Asp Lys Glu Asn Ile Gln Val Ala Ala
    1025                1030                1035
```

```
Ser Leu Phe Gln Leu His Gly Ile Ser Ala Thr Asn Ile Ala Leu
    1040                1045                1050

Glu Lys Ser Leu Arg Tyr Ala Pro Asp Ile Phe Leu Asp Gly Thr
    1055                1060                1065

Ser Gly Leu Glu Tyr Lys Gln Asp Thr Gly Asp Lys Pro Tyr Leu
    1070                1075                1080

Gln Gly Arg Gln Phe Val Ser Ala Ile Asn Ser Ile Asn Asn Thr
    1085                1090                1095

Lys Ser Ser Tyr Arg Val His Lys Leu Phe Asp Asn Leu Pro Leu
    1100                1105                1110

Ser Glu Glu Ser Ser Gln Gly Leu Arg Leu Lys Ser Ser Leu Val
    1115                1120                1125

Tyr Asp Tyr Gln Lys Asn Asp Pro Tyr Thr Phe Gln Ala Ser Lys
    1130                1135                1140

Glu Ala Leu Arg Lys Thr Ala Leu Thr Lys Gly Val Leu Tyr Leu
    1145                1150                1155

Ala Phe Lys Pro Glu Gln Ile Leu Gly Ile Lys Gly Ser Lys Thr
    1160                1165                1170

Ala Pro Gly Arg Asn Tyr Lys Leu Leu Ser Thr Thr Asn Val His
    1175                1180                1185

Phe Lys Ser Leu Tyr Gly Leu Ser Asn Leu Glu Leu Val Lys Thr
    1190                1195                1200

Lys Tyr Gln Glu Asn Leu Lys Leu Val Trp Lys Leu Ile Gly Ala
    1205                1210                1215

Lys Pro Val Asn Asp Asp Lys Ile Leu Pro Pro Gln Val Ala Asp
    1220                1225                1230

Leu Pro Arg His Arg Ser Thr Glu Ile Ile Leu Leu Glu Asp Ser
    1235                1240                1245

Lys Pro Gly Ala Ser Ser Ser Pro Gln Thr Lys Glu Asn Ser Gln
    1250                1255                1260

Asn Lys Glu Ala Glu Thr Phe Asn Leu Asp Ile Arg Gln Thr Lys
    1265                1270                1275

Pro Asn Gln Ile Glu Pro Leu Glu His Tyr Leu Gly Gln Thr Trp
    1280                1285                1290

Leu Met Glu Ile Arg Ile Asp Asp Glu Ser Ala Thr Ile Thr Ile
    1295                1300                1305

Ile Pro Glu Gln Gln Glu Arg Glu Asp Ser Lys Leu Lys Val Trp
    1310                1315                1320

Lys Ser Glu Ile Lys Ile Lys Asp Lys Asn Lys Tyr Gln Asn Gln
    1325                1330                1335

Asp Thr Asn Trp Glu Thr Glu Leu Ala Ser Val Leu Gly Arg Gly
    1340                1345                1350

Phe Asp Tyr Gly Gln Ile Gly Asp Thr Thr Pro Gln Ala Ser Asn
    1355                1360                1365

Pro Gln Asp Arg Val Gly Met Thr Phe Lys Gly Phe Ala Val Phe
    1370                1375                1380

Lys Gly Asp Lys Leu Leu Asn Asp Lys Ala Arg Leu Asn Val Arg
    1385                1390                1395

Lys Ala Phe Met Asp Gln Tyr Phe Lys Asn Tyr Ser
    1400                1405                1410

<210> SEQ ID NO 6
<211> LENGTH: 1878
<212> TYPE: PRT
```

<213> ORGANISM: Mycoplasma hyopneumoniae

<400> SEQUENCE: 6

Met Lys Asn Lys Lys Ser Thr Leu Leu Leu Ala Thr Ala Ala Ala Ile
1               5                   10                  15

Ile Gly Ser Thr Val Phe Gly Thr Val Val Gly Leu Ala Ser Lys Val
            20                  25                  30

Lys Tyr Arg Gly Val Asn Pro Thr Gln Gly Val Ile Ser Gln Leu Gly
        35                  40                  45

Leu Ile Asp Ser Val Ala Phe Lys Pro Ser Ile Ala Asn Phe Thr Ser
    50                  55                  60

Asp Tyr Gln Ser Val Lys Lys Ala Leu Leu Asn Gly Lys Thr Phe Asp
65                  70                  75                  80

Pro Lys Ser Ser Glu Phe Thr Asp Phe Val Ser Lys Phe Asp Phe Leu
                85                  90                  95

Thr Asn Asn Gly Arg Thr Val Leu Glu Ile Pro Lys Lys Tyr Gln Val
            100                 105                 110

Val Ile Ser Glu Phe Ser Pro Glu Asp Asp Lys Glu Arg Phe Arg Leu
        115                 120                 125

Gly Phe His Leu Lys Glu Lys Leu Glu Asp Gly Asn Ile Ala Gln Ser
    130                 135                 140

Ala Thr Lys Phe Ile Tyr Leu Leu Pro Leu Asp Met Pro Lys Ala Ala
145                 150                 155                 160

Leu Gly Gln Tyr Ser Tyr Ile Val Asp Lys Asn Phe Asn Asn Leu Ile
                165                 170                 175

Ile His Pro Leu Ser Asn Phe Ser Ala Gln Ser Ile Lys Pro Leu Ala
            180                 185                 190

Leu Thr Arg Ser Ser Asp Phe Ile Ala Lys Leu Asn Gln Phe Lys Asn
        195                 200                 205

Gln Asp Glu Leu Trp Val Tyr Leu Glu Lys Phe Phe Asp Leu Glu Ala
    210                 215                 220

Leu Lys Ala Asn Ile Arg Leu Gln Thr Ala Asp Phe Ser Phe Glu Lys
225                 230                 235                 240

Gly Asn Leu Val Asp Pro Phe Val Tyr Ser Phe Ile Arg Asn Pro Gln
                245                 250                 255

Asn Gly Lys Glu Trp Ala Ser Asp Leu Asn Gln Asp Gln Lys Thr Val
            260                 265                 270

Arg Leu Tyr Leu Arg Thr Glu Phe Ser Pro Gln Ala Lys Thr Ile Leu
        275                 280                 285

Lys Asp Tyr Lys Tyr Lys Asp Glu Thr Phe Leu Ser Ser Ile Asp Leu
    290                 295                 300

Lys Ala Ser Asn Gly Thr Ser Leu Phe Ala Asn Glu Asn Asp Leu Lys
305                 310                 315                 320

Asp Gln Leu Asp Val Asp Leu Leu Asp Val Ser Asp Tyr Phe Gly Gly
                325                 330                 335

Gln Ser Glu Thr Ile Thr Ser Asn Ser Gln Val Lys Pro Val Pro Ala
            340                 345                 350

Ser Glu Arg Ser Leu Lys Asp Arg Val Lys Phe Lys Lys Asp Gln Gln
        355                 360                 365

Lys Pro Arg Ile Glu Lys Phe Ser Leu Tyr Glu Tyr Asp Ala Leu Ser
    370                 375                 380

Phe Tyr Ser Gln Leu Gln Glu Leu Val Ser Lys Pro Asn Ser Ile Lys
385                 390                 395                 400

-continued

```
Asp Leu Val Asn Ala Thr Leu Ala Arg Asn Leu Arg Phe Ser Leu Gly
            405                 410                 415
Lys Tyr Asn Phe Leu Phe Asp Leu Ala Ser His Leu Asp Tyr Thr
        420                 425                 430
Phe Leu Val Ser Lys Ala Lys Ile Lys Gln Ser Ser Ile Thr Lys Lys
            435                 440                 445
Leu Phe Ile Glu Leu Pro Ile Lys Ile Ser Leu Lys Ser Ser Ile Leu
450                 455                 460
Gly Asp Gln Glu Pro Asn Ile Lys Thr Leu Phe Glu Lys Glu Val Thr
465                 470                 475                 480
Phe Lys Leu Asp Asn Phe Arg Asp Val Glu Ile Glu Lys Ala Phe Gly
                485                 490                 495
Leu Leu Tyr Pro Gly Val Asn Glu Glu Leu Glu Gln Ala Arg Arg Glu
            500                 505                 510
Gln Arg Ala Ser Leu Glu Lys Glu Lys Ala Lys Lys Gly Leu Lys Glu
        515                 520                 525
Phe Ser Gln Gln Lys Asp Glu Asn Leu Lys Ala Ile Asn Asn Gln Asp
    530                 535                 540
Gly Leu Glu Glu Asp Asp Asn Ile Thr Glu Arg Leu Pro Glu Asn Ser
545                 550                 555                 560
Pro Ile Gln Tyr Gln Gln Glu Lys Ala Gly Leu Gly Ser Ser Pro Asp
                565                 570                 575
Lys Pro Tyr Met Ile Lys Asp Val Gln Asn Gln Arg Tyr Tyr Leu Ala
                580                 585                 590
Lys Ser Gln Ile Gln Glu Leu Ile Lys Ala Lys Asp Tyr Thr Lys Leu
        595                 600                 605
Ala Lys Leu Leu Ser Asn Arg His Thr Tyr Asn Ile Ser Leu Arg Leu
    610                 615                 620
Lys Glu Gln Leu Phe Glu Val Asn Pro Arg Ile Pro Ser Ser Arg Asp
625                 630                 635                 640
Ile Glu Asn Ala Lys Phe Val Leu Asp Lys Thr Glu Lys Asn Lys Tyr
                645                 650                 655
Trp Gln Ile Tyr Ser Ser Ala Ser Pro Ala Phe Gln Asn Lys Trp Ser
            660                 665                 670
Leu Phe Gly Tyr Tyr Arg Tyr Leu Leu Gly Leu Asp Pro Lys Gln Thr
        675                 680                 685
Ile His Glu Leu Val Lys Leu Gly Gln Lys Ala Gly Leu Gln Phe Glu
    690                 695                 700
Gly Tyr Glu Asn Leu Pro Ser Asp Phe Asn Leu Glu Asp Leu Lys Asn
705                 710                 715                 720
Ile Arg Ile Lys Thr Pro Leu Phe Ser Gln Lys Asp Asn Phe Lys Leu
                725                 730                 735
Ser Leu Leu Asp Phe Asn Asn Tyr Tyr Asp Gly Glu Ile Lys Ala Pro
            740                 745                 750
Glu Phe Gly Leu Pro Leu Phe Leu Pro Lys Glu Leu Arg Lys Asn Ser
        755                 760                 765
Ser Asn Ile Gly Ser Ser Gln Asn Ser Asn Ser Pro Trp Glu Gln Glu
    770                 775                 780
Ile Ile Ser Gln Phe Lys Asp Gln Asn Leu Ser Asn Gln Asp Gln Leu
785                 790                 795                 800
Ala Gln Phe Ser Thr Lys Ile Trp Glu Lys Ile Ile Gly Asp Glu Asn
                805                 810                 815
Glu Phe Asp Gln Asn Asn Arg Leu Gln Tyr Lys Leu Leu Lys Asp Leu
```

```
                820             825             830
Gln Glu Ser Trp Ile Asn Lys Thr Arg Asp Asn Leu Tyr Trp Thr Tyr
            835             840             845
Leu Gly Asp Lys Leu Lys Val Lys Pro Lys Asn Asn Leu Asp Ala Lys
            850             855             860
Phe Arg Gln Ile Ser Asn Leu Gln Glu Leu Leu Thr Ala Phe Tyr Thr
865             870             875             880
Ser Ala Ala Leu Ser Asn Asn Trp Asn Tyr Tyr Gln Asp Ser Gly Ala
                885             890             895
Lys Ser Thr Ile Ile Phe Glu Glu Ile Ala Glu Leu Asp Pro Lys Val
            900             905             910
Lys Glu Lys Val Gly Ala Asp Val Tyr Gln Leu Lys Phe His Tyr Ala
            915             920             925
Ile Gly Phe Asp Asp Asn Ala Gly Lys Phe Asn Gln Glu Val Ile Arg
            930             935             940
Ser Ser Ser Arg Thr Ile Tyr Leu Lys Thr Ser Gly Lys Ser Lys Leu
945             950             955             960
Glu Ala Asp Thr Ile Asp Gln Leu Asn Gln Ala Val Glu Asn Ala Pro
            965             970             975
Leu Gly Leu Gln Ser Phe Tyr Leu Asp Thr Glu Arg Phe Gly Val Phe
            980             985             990
Gln Lys Leu Ala Thr Ser Leu Ala  Val Gln His Lys Gln  Lys Glu Lys
            995            1000            1005
Pro Leu  Pro Lys Lys Leu Asn  Asn Asp Gly Tyr Thr  Leu Ile His
           1010            1015            1020
Asp Lys  Leu Lys Lys Pro Val  Ile Pro Gln Ile Ser  Ser Ser Pro
           1025            1030            1035
Glu Lys  Asp Trp Phe Glu Gly  Lys Leu Asn Gln Asn  Gly Gln Ser
           1040            1045            1050
Gln Asn  Val Asn Val Ser Thr  Phe Gly Ser Ile Ile  Glu Ser Pro
           1055            1060            1065
Tyr Phe  Ser Thr Asn Phe Gln  Glu Glu Ala Asp Leu  Asp Gln Glu
           1070            1075            1080
Gly Gln  Asp Asp Ser Lys Gln  Gly Asn Lys Ser Leu  Asp Asn Gln
           1085            1090            1095
Glu Ala  Gly Leu Leu Lys Gln  Lys Leu Ala Ile Leu  Leu Gly Asn
           1100            1105            1110
Gln Phe  Ile Gln Tyr Tyr Gln  Asn Asp Lys Glu  Ile Glu Phe
           1115            1120            1125
Glu Ile  Ile Asn Val Glu Lys  Val Ser Glu Leu Ser  Phe Arg Val
           1130            1135            1140
Glu Phe  Lys Leu Ala Lys Thr  Leu Glu Asp Asn Gly  Lys Thr Ile
           1145            1150            1155
Arg Val  Leu Ser Asp Glu Thr  Met Ser Leu Ile Val  Asn Thr Thr
           1160            1165            1170
Ile Glu  Lys Ala Pro Glu Met  Ser Ala Ala Pro Glu  Val Phe Asp
           1175            1180            1185
Thr Lys  Trp Val Glu Gln Tyr  Asp Pro Arg Thr Pro  Leu Ala Ala
           1190            1195            1200
Lys Thr  Lys Phe Val Leu Lys  Phe Lys Asp Gln Ile  Pro Val Asp
           1205            1210            1215
Ala Ser  Gly Asn Ile Ser Asp  Lys Trp Leu Ala Ser  Ile Pro Leu
           1220            1225            1230
```

```
-continued

Val Ile His Gln Gln Met Leu Arg Leu Ser Pro Val Val Lys Thr
            1235                1240                1245

Ile Arg Glu Leu Gly Leu Lys Thr Glu Gln Gln Gln Gln Gln Gln
    1250                1255                1260

Gln Gln Gln Gln Lys Lys Ala Val Arg Lys Glu Glu Glu Leu Glu
    1265                1270                1275

Thr Tyr Asn Pro Lys Asp Glu Phe Asn Ile Leu Asn Pro Leu Thr
    1280                1285                1290

Lys Ala His Arg Leu Thr Leu Ser Asn Leu Val Asn Asn Asp Pro
    1295                1300                1305

Asn Tyr Lys Ile Glu Asp Leu Lys Val Ile Lys Asn Glu Ala Gly
    1310                1315                1320

Asp His Gln Leu Glu Phe Ser Leu Arg Ala Asn Asn Ile Lys Arg
    1325                1330                1335

Leu Met Asn Thr Pro Ile Thr Phe Ala Asp Tyr Asn Pro Phe Phe
    1340                1345                1350

Tyr Phe Asn Glu Asp Trp Arg Asn Ile Asp Lys Tyr Leu Asn Asn
    1355                1360                1365

Lys Gly Asn Val Ser Ser Gln Gln Gln Gln Gln Gln Gln Gln Gln
    1370                1375                1380

Pro Gly Gly Gly Asn Gln Gly Ser Gly Leu Ile Gln Arg Leu Asn
    1385                1390                1395

Lys Asn Ile Lys Pro Glu Thr Phe Thr Pro Ala Leu Ile Ala Leu
    1400                1405                1410

Lys Arg Asp Asn Asn Thr Asn Leu Ser Asn Tyr Ser Asp Lys Ile
    1415                1420                1425

Ile Met Ile Lys Pro Lys Tyr Leu Val Glu Arg Ser Ile Gly Val
    1430                1435                1440

Pro Trp Ser Thr Gly Leu Asp Gly Tyr Ile Gly Ser Glu Gln Leu
    1445                1450                1455

Lys Gly Gly Thr Ser Ser Asn Gly Gln Lys Arg Phe Lys Gln Asp
    1460                1465                1470

Phe Ile Gln Ala Leu Gly Leu Lys Asn Thr Glu Tyr His Gly Lys
    1475                1480                1485

Leu Gly Leu Ser Ile Arg Ile Phe Asp Pro Gly Asn Glu Leu Ala
    1490                1495                1500

Lys Ile Lys Asp Ala Ser Asn Lys Lys Gly Glu Glu Lys Leu Leu
    1505                1510                1515

Lys Ser Tyr Asp Leu Phe Lys Asn Tyr Leu Asn Glu Tyr Glu Lys
    1520                1525                1530

Lys Ser Pro Lys Ile Ala Lys Gly Trp Thr Asn Ile His Pro Asp
    1535                1540                1545

Gln Lys Glu Tyr Pro Asn Pro Asn Gln Lys Leu Pro Glu Asn Tyr
    1550                1555                1560

Leu Asn Leu Val Leu Asn Gln Pro Trp Lys Val Thr Leu Tyr Asn
    1565                1570                1575

Ser Ser Asp Phe Ile Thr Asn Leu Phe Val Glu Pro Glu Gly Ser
    1580                1585                1590

Asp Arg Gly Ser Gly Ala Lys Leu Lys Gln Val Ile Gln Lys Gln
    1595                1600                1605

Val Asn Asn Asn Tyr Ala Asp Trp Gly Ser Ala Tyr Leu Thr Phe
    1610                1615                1620
```

-continued

Trp Tyr Asp Lys Asp Ile Ile Thr Asn Gln Pro Asn Val Ile Thr
1625 1630 1635

Ala Asn Ile Ala Asp Val Phe Ile Lys Asp Val Lys Glu Leu Glu
1640 1645 1650

Asp Asn Thr Lys Leu Ile Ala Pro Asn Ile Thr Gln Trp Trp Pro
1655 1660 1665

Asn Ile Ser Gly Ser Lys Glu Lys Phe Tyr Lys Pro Thr Val Phe
1670 1675 1680

Phe Gly Asn Trp Glu Asn Glu Asn Ser Asn Met Asn Ser Gln Gly
1685 1690 1695

Gln Thr Pro Thr Trp Glu Lys Ile Arg Glu Gly Phe Ala Leu Gln
1700 1705 1710

Ala Leu Lys Ser Ser Phe Asp Gln Lys Thr Arg Thr Phe Val Leu
1715 1720 1725

Thr Thr Asn Ala Pro Leu Pro Leu Trp Lys Tyr Gly Pro Leu Gly
1730 1735 1740

Phe Gln Asn Gly Pro Asn Phe Lys Thr Gln Asp Trp Arg Leu Val
1745 1750 1755

Phe Gln Asn Asp Asp Asn Gln Ile Ala Ala Leu Arg Val Gln Glu
1760 1765 1770

Gln Asp Arg Pro Glu Lys Ser Ser Glu Asp Lys Asp Lys Gln Lys
1775 1780 1785

Trp Ile Lys Phe Lys Val Val Ile Pro Glu Glu Met Phe Asn Ser
1790 1795 1800

Gly Asn Ile Arg Phe Val Gly Val Met Gln Ile Gln Gly Pro Asn
1805 1810 1815

Thr Leu Trp Leu Pro Val Ile Asn Ser Ser Val Ile Tyr Asp Phe
1820 1825 1830

Tyr Arg Gly Thr Gly Asp Ser Asn Asp Val Ala Asn Leu Asn Val
1835 1840 1845

Ala Pro Trp Gln Val Lys Thr Ile Ala Phe Thr Asn Asn Ala Phe
1850 1855 1860

Asn Asn Val Phe Lys Glu Phe Asn Ile Ser Lys Lys Ile Val Glu
1865 1870 1875

<210> SEQ ID NO 7
<211> LENGTH: 1092
<212> TYPE: PRT
<213> ORGANISM: Mycoplasma hyopneumoniae

<400> SEQUENCE: 7

Met Ser Lys Lys Ser Lys Thr Phe Lys Ile Gly Leu Thr Ala Gly Ile
1 5 10 15

Val Gly Leu Gly Val Phe Gly Leu Thr Val Gly Leu Ser Ser Leu Ala
20 25 30

Lys Tyr Arg Ser Glu Ser Pro Arg Lys Ile Ala Asn Asp Phe Ala Ala
35 40 45

Lys Val Ser Thr Leu Ala Phe Ser Pro Tyr Ala Phe Glu Thr Asp Ser
50 55 60

Asp Tyr Lys Ile Val Lys Arg Trp Leu Val Asp Ser Asn Asn Asn Ile
65 70 75 80

Arg Asn Lys Glu Lys Val Ile Asp Ser Phe Ser Phe Phe Thr Lys Asn
85 90 95

Gly Asp Gln Leu Glu Lys Ile Asn Phe Gln Asp Pro Glu Tyr Thr Lys
100 105 110

```
Ala Lys Ile Thr Phe Glu Ile Leu Glu Ile Pro Asp Val Asn
        115                 120                 125
Gln Asn Phe Lys Val Lys Phe Gln Ala Leu Gln Lys Leu His Asn Gly
    130                 135                 140
Asp Ile Ala Lys Ser Asp Ile Tyr Glu Gln Thr Val Ala Phe Ala Lys
145                 150                 155                 160
Gln Ser Asn Leu Leu Val Ala Glu Phe Asn Phe Ser Leu Lys Lys Ile
                165                 170                 175
Thr Glu Lys Leu Asn Gln Gln Ile Glu Asn Leu Ser Thr Lys Ile Thr
            180                 185                 190
Asn Phe Ala Asp Glu Lys Thr Ser Ser Gln Lys Asp Pro Ser Thr Leu
        195                 200                 205
Arg Ala Ile Asp Phe Gln Tyr Asp Leu Asn Thr Ala Arg Asn Ala Glu
    210                 215                 220
Asp Leu Asp Ile Lys Leu Ala Asn Tyr Phe Pro Val Leu Lys Asn Leu
225                 230                 235                 240
Ile Asn Arg Leu Asn Asn Ala Pro Glu Asn Lys Leu Pro Asn Asn Leu
                245                 250                 255
Gly Asn Ile Phe Glu Phe Ser Phe Ala Lys Asp Ser Ser Thr Asn Gln
            260                 265                 270
Tyr Val Ser Ile Gln Asn Gln Ile Pro Ser Leu Phe Leu Lys Ala Asp
        275                 280                 285
Leu Ser Gln Ser Ala Arg Glu Ile Leu Ala Ser Pro Asp Glu Val Gln
    290                 295                 300
Pro Val Ile Asn Ile Leu Arg Leu Met Lys Lys Asp Asn Ser Ser Tyr
305                 310                 315                 320
Phe Leu Asn Phe Glu Asp Phe Val Asn Asn Leu Thr Leu Lys Asn Met
                325                 330                 335
Gln Lys Glu Asp Leu Asn Ala Lys Gly Gln Asn Leu Ser Ala Tyr Glu
            340                 345                 350
Phe Leu Ala Asp Ile Lys Ser Gly Phe Phe Pro Gly Asp Lys Arg Ser
        355                 360                 365
Ser His Thr Lys Ala Glu Ile Ser Asn Leu Leu Asn Lys Lys Glu Asn
    370                 375                 380
Ile Tyr Asp Phe Gly Lys Tyr Asn Gly Lys Phe Asn Asp Arg Leu Asn
385                 390                 395                 400
Ser Pro Asn Leu Glu Tyr Ser Leu Asp Ala Ala Ser Ala Ser Leu Asp
                405                 410                 415
Lys Lys Asp Lys Ser Ile Ile Leu Ile Pro Tyr Arg Leu Glu Ile Lys
            420                 425                 430
Asp Lys Phe Phe Ala Asp Asp Leu Tyr Pro Asp Thr Lys Asp Asn Ile
        435                 440                 445
Leu Val Lys Glu Gly Ile Leu Lys Leu Thr Gly Phe Lys Lys Gly Pro
    450                 455                 460
Lys Ile Asp Leu Pro Asn Ile Asn Gln Gln Ile Phe Lys Thr Glu Tyr
465                 470                 475                 480
Leu Pro Phe Phe Glu Lys Gly Lys Glu Glu Ala Lys Leu Asp Tyr
                485                 490                 495
Gly Asn Ile Leu Asn Pro Tyr Asn Thr Gln Leu Ala Lys Val Glu Val
            500                 505                 510
Glu Ala Leu Phe Lys Gly Asn Lys Asn Gln Glu Ile Tyr Gln Ala Leu
        515                 520                 525
```

```
Asp Gly Asn Tyr Ala Tyr Glu Phe Gly Ala Phe Lys Ser Val Leu Asn
    530                 535                 540

Ser Trp Thr Gly Lys Ile Gln His Pro Glu Lys Ala Asp Ile Gln Arg
545                 550                 555                 560

Phe Thr Arg His Leu Glu Gln Val Lys Leu Gly Ser Asn Ser Val Leu
                565                 570                 575

Asn Gln Pro Gln Thr Thr Lys Glu Gln Val Ile Ser Ser Leu Lys Ser
            580                 585                 590

Asn Asn Phe Phe Lys Asn Gly His Gln Val Ala Ser Tyr Phe Gln Asp
        595                 600                 605

Leu Leu Thr Lys Asp Lys Leu Thr Val Leu Glu Thr Leu Tyr Asp Leu
    610                 615                 620

Ala Lys Lys Trp Gly Leu Glu Thr Asn Arg Ala Gln Phe Pro Lys Glu
625                 630                 635                 640

Val Phe Gln Tyr Thr Lys Asp Ile Phe Ala Glu Ala Asp Lys Leu Lys
                645                 650                 655

Phe Leu Glu Gly Lys Lys Asp Pro Tyr Asn Gln Ile Lys Glu Ile
            660                 665                 670

His Gln Leu Ser Phe Asn Ile Leu Ala Arg Asn Asp Val Ile Lys Ser
        675                 680                 685

Asp Gly Phe Tyr Gly Val Leu Leu Pro Gln Ser Val Lys Thr Glu
    690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
            740                 745                 750

Phe Phe Leu Lys Ala Ala Gln Phe Asn Asn Phe Ala Pro Trp Ala Lys
        755                 760                 765

Leu Asp Asp Asn Leu Gln Tyr Ser Phe Glu Ala Ile Lys Lys Gly Glu
    770                 775                 780

Thr Thr Lys Glu Gly Lys Arg Glu Glu Val Asp Lys Lys Val Lys Glu
785                 790                 795                 800

Leu Asp Asn Lys Ile Lys Gly Ile Leu Pro Gln Pro Ala Ala Lys
                805                 810                 815

Pro Glu Ala Ala Lys Pro Val Ala Ala Lys Pro Glu Ala Ala Lys Pro
            820                 825                 830

Glu Thr Thr Lys Pro Val Ala Ala Lys Pro Glu Ala Ala Lys Pro Val
        835                 840                 845

Ala Ala Lys Pro Val Ala Ala Lys Pro Val Ala Thr Asn Thr Asn Thr
    850                 855                 860

Asn Thr Gly Phe Ser Leu Thr Asn Lys Pro Lys Glu Asp Tyr Phe Pro
865                 870                 875                 880

Met Ala Phe Ser Tyr Lys Leu Glu Tyr Thr Asp Glu Asn Lys Leu Ser
                885                 890                 895

Leu Lys Thr Pro Glu Ile Asn Val Phe Leu Glu Leu Val His Gln Ser
            900                 905                 910

Glu Tyr Glu Glu Gln Lys Ile Ile Lys Glu Leu Asp Lys Thr Val Leu
        915                 920                 925

Asn Leu Gln Tyr Gln Phe Gln Glu Val Lys Val Thr Ser Glu Gln Tyr
    930                 935                 940

Gln Lys Leu Ser His Pro Met Met Thr Glu Gly Ser Pro Asn Gln Gly
```

```
                  945                 950                 955                 960
            Lys Lys Ala Glu Gly Ala Pro Asn Gln Gly Lys Lys Ala Glu Gly Ala
                            965                 970                 975

Pro Ser Gln Gly Lys Lys Ala Glu Gly Ala Pro Asn Gln Gly Lys Lys
                            980                 985                 990

Ala Glu Gly Ala Pro Ser Gln Gly  Lys Lys Ala Glu Gly  Ala Ser Asn
                            995                 1000                1005

Gln Gln Ser Thr Thr Thr Glu  Leu Thr Asn Tyr Leu  Pro Glu Leu
                    1010                1015                1020

Gly Lys Lys Ile Asp Glu Ile  Ile Lys Lys Gln Gly  Lys Asn Trp
                    1025                1030                1035

Lys Thr  Glu Val Glu Leu Ile  Glu Asp Asn Ile Ala  Gly Asp Ala
                    1040                1045                1050

Lys Leu  Leu Tyr Phe Val Leu  Arg Asp Asp Ser Lys  Ser Gly Asp
                    1055                1060                1065

Pro Lys  Lys Ser Ser Leu Lys  Val Lys Ile Thr Val  Lys Gln Ser
                    1070                1075                1080

Asn Asn  Asn Gln Glu Leu Lys  Ser Lys
                    1085                1090

<210> SEQ ID NO 8
<211> LENGTH: 933
<212> TYPE: DNA
<213> ORGANISM: Mycoplasma hyopneumoniae
<220> FEATURE:
<221> NAME/K -continued

| | | |
|---|---|---|
| tac cag ttc cag gaa gtg aaa gtc acc tcc gac cag tac cag aaa ctg<br>Tyr Gln Phe Gln Glu Val Lys Val Thr Ser Asp Gln Tyr Gln Lys Leu<br>                    165                      170                    175 | 528 | |
| tcc cac ccc atg atg acc gag ggc tcc tcc aac cag ggc aag aag tcc<br>Ser His Pro Met Met Thr Glu Gly Ser Ser Asn Gln Gly Lys Lys Ser<br>                180                     185                     190 | 576 | |
| gag ggg acc ccc aac cag ggg aaa aag gcc gaa ggc gcc cca aac cag<br>Glu Gly Thr Pro Asn Gln Gly Lys Lys Ala Glu Gly Ala Pro Asn Gln<br>     195                       200                     205 | 624 | |
| gga aag aaa gcc gag ggc aca cct aat cag ggc aaa aaa gcc gaa ggg<br>Gly Lys Lys Ala Glu Gly Thr Pro Asn Gln Gly Lys Lys Ala Glu Gly<br>210                      215                     220 | 672 | |
| gct cct tcc cag cag tcc cca acc acc gag ctg acc aac tac ctg ccc<br>Ala Pro Ser Gln Gln Ser Pro Thr Thr Glu Leu Thr Asn Tyr Leu Pro<br>225                      230                     235                     240 | 720 | |
| gac ctg ggc aag aag atc gac gag atc atc aag aag cag ggg aag aac<br>Asp Leu Gly Lys Lys Ile Asp Glu Ile Ile Lys Lys Gln Gly Lys Asn<br>                245                     250                     255 | 768 | |
| tgg aaa acc gag gtg gag ctg atc gag gac aat atc gcc ggc gac gcc<br>Trp Lys Thr Glu Val Glu Leu Ile Glu Asp Asn Ile Ala Gly Asp Ala<br>                    260                     265                     270 | 816 | |
| aag ctg ctg tac ttc atc ctg cgc gac gac tcc aag tcc ggc gac ccc<br>Lys Leu Leu Tyr Phe Ile Leu Arg Asp Asp Ser Lys Ser Gly Asp Pro<br>                275                     280                     285 | 864 | |
| aag aaa tcc tcc ctg aaa gtg aag atc acc gtg aag cag tcc aac aac<br>Lys Lys Ser Ser Leu Lys Val Lys Ile Thr Val Lys Gln Ser Asn Asn<br>290                      295                     300 | 912 | |
| aac cag gaa ccc gag tcc aag<br>Asn Gln Glu Pro Glu Ser Lys<br>305                    310 | 933 | |

<210> SEQ ID NO 9
<211> LENGTH: 311
<212> TYPE: PRT
<213> ORGANISM: Mycoplasma hyopneumoniae

<400> SEQUENCE: 9

Met Lys Glu Leu Asp Asn Lys Ile Lys Gly Ile Leu Pro Gln Pro Pro
1               5                   10                  15

Ala Ala Lys Pro Glu Ala Ala Lys Pro Val Ala Ala Lys Pro Glu Thr
            20                  25                  30

Thr Lys Pro Val Ala Ala Lys Pro Glu Ala Ala Lys Pro Glu Ala Ala
        35                  40                  45

Lys Pro Val Ala Ala Lys Pro Glu Ala Ala Lys Pro Val Ala Ala Lys
    50                  55                  60

Pro Glu Ala Ala Lys Pro Val Ala Ala Lys Pro Glu Ala Ala Lys Pro
65                  70                  75                  80

Val Ala Ala Lys Pro Glu Ala Ala Lys Pro Val Ala Thr Asn Thr Gly
                85                  90                  95

Phe Ser Leu Thr Asn Lys Pro Lys Glu Asp Tyr Phe Pro Met Ala Phe
            100                 105                 110

Ser Tyr Lys Leu Glu Tyr Thr Asp Glu Asn Lys Leu Ser Leu Lys Thr
        115                 120                 125

Pro Glu Ile Asn Val Phe Leu Glu Leu Val His Gln Ser Glu Tyr Glu
    130                 135                 140

Glu Gln Glu Ile Ile Lys Glu Leu Asp Lys Thr Val Leu Asn Leu Gln
145                 150                 155                 160

-continued

| | | | | | | | | | | | |
|---|---|---|---|---|---|---|---|---|---|---|---|
|Tyr|Gln|Phe|Gln|Glu|Val|Lys|Val|Thr|Ser|Asp|Gln|Tyr|Gln|Lys|Leu|
| | | | |165| | | |170| | | |  | |175| |

Ser His Pro Met Met Thr Glu Gly Ser Ser Asn Gln Gly Lys Lys Ser
           180                 185                 190

Glu Gly Thr Pro Asn Gln Gly Lys Lys Ala Glu Gly Ala Pro Asn Gln
           195                 200                 205

Gly Lys Lys Ala Glu Gly Thr Pro Asn Gln Gly Lys Lys Ala Glu Gly
           210                 215                 220

Ala Pro Ser Gln Gln Ser Pro Thr Thr Glu Leu Thr Asn Tyr Leu Pro
225                 230                 235                 240

Asp Leu Gly Lys Lys Ile Asp Glu Ile Ile Lys Lys Gln Gly Lys Asn
                245                 250                 255

Trp Lys Thr Glu Val Glu Leu Ile Glu Asp Asn Ile Ala Gly Asp Ala
           260                 265                 270

Lys Leu Leu Tyr Phe Ile Leu Arg Asp Asp Ser Lys Ser Gly Asp Pro
           275                 280                 285

Lys Lys Ser Ser Leu Lys Val Lys Ile Thr Val Lys Gln Ser Asn Asn
           290                 295                 300

Asn Gln Glu Pro Glu Ser Lys
305                 310

<210> SEQ ID NO 10
<211> LENGTH: 3327
<212> TYPE: DNA
<213> ORGANISM: Mycoplasma hyopneumoniae

<400> SEQUENCE: 10
atgagtaaaa aatcaaaaac atttaaaatt ggtttgactg ccggaattgt tggtcttgga      60
gttttggtc taactgtcgg acttagcagc ttggcaaaat acagatcaga aagtccacga     120
aagattgcaa atgattttgc cgcaaaagtt tcaacattag cttttagtcc ttatgctttt     180
gagactgatt ctgattataa aatagtcaaa aggtgcactg ttgattctaa taacaatatt     240
agaaataaag aaaaagttat tgattccttt ccttttttta ctaaaaacgg tgatcagtta     300
gaaaaaatta attttcaaga tcctgaatat accaaggcga agataacttt tgagattctt     360
gaaattatcc ctgatgatgt caatcaaaat tttaaggtaa aatttcaggc attacaaaaa     420
cttcataatg gtgatattgc caaatctgat atttatgagc aaacagttgc ttttgccaaa     480
cagtcaaatc ttttagttgc cgaatttaat ttttcgctta aaaaaattac cgaaaaatta     540
aatcaacaaa ttgaaaattt atcaacaaaa attacaaatt ttgctgatga aaaaacaagc     600
agccaaaaag atccctcaac tctaagagct attgacttcc aatacgattt aaatacagcg     660
cgaaatcctg aggatttaga tataaagctt gctaattatt ttccagtact aaaaatttta     720
ataaacagac taaataatgc tcctgagaat aaattaccta ataatttggg taatattttt     780
gaatttagct ttgcaaaaga tagttcaact aatcaatatg taagtatcca gaaccaaatt     840
ccttcgctgt ttttaaaagc agatcttagt caaagtgccc gtgaaatttt agctagccca     900
gatgaagttc agccagttat taacatttta agattaatga aaaagataa ttcttcttat     960
tttctaaatt ttgaggattt tgttaataat ttaacactga aaaatatgca aaagaagat    1020
ttaaatgcaa agggtcaaaa tctttctgcc tatgaatttc tagcagatat taaatctgga    1080
ttttcccctg agacaagag atccagtcat accaaggcag aaattagtaa tcttttaaat    1140
aaaaagaaa atatttatga ctttggtaaa tacaatggaa aattcaacga ccgtcttaac    1200
tcgccaaatt tagaatatag cctagatgca gcaagcgcaa gtcttgataa aaaagataaa    1260

```
tcaatagttt taattcccta ccgccttgaa attaaagata aatttttgc cgatgattta    1320 tatccagata caaagataa tattctcgta aagaaggga ttcttaaatt aactggattt    1380
aaaaaaggct caaaaattga tctccctaat atcaatcagc aaattttaa aaccgaatat    1440 ttaccatttt ttgaaaaagg taagaagaa caagcaaaat tagactatgg taatatctta    1500
aatccatata atactcaact tgccaaagtt gaagttgaag ctcttttaa agggaataaa    1560 aaccaagaaa tctatcaagc acttgatgga aattatgcct atgaattcgg ggcctttaaa    1620
tccgtgctta attcctgaac aggaaaaatt cagcatcctg aaaaagctga tatccaaaga    1680
tttacaagac atttagaaca agttaaaatt ggttctaatt cagttttaaa tcaaccacaa    1740
acaacaaaag aacaagtaat ttcaagtctt aaaagtaata actttttaa aaatggacat    1800 caagttgcaa gttatttcca ggatttactc accaaggaca aattaacaat tttagagact    1860
ctttatgatc tagcaaaaaa atggggacta gaaactaaca gagcacaatt cccaaaaggg    1920
gttttccaat atacaaaaga tatttttgca gaagcagata aattaaaatt tttggaattg    1980
aagaaaaagg atccttacaa tcagataaaa gaaattcacc aactttcctt taatattta    2040 gcccgtaacg atgtaataaa atctgatgga ttttacggag ttttattatt gccccaaagt    2100
gtaaaaactg aattagaagg caaaaatgag gcgcaaattt ttgaagcgct taaaaagtat    2160
tctttaattg agaactcggc ttttaaaact actattttag ataaaaattt acttgaaggg    2220
actgatttta aaaccttcgg tgattttta aaagcatttt tccttaaagc agcccaattt    2280
aataattttg ctccttgagc aaaattagac gataatcttc agtattcatt tgaagctatc    2340
aaaaaagggg aaactacaaa agaaggtaaa agagaagaag tagataaaaa agttaaggaa    2400
ttggataata aaataaaagg tatattgcct cagcccccag cagcaaaacc agaagcagca    2460
aaaccagtag cggctaaacc agaaacaaca aaaccagtag cagctaaacc tgaagcagct    2520
aaacctgaag cagcaaaacc agtagcggct aaaccagaag cagcaaaacc agtagcggct    2580
aaaccagaag cagcaaaacc agtagcggct aaaccagaag cagcaaaacc agtagcggct    2640
aaaccagaag cagcaaaacc agttgctact aatactggct tttcacttac aaataaacca    2700
aaagaagact atttcccaat ggcttttagt tataaattag aatatactga cgaaaataaa    2760
ttaagcctaa aaacaccgga aattaatgta ttttagaac tagttcatca agcgagtat    2820 gaagaacaag aaataataaa ggaactagat aaaactgttt taaatcttca atatcaattc    2880
caggaagtca aggtaactag tgaccaatat cagaaactta gccacccaat gatgaccgaa    2940
ggatcttcaa atcaaggtaa aaaaagcgaa ggaactccta accaaggtaa aaaagcagaa    3000
ggcgcgccta accaaggtaa aaaagccgaa ggaactccta accaagggaa aaaagcagag    3060
ggagcaccta gtcaacaaag cccaactacc gaattaacta attaccttcc tgacttaggt    3120
aaaaaaattg acgaaatcat taaaaaacaa ggtaaaaatt gaaaaacaga ggttgaacta    3180
atcgaggata atatcgctgg agatgctaaa ttgctatact ttatcctaag ggatgattca    3240
aaatccggtg atcctaaaaa atcaagtcta aaagttaaaa taacagtaaa acaaagtaat    3300
aataatcagg aaccagaatc taaataa                                        3327
```

<210> SEQ ID NO 11
<211> LENGTH: 3954
<212> TYPE: DNA
<213> ORGANISM: Mycoplasma hyopneumoniae

<400> SEQUENCE:

```
atggctaaga ataataagaa ttcattatta gtaacagcaa cagccattgt cggagttgca    60
gtatttgcaa caacagttgg gcttgtaacg cgaattcgtt ataaaggtga aaatccccgc   120
gctgaacttg aaagtttagt ttcaaaagtt caaaatgttg cctttaaatc cgatgtcttt   180
gataattcaa ctacatataa acaaataaaa gcattacttt tcgatgaaac aggaaaatta   240
agacccggaa ttgatcttaa taaatttatc tcttttata cagcggtaaa ttcaaaaatt    300
caaaaatttg aggtcagttt tgccccaaat aaacctttt ttgagtttat taatttaatt    360
cctgatgata aaaatcaaac atttacccct caatttcggg caaaacacca attagataat   420
aattataccg catattcatc aatttttaagt aaaaaaattg cttatgctca acgttcccag  480
tttgccttag ctgattttaa tgcaaatcat agaaaaatca ccaaaagttt tcaaacaaat   540
atccaaaatc ttcgggaaac tgattttca gtcgactttt cttcaagtca aacctcatta    600
gcatcacaaa aaattccttt tcttacccgc gttgaagatt ttgccgcaga tattaacaaa   660
tccggaaacc aagaagaggc aatttcaaga atttcgaaat acttccctga ttttcaaaga   720
tatattcatg agttaaaaga tgatcctaat aatgttttac cttttaaaaa aggtaaaatt   780
tttgacttta gtattacaag acgtgctggt acaaatgatt ttattagtct aagtgctaat   840
tctgaaccaa gtttttaat aaaagcaaga ctcacaaatg aggctaaatt tgaacttcgt    900
ggccttaata ttgaagaagc agaaatgctg gagagatta aattagttcc agttgatcaa    960
tttgttgtta atcttgaaac cgatctaaaa ccaggtcaag ccccagaaaa gtcacaaaaa  1020
cctcaaagtg aacaaaccga gattaaaaaa acttattttg ccgaaattga taaaattta   1080 agtaaaataa caatgcgcaa acttcaactt agcgacttta aggtagctcc acagacaagt  1140
tcttcgcaac caaagcaagt taaagcaagt gtttcagctt gatctaactt agatcaaggg  1200
caagaaaata gaatttagt tccggttagt cagcaaagtt cgaatccaca caacaccaa    1260 caacaacaac ctcaacctca aagtcagccc caacctcaac tcagagtca acctcaatct   1320 cagccgcagc ctaatgctca aactcagcct aaggctcaag ctcaaagctc tcctaaagcg  1380
ccagtccaaa aaccggcaac tcctgatcca tctaaatcat ttaaaattag aacaaaacgt  1440
gccagagact tcttaaaga gtttaataaa acatttata ggtctaataa acttaaatca    1500
caaaaactag aagaaaaaat taattctgaa tatttatcta ataaaattgg aattgatctt  1560
ggcgttctaa aaaatatat taataataat caagggattg aatatacttt tgatattgca   1620
aatgcaaaaa taagggatgc tcaagatgga attacaagcc atattgaaat tccagtaaca  1680
attagtcttt gatcaagttt ctttggtgat tcagataatg tttactaaa atcaaaaaca   1740 gaaactttca tcatcccctta tttccaaaag gaaactacat ctgaatcaaa agaccaaaaa  1800
gtaggacata cccaaaaaga actcgatcta aatcagaaac taatttatca actcagtgaa  1860
ctaccaggaa caagcgccca aggttcttct ggatctagtg cacaaacaga acaaattaaa  1920
gaagttaaac tcccaacact aactgctttt atttcaaaac aagaactaga agctctaatt  1980
gatggggata agaatttagc tagtcagcca acaagtcagg cagtatctgt ttctcaagaa  2040
gttaaaacaa ccgagttcca acaacaagag gcaaattcaa ctaattctag tccaagtagt  2100 ccaagccta gtccaactag tccaagtcca gctagtccaa gttcaagccc tagtccaact  2160
agtcctaaaa atctcgatga aaatatagga gtgccaaatc ctagatttga ggaaattaaa  2220
aaaataatta gttccgagtt tacttataag tataattttc gtgctaacga ggcacttta    2280 gatgcttgag ttgaaaaaca aaatttccca agtctaaaag atatttccca gtttagatca   2340
gatcaaagat tagcaaaaga ttataaactt gttaacttaa aatctaataa attcctaaaa   2400
```

```
gaagattatg atgttcttgc tttttatgct aatttagtcc agaaagatcc aagagaagtt   2460
cttcaatatt tatttgaaat tgcaaaagct aataatttaa ttggtcctga agaaaaatta   2520
gatcttaacc agatcgaaga tgatggcatc tttagacgag ctaaggcaat taaacttata   2580
gataaatcaa gtaataacca aggaatttat ggattttcct ttaataacca gtttttaaaa   2640
ttccacgaac gtggatggat gtcaacttta tatttaccta atgaggcaaa aactaaatta   2700
gcagattatc aaaatctttt atccgctggg ataagcgata ccaagatttt tagtgaactt   2760
aataaaattc aacctttaga tctaaatatt aaagtccaaa gtagtgattc aagtgattca   2820
aaatcagatt caagtgattc ttcagatgct aagaccactt ctacaaagca agatcttcta   2880
agtaaattaa ctagccttaa atctcaaata gaggctatag ttaaaaaata tgaaacagag   2940
tctaaaaatt atttagggac cgaaaataat aatagtagca gcagctcagg tactgaacag   3000
aagggctcat ctatccctga agaaaataaa aaattcatct tggaaaatac agcaaaactt   3060
gataatttag ccgatctact tttagctttc tattatcagg ctaaaagatt aaattttgca   3120
agttgaagtc aactccaaga cgaagatctt gactatcaaa tacaatttga gaaagaggct   3180
aataacactg agtcttcatc ctcttcatct tcttcatcct cttcatcttc atcttcttct   3240
tcttcatctt cttctgaaac cgatacaaac aaacctgaga atgcagttga atataaacta   3300
acttattatt ataaaattta taataaaact actaagaaag tagtttatac tacacctaaa   3360
acaattatca agctttatct tgcaagttct aatatcggag ttaaagaaaa acaagaacgt   3420
gaattaatga ataaattagt tttatctatc ccttcagctt attcaatttt ctatctaaaa   3480
caaagtgaat gagaacaagt taaaacaaat aatggccaac aaatgggtca gactggttcg   3540
agtcaagggt ttgagtctct tgaaccattt aagaaaatcc aagagatagt ccataaaaat   3600
aataaagact atgatctcaa agttgtaact atccgcgatg atgcttatgc agaaaatgct   3660
aaaattgttc acttaagggt ggttagaaaa gaagaacagc aagcagaaca aaaagagaaa   3720
gagaaggaaa aagaaaagga aaaggaacaa aaagaaacaa gttcccaagg ccaagttccc   3780
cagtcagcat ttttcttcca agttagactt ataaaagatg attatcaagg agcagaggcc   3840
tcaaatcagc aaacaagtag gcaagcgatg caaatgccaa acatggaaag ccaaaattca   3900
ggatcttctt ctagtgctcc ggcagcagct gctgctgcta aggcggcgag gtaa          3954
```

<210> SEQ ID NO 12
<211> LENGTH: 2715
<212> TYPE: DNA
<213> ORGANISM: Mycoplasma hyopneumoniae

<400> SEQUENCE: 12

```
atgaagttag caaaattact taaaaaacct ttttgattaa taacaacaat tgccggaatt     60
agtcttagtt tatcagccgc tgttggtaca gttgtcggaa ttaattctta taataaatca    120
tattattctt atctaaatca gatcccgagt cagctaaaag tagcaaaaaa tgctaaaatt    180
agtcaggaaa aatttgattc aattgtttta aatcttaaaa ttaaagataa ttttaaaaaa    240
tgatcggcaa aaacagtttt aactgctgcc aaaagtgatc tttatcgtta taatcttgtt    300
tctgcttttg atttaagtga actaataaac aatgattatt tagtaagttt tgatcttgaa    360
aatgcagtag ttgatcaaaa ttcaattaaa aatgttgtta tttatgcaaa atctgataag    420
gatcaaataa cttattcaaa acaaattgta cttaaaggct ttggaaatac agaacaagct    480
agaactaatt ttgattttag tcaaattgat tcaagcaagt cttttgttga tctttcaaga    540
```

```
gcaaatctaa ctttgatgga attccaaatt ttgcttgccc aaaattttga aaatgaaaga    600
ggaagtaatt gattttcacg acttgaaaga gctttggttg catcaaaagc gagtctttca    660
ctttataatt ccttaggaga acccgtattt ttaggcccag attatcaatt agacccagtt    720
ttggaccgaa aaaaattatt aactttgtta aataaagatg gaaaattagt tcttggactt    780
aatttagtgc aaatttcaac taaaaaaact atgaatttaa atcttgaagt tcgcggcgcg    840
atttcaaatc aggaaatttc taaaattcta aatcctgac ttgaaacaaa tcttcaaggc    900
aaattaaaaa ccaaagatga tttgcaaatg gcactagtaa aagataaaat tagcctctct    960
gattattgat atggatctcc gaattcaaaa gtaaatacat cccaaatttt aacaaaaagt   1020
aaagaattta aagatctttt tgatttaagt gagacaaatt ttttcttaa taccaaaatc   1080 ggaactgtct atttaagtat tattcccaaa cttttagatc aagtcagat ttctgttgtt   1140 gataagaaaa aactagttga aaatcaaaaa attcgctttg aaattactgc ttctttaaaa   1200
cgaaaagcta ttgataaaaa atttatcatc caggatcttc cagttttttgt tgatctaaaa   1260 gttgatttta ataaatacca agccgctgtt gcccaaatgt ttggaacgat aaaagcagtt   1320
aaagaatttt caatgcctga agatcaagat gcaaaaactt tatcctcaaa tgaaataaaa   1380
cagcgagttg atcgactttt tgaactagca aaaacagtga ctaatttgga aaatccaagt   1440
gaagaagttc ttaaaagcat ttatttatta aatacgggaa aatatttagt cgaccaagac   1500
caggaaaaag taaacaaga gctaaaaacc gtgattgagg gcttaaaatc aaaggcaaat   1560
actcaaaaaa cagaaaaaaa tagccccaca caaccgaaaa aaccagaggt ttcactagct   1620
aaaacaacag aaaattcagc aaaaacagtc aaggtaagca cttttgcaga agaagctaag   1680
ggtcaaagtc aaagtcagca aacacaacca gtttccactt catcgcctca aactagtcaa   1740
aattcacttc ctaattccac aagcagctca aattctgtat tagaaaatga aaaatttggg   1800
acaagcattt gaacagcttt taatttcgct aatatttata atcttgaaaa tacaaaaagc   1860
gaatatgaga tctcaacttt aggaaataag ctattttttg attttaaatt agttgataaa   1920
actaatcaaa atcaattttt ggctcagtcc aaaattagtc ttaataatat tattaattct   1980
aataaatctg cctatgatat aattaagaaa ttcaatcccg atgtgttttt agatggaaca   2040
attaattatc aaaatcaagg aaaagataaa aaagaattta tcctaaaaga tttaagtgat   2100
aataaattaa tatttaaatc agaagatgca attcaaactg atcaaggttt agagctaaag   2160
aaacctttga aattacagtc aaaatcgtct aatccagaaa aagaaatatc aacttcttta   2220
tataccggag caatttattt agtttttgat gcaaaaaata tttccgatgg taattggatt   2280 aatctttttag ccgatagaaa aggaaaaggg cttgtaatta aagttcaaaa ttcaaataat   2340
aatgtaccta aaaccaaaga aattgttgag aatggtacct attttatatga aattcttgct   2400 ggcaaggatt cgattaaggt aaattcttat ttttttccaa caaagtaccc aaaacgtgta   2460
aaacgtctta aattcgagat taaccctaaa gacaccttgc caaatttctt tactttagaa   2520
tgatttcatc ttgattggta tcaaatcggc ccaggcgaac aaaataaaaa accacaacaa   2580
aacgctaaaa aagaacctac aattatatta aaaacgctgg caatatttaa tgataaatca   2640
tttgcagaga aaggaagttt aacaaaaaga agtgaattaa ttaacgggtt gattagaaac   2700
tatgttaaaa agtaa                                                    2715
```

<210> SEQ ID NO 13
<211> LENGTH: 3159
<212> TYPE: DNA
<213> ORGANISM: Mycoplasma hyopneumoniae

<400> SEQUENCE: 13

```
atgagtaaat tgacaaaatc gaaaactttt aaaattggtt tggttgggtc tattattggt    60
cttggagttt ttggtctaac tgtcggactt agcagcttgg caaaatacag atcagagcat   120
ccgcggaaag ttgtaaatga ttttgctaca aaagtttcaa ctttatcctt tagtccggat   180
gcttttttg ctaattctga ctattgaaca atcaaaaatc accttttaga ttccaagaac    240
caaatcaaaa atagcgaaaa ggttctaaaa tccttttcct tttttctaa aaacggtgat    300
cagttagaaa aaattaacct tgaagatcca gaatataaaa atgccggaat tcctttcat    360
attcttgaaa ttatccctga tgatgtcaat caaaattta aagtcaaatt tcaattatga    420
caaaaatttg caaacgggga tatagcaaaa tctgatattt atcaagaaga agtgtcgct    480
tttataaagc agtcaaatct tttagttgcc gaatttaatt tttcacttaa gaaaatcact   540
gataaattaa atcagcaagt aggaaatcta tccctaaaat ctacaaattt tgccgatgat   600
ttagcaaagt taacaaaacc gacatcctct tataaaaatc cggcaagttt tcgtgtactt   660
gattttcaag aagatctaaa tcaggcacga aattccgaag aattagtcaa aaaacttgct   720
atttattttc cttcacttga taatttaata acaaagctaa atgaatcttc agaaaataaa   780
ctacccggaa attctgggca tattttcgaa tttagtcttc gcaaatcaca ggcaactaat   840
caatatgtca gcgttcagaa ccaaattcca tttctatttt tagaagcaga tcttagtcaa   900
agtgctcgtg atttaattgg tcaagatttt aattttcgcc aatagtttc atcaattaaa   960
ctacaaaaac aagacaattc ctcctacttt ttagatttta atcagttttt aggcaactta  1020
aagttaaaag atattagcaa aactgatttt aatgagcaag gtttaaaaac ttcggcctat  1080
gaaattctta gtacaattag gtctggtttt tttgataata acgatcttcg ttctgatcaa  1140
gccaaagaat caattaataa aatattaaaa aataaaatta aatttgattt tggcaagtta  1200
gatgcaattt tttctgacaa gggaaattct gaaagtcttc aatattatct agatgtaaaa  1260
aaggcaagtc ttgataaaac tgataaatca acaatttttaa ttccttttcg tctaaaagtt  1320
gatgaaagtt ttttcaaaac ttcaactaat ttaccagaga atatcattgc tcgaaaagat  1380
ggaatttta aactaaccgg atttgaccaa gggctaaata atcaacttcc aaaaataaat  1440
caagaaattt ataaaacaaa atatttatca tttttcgaaa aaggtaagga aaatcaagat  1500
ttagttgatt ttgggagtga accgataaat ggtcctcttt taatttctaa agttgaagcc  1560
gatgcacttt ttaaagaaaa caaaccagaa gcaattcata agtacttga actaattat    1620
aattatcaat ttaatcctta tcagtcttta cttgattctt gaacaggaaa tttagtacag  1680
ccaaaacttg aaaacattaa agctttaaat gaaaatgaaa aagcggcagt atccgaagcc  1740
ggaattgctg aaatttatc acgtgatttt tttctagatg gcatcaagt tgctagtttt    1800
tatcaggatt tactaacaaa agatcggcta acagttatcg aaactcttta tgaattaggt  1860
aaaaaatggg gccttcatac aaatacagct aatttcccac gctgaaaatt tagaaatgca  1920
aaaaacattt tcgaggaagc aacacagtat aaaattcctac tgggtaaaaa aggtaaagaa  1980
aattttagaa aaataaccaa acttactttt aatggtttat atcgcaatga aaaaggtcaa  2040
ggattttatg ctactttagt tctgccaaaa gaaattaagg ataaattagc aaataaaact  2100
gatgctgagg ttttttgcaga attaaaaaaa cattctttaa ttgattcttc cgggtttaaa  2160
actataaata ttgacaaaaa tcttttagaa ggggaagact tgaaaatttt tggtgattta  2220
ttaaaagctt ttttccttaa agctgcccaa tttaataatt ttgctccttg agcaaaatta  2280
```

```
gatgataatc ttaaatattc gtttgtgccg aaaaaaggag atcaagaaaa agagggcaaa    2340
aaagctgaaa ttgataaaaa agttaaggaa ttaacagata aaattagttc accggggtca    2400
gttctgccaa aatcagaagc aggtaaaccc gtggcggcta aaccagaagc tgcaaaacct    2460
tcaagctcaa caacaagttc agtttcctcg gcttcattag aaggaaatta tcttccaatt    2520
tcatttgaat ttaaactttc ttatcgtgat ggagcaaaat cggagttaaa aacaccggaa    2580
attaaagtat ttttagaact tcagaccgat aaagattatc aagaaaataa aattatcaaa    2640
gaattagata aaacggtatt agaactccaa agcgaattta agaatgaag  attagatgag    2700 tctgcatttt cttctttaac ttttcctaaa agccaaaaaa gtgaaggaac tcaaaatcaa    2760
ggtaaaaaag ccgaaggtgc tcctaaccaa tctaaaaaat cagagaaaa  tagcaataag    2820 ctaacagaat atattcaaga attaggtaca aaagtagaaa atcccttaa  atcaaaagga    2880 aaaaactact ctgctgaggt tgaaaaaatt atagaagcat tttctggggg atataaattc    2940
cttgactttg cattagtaga acaaactcca aaacctgaaa ctccaaaaac agaagcagca    3000
aagcctgaaa ctacaaaacc agttgccgcc cgtcctgagg cagcaaaagt tgctgccaaa    3060
ccttcagcgg ccaagcccgt tagttcccca gcgccaaaaa aatcaacact ttatgttcgc    3120
gttctcatta gaaaaaaga aaataaacaa gtcaaataa                            3159

<210> SEQ ID NO 14
<211> LENGTH: 4233
<212> TYPE: DNA
<213> ORGANISM: Mycoplasma hyopneumoniae

<400> SEQUENCE: 14
atgaagaaac aaattcgcaa caaagcaata atcgttctag caggtcttag ttttattggg      60
ataaccgcgg gagtgggtct ggctgttcaa aattcagcgc ttagatcctc ttatcttaat     120
caatttaaaa atgataaatc tgcaactgaa ttattgtcac aataaatga  tactgaatta     180 tccaagataa tcagtaattt tagcttaaaa gaaaactgaa gtaaaatatc agctggtcaa     240
gcttttgaac tccataaaaa tcctttatat gcctttaaat taacagatgc aatcgatttt     300
tccaaaatcg ataagaaatt cgcgcatcta ttttttaatg ttcaggttaa tgataatact     360
aaagttgaag gtaattcaat tagaaattta actgttttg  tttttgatgc aattacaaaa     420
aaagaagtcg ctactcgagc ttttcataca agtcttagtg ggttttcaag tgttgcaaaa     480
gaagatttta tcgaaaattt cgttgctgaa tcttcaactt acgaacttga taaagatcaa     540
ttaaagaaaa attttgctac cgaaatagtt ctaccttcag ctttttctat aaattccaa     600 gatgttttac taactcatct aagaaaaact tccccagaaa gttttcaaga aacaaaaact     660
atccaagtta gagcactaac taattcaatt actgagtttc aacaacaaca acaagagggc     720
ggatctggag gatctgggac atctggggga tccagtgggg gaagttcttc aggttcaaca     780
gatcaaaaag ggcaaacaag tcaaagctca gaaaaggaat ctaagtccga aaggaaaaa     840 ggaaaagatc agcaaagcac tcaaggctca gaacaaaaac aagatcaaaa gcaacagaag     900 cctaagaag  cagaaagcc agctcaagaa aaaccagctc aagaaaagcc agctgagaca     960
ccaaaagtta agccccagt tattgagcct gtgaaaaaat tagtatttga aaatgaaaaa    1020
ttaaatcaag cattacttga gacactaaaa gatttggtg  gccttaaatt actagcggct    1080
tccggacttc aaggcttatt accaaatgaa tatactttat taccagtttc ttctgataaa    1140
tcattaataa aacttgatat agatgaccag gcaggaacag catcaattca tcttaaatta    1200
ttagataaaa ataagaagga aaaaaatcta atcctgccaa taaacgggct tgcttcaatt    1260
```

```
ggtgcgatca aagataaagt gtttagccag atatttagaa accagaatgc ttatttaact      1320
ataagacctc agattaatga atatctaaga aaaaatccta gaaaaaaaat tcaggaagta      1380
atttgaagtt tttcaaggga aaaatttgat caactccgtg gcaaaatga  agtagaaaaa      1440
ttcttagagg aactttataa tccaacccag acaagccaaa gccctcagaa aagtaaaagt      1500
tctgattctg cgaaaaacaa tgtagcaaca attcaagctt caccagagac agcaccaaaa      1560
acaacaacaa caaattctaa tacccagtca agttctactt caacaaataa tcaatcttct      1620
aatggtagcc aacaaatggc aagtcctcaa actgaatcct cacttagtac tgcgaagacc      1680
tcagaggcaa gtaattcttc tgaagaatct agttcagaga ccaaagggac aaaagagcaa      1740
gctaactcag agacaaaccc aatgggaaaa tcccaggcaa accggaagc  aaaaccagag      1800
gaaaaacaaa ttaatttaga ggatcaagca aaaacagagc taaagaaaat tctaaaaatt      1860
catggttgaa attatagaac acttttaaaa gatcaaaacc aaaaagtaat tcttcctgat      1920
aatattaatt tttggtttga tcttagaaat aaaagatcat cttatgaaaa ttataaatta      1980
gaatttgatc ttgttaaaaa aacaggtcag attcaagcag gtgatgtaat tgatgcaaat      2040
aaaatccgcc ttaatttaaa aattagtcct ctagctaatc ttaaattaga agtagattca      2100
aaaaataaac aatatattga cgccggacaa ataggcgact atgttgaatt tgacaaacaa      2160
gggaaaaaac tagtagagca agggaaatct ttagatctta agttggagc  ttcagctgca      2220
aattcaatat ttagtccaga aattcgttat tcagcttatg aattaaaggg ttgaacttat      2280
ccaattgata ttgatattaa aggaaatcca attcaacaag aacttgaaaa attagttggt      2340
aattttcaca agttggaat  taataaaaat aatcaatacc aaatttattc aacagacatt      2400
gacaagattt ttgctcaagc taaacttgat aaatattttg agctaagtca agaagaaaaa      2460
caagcctcaa aaaatatctt tcaagaaaaa cttaatccaa ttagtgaaat aaccattgta      2520
aaactccctc caaagaaga  agttcttccc ccactagaag aagagaaaaa accagagcag      2580
gaccaaaaag cacaagaaaa acaagaagat aaacaaaacc aaaaacaaca agaaaaacaa      2640
gaagataaaa aagaacaaga ccaacaaaaa cattctcaaa gccctgacca aaaaactgaa      2700
actcaaactc atgaccaaga aaaagataaa caaactagct cagaaactag tccttcaaat      2760
actaatgagt cttcagggac acaaaatact gctcaaaatt cccagacaaa tcaggcaaat      2820
tctggacaag gtcaaagcca acaagcagca tcatcttcaa cttcatacca aactcacaaa      2880
ataacaactt tccaagatga tcaaaaagat caaactaatg aacaaacaga aaagaaatt      2940
gaacctgaaa aattagcctt tggtgattat cttgttaaat atcttgatat ttttgaaact      3000
tttaaagttg gcccagatca gaaattatca attggtagat gatataatgc gccccaaaga      3060
acttataatg ttatattccg ggtacttgat aaggaaaata ttcaagtagc tgcatcccctt      3120
ttccaattac atggtatatc agcaactaat attgcccttg aaaaatcact tcgttatgct      3180
cctgatattt tccttgatgg aacttccggt cttgaatata aacaagatac aggggacaag      3240
ccatatcttc aaggaaggca atttgtttcg gcaattaatt caattaataa tactaaatct      3300
tcctatcggg tacataaact ttttgataat ctacctttat cagaagaatc aagtcagggt      3360
ctaagactta atcttcact  tgtttatgac tatcaaaaaa atgatcctta actttccag       3420
gcatccaaag aagctctaag aaaaactgca cttactaaag gagttttata tttagcattt      3480
aaacctgaac aaattttagg aataaaagga tcaaagacag ctccaggaag aaactataaa      3540
cttttatcaa caaccaatgt tcattttaaa tctttatatg gactctctaa tcttgaacta      3600
```

-continued

```
gtaaaaacca aataccaaga aaaccttaaa ttagtctgaa aactaatcgg ggcaaaacca   3660
gttaatgatg ataagatctt acctccacaa gtagcagatc ttcctagaca tagatcaact   3720
gagattattc ttttagaaga ttcaaaacca ggtgcatctt catcgcctca aactaaagaa   3780
aatagccaaa ataaagaagc tgagaccttc aatttagata ttagacaaac taaaccaaat   3840
cagatcgaac cacttgaaca ttatcttggt caaacttgat taatggaaat aagaattgat   3900
gatgaaagtg caacaattac gataattcct gaacaacaag aaagagaaga tagcaaacta   3960
aaagtttgaa aatccgaaat taagatcaaa gataaaaata aataccaaaa ccaggataca   4020
aactgagaaa ccgagctagc ttctgtttta ggtagaggat ttgactatgg acagatcggt   4080
gatacaaccc cacaagcttc taatccccaa gaccgagtgg gtatgacctt taaagggttt   4140
gccgtattta aaggcgataa actcttaaat gataaagcaa gactaaatgt gcgcaaagcc   4200
tttatggatc aatattttaa gaattattct tag                                4233
```

<210> SEQ ID NO 15
<211> LENGTH: 5757
<212> TYPE: DNA
<213> ORGANISM: Mycoplasma hyopneumoniae

<400> SEQUENCE: 15

```
atgaaaaaca aaaaatcaac attactatta gccacagcgg cggcaattat tggttcaact     60
gtttttggga cagttgttgg cttggcttca aaagttaaat atcggggtgt aaatccaact    120
caaggagtaa tatctcaatt aggactgatt gattctgttg catttaaacc ttcgattgca    180
aattttacaa gcgattatca aagtgttaaa aaagcacttt taaatgggaa aacctttgat    240
ccaaaaagtt cagaatttac tgattttgtc tcaaaatttg actttttgac taataatggg    300
agaaccgttt tggagatccc gaaaaaatat caggtggtta tctcggaatt tagccccgag    360
gatgataaag aacgttttcg tcttggattt catctaaaag aaaaacttga agatggaaat    420
atagctcaat cagcaactaa atttatttat cttttaccac ttgatatgcc caaagcggcc    480
ctgggtcaat attcttatat cgttgataaa aattttaata atttaattat ccatccttta    540
tctaattttt ctgctcaatc aataaagccg cttgcactga cccgttcaag tgattttata    600
gcaaaactta atcagtttaa aaatcaggac gaactttgag tttatcttga aaaattcttt    660
gatcttgaag ctctaaaagc aaatattcgt ttgcagacag ccgattttag ttttgaaaaa    720
ggcaatttag ttgatccttt tgtttattct tttattagaa atccgcaaaa tggaaaagaa    780
tgagctagtg atcttaatca agatcaaaaa accgtcagac tttatcttcg aaccgaattt    840
agtcctcagg ctaaaaccat tttaaaagac tataaataca aagatgagac tttcttaagt    900
agtatcgatt taaaagcaag taatggaact agtttatttg ctaatgaaaa tgatctaaaa    960
gatcaattag atgttgatct tttagatgtc tctgattatt ttggaggcca atcagagaca   1020
attactagta attcccaagt taaacctgtc cctgctagtg agagatcttt aaaagatcgg   1080
gttaaattta aaaaagatca gcaaaaacca agaattgaga aatttagttt atatgaatat   1140
gatgctctaa gtttttattc ccaacttcag gaattagttt ctaaacctaa ttcaattaaa   1200
gatttagtta atgcaacttt agctcgtaat cttcggtttt cattaggaaa atataatttt   1260
ctttttgatg atttagccag tcatcttgat tatacttttt tagtttcaaa agcaaaaatt   1320
aaacaaagtt caattacaaa aaaattattc attgaattac caatcaaaat tagtcttaaa   1380
tcttcaattt taggtgatca agaacctaat attaaaactt tattcgaaaa agaagtaact   1440
tttaaattag ataacttccg tgatgttgaa atcgaaaaag cttttggact tttatatcca   1500
```

```
ggtgttaatg aagaacttga acaagcccga agagagcaaa gagcaagttt ggaaaaagaa    1560
aaagcgaaaa agggtcttaa agaatttagc cagcaaaaag atgagaattt aaaagcaata    1620
aataatcaag atggtcttga agaagatgat aatattactg aaagacttcc tgagaattcc    1680
ccgattcaat atcagcaaga aaaggccggt ttaggttcaa gtccggataa accttatatg    1740
ataaaggatg tccaaaatca acgttattat ctagcaaaat cacaaattca agaactaatt    1800
aaggccaaag attataccaa attagccaaa ctttttatcca atagacatac ttataatatt    1860
tctttaagat taaagaaca acttttgaa gtaaatccaa gaattccaag ctctagagat      1920
atagaaaatg caaatttgt tctagataaa accgaaaaaa ataaatactg gcagatttat     1980
tcaagtgctt ctcctgcttt ccaaaataaa tgatcacttt ttggatatta ccgttattta    2040
ttaggtcttg atccaaaaca aacaatccac gaattagtaa aattaggaca aaaagcgggt    2100
tcaagtgctt ctcctgcttt ccaaaataaa tgatcacttt ttggatatta ccgttattta    2160
ttaggtcttg atccaaaaca aacaatccac gaattagtaa aattaggaca aaaagcgggt    2220
cttcaatttg aaggatatga aaatcttcct tctgatttca atcttgaaga tcttaagaat    2280
attaggatta aaacaccttt atttagtcaa aaagataatt tcaaattatc tttacttgat    2340
tttaataatt attatgatgg tgaaattaaa gccccagaat ttggtcttcc tttatttta    2400 ccaaaagaat taagaaaaaa tagttcaaat attggtagtt ctcaaaactc taatagccct    2460
tgagaacaag aaattattag ccaatttaaa gatcaaaatc tatctaatca ggatcagtta    2520
gcccagttta gtactaaaat ctgggaaaaa atcattggtg atgaaaacga atttgatcaa    2580
aataacaggc ttcagtataa acttttaaaa gatcttcaag aatcttgaat taacaaaact    2640
cgcgataatc tttattggac ttatctaggt gataaactta agttaaaacc aaaaaataat    2700
ttagatgcta aatttagaca aatttccaat ttacaagagc ttttaactgc tttttatacc    2760
tcagctgctc tttctaataa ctgaaattat tatcaagatt caggggcaaa gtcaactatt    2820 attttgaag aaatagctga gctagatcca aaagtaaaag aaaaagtagg agctgatgtt     2880
tatcaattaa aattccatta tgcaatcggt tttgatgata atgctggcaa gtttaatcaa    2940
gaagtaattc gttcttcaag tagaacaatt tatcttaaaa cctcagggaa atccaaatta    3000
gaagcagata caattgatca acttaatcaa gcagttgaaa atgcaccttt aggtcttcaa    3060 agttttatc ttgatactga aagatttggg gttttccaaa aattagcaac ttccttagca     3120
gttcaacata aacaaaaga aaaaccacta cctaaaaaac taaataatga tggctatact     3180
ttaattcatg ataaacttaa aaaaccagta attccccaaa ttagttcaag tcccgaaaaa    3240
gattgatttg aaggtaaatt aaatcaaaac gggcaaagcc aaaatgtaaa tgtctcaact    3300
tttggttcaa taatcgagtc cccttatttt agtactaatt tccaagaaga agctgattta    3360
gaccaagaag gacaagatga ttcaaaacaa ggaaataaga gcctagataa tcaagaagca    3420
ggtcttttaa aacaaaaact ggcaatttta ttagggaatc aatttatcca atattatcaa    3480
caaaatgata agaaattga attcgagatt atcaatgttg agaaagtttc agagcttagt    3540
ttccgcgttg aatttaaatt agcaaaaact cttgaagaca acggaaaaac tattcgagtt    3600
ttatcagatg agacaatgtc attaattgtt aatactacaa ttgaaaaagc accagaaatg    3660
agtgctgctc ccgaagtatt cgatactaaa tgggttgagc aatatgatcc aagaaccccg    3720
cttgcggcta agacaaagtt tgtcttaaaa ttcaaagatc aaataccagt tgatgccagc    3780
ggaaatattt ctgataaatg actagcaagt attcctttgg tgattcacca gcaaatgttg    3840
```

```
cgtcttagcc cggtagttaa acaataagaa gagcttggtc taaaaactga acaacaacaa   3900
caacaacaac aacaacaaca aaagaaagct gttagaaaag aagaagaact ggaaacctat   3960
aatccaaaag acgagtttaa tattcttaat cctttaacaa aagctcaccg tcttaccta    4020
tcaaatttag taaataatga tccaaattat aaaattgaag attaaaagt aatcaaaaat    4080
gaagcaggtg atcatcaatt agaattttct ctaagagcta ataatatcaa aagattaatg   4140
aatacaccaa ttacttttgc tgattataat cccttttct attttaatga ggactgaaga    4200
aatatagata aatatttaaa taataaagga aatgtgagtt ctcaacaaca acaacaacaa   4260
caacaacaac caggcgggg taatcaaggc tcgggtctaa tccaaagact aataaaaat     4320
attaagcccg aaacttttac ccccgcactc atagctctta aacgagataa taatactaat   4380
ctttctaact attctgataa aataataatg atcaaaccaa atatttggt tgaacgatca    4440
attggtgttc cctgatcaac cggccttgat ggttatattg gttcagaaca actcaagggc   4500
ggaacttcct caaacggtca aaagcgattt aagcaagatt ttattcaggc tttaggtctt   4560
aaaaacactg aatatcatgg taaactaggt ctttcaatta gaattttga tcctggaaat    4620
gaactagcaa aaattaagga tgcttcaaat aaaaaagggg aagaaaaaact gttaaaatca   4680
tatgatttat ttaaaaacta tttaaatgaa tatgagaaaa aatccccta aattgctaag    4740
ggatgaacaa atattcatcc tgatcaaaaa gaatatccaa atccaaatca aaaactacct   4800
gaaaattatc ttaacctagt tttaaatcaa ccttgaaagg ttactttata taattcaagt   4860
gatttatta ctaatttatt tgttgaacct gaaggctcag atcggggatc tggagcaaaa    4920
ttaaaacaag taatccagaa gcaagttaat aataactatg ctgactgggg gtctgcatat   4980
ctcacgttct ggtatgataa agatatcatt accaatcagc caaatgttat aactgctaac   5040
attgctgatg tctttattaa agatgtaaag gaacttgaag ataatacaaa actaattgct   5100
ccaaatatta ctcaatgatg gccaaatatt agcggctcaa aggagaaatt ttataagcca   5160
acagtgttt ttggtaattg agaaaatgaa acagcaata tgaattccca ggggcagacc    5220
cctacctggg agaagatcag agaaggattt gctctccaag cgcttaaatc cagctttgat   5280
caaaaaacaa ggacatttgt ccttacaaca atgctcctt tacctttatg aaaatacgga    5340
ccattaggtt tccaaaatgg gccgaatttc aaaacacaag attgaaggct tgttttccaa   5400
aatgatgata accaaatagc cgcgctaaga gtccaggagc aagatcgccc agaaaaatca   5460
agcgaagata aagacaagca aaaatggatt aaatttaaag ttgttatccc tgaagaaatg   5520
tttaattccg gtaatatacg ttttgttggg gtaatgcaga tccaaggtcc taatacttta   5580
tgacttccag tgattaattc ttcggttatc tatgacttct atcgcggaac aggagattct   5640
aacgatgtcg ccaatcttaa tgtagctcct tgacaggtta aaacaatcgc atttacaaat   5700
aacgccttta ataatgtttt caaagagttt aatatctcta aaaaaatagt agaataa      5757
```

<210> SEQ ID NO 16
<211> LENGTH: 3279
<212> TYPE: DNA
<213> ORGANISM: Mycoplasma hyopneumoniae

<400> SEQUENCE: 16

```
atgagtaaaa aatcaaaaac atttaaaatt ggtttgactg ccggaattgt tggtcttgga    60
gttttggcc taactgtcgg acttagcagc ttggcaaaat acagatcaga aagcccacga    120
aagattgcaa atgattttgc cgcaaaagtt tcaacattag cttttagtcc ttatgctttt   180
gagactgatt ctgattataa aatagtcaaa aggtgactag ttgattctaa taacaatatt   240
```

```
agaaataaag aaaaagttat tgattccttt tccttttta  ctaaaaacgg tgatcagtta    300
gaaaaaatta attttcaaga tcctgaatat accaaagcga aaataacttt tgagattctt    360
gaaattatcc ctgatgatgt caatcaaaat tttaaggtaa aatttcaggc attacaaaaa    420
cttcataatg gtgatattgc caaatctgat atttatgagc aaacagttgc ttttgccaaa    480
cagtcaaatc ttttagttgc cgaatttaat ttttcgctta aaaaaattac cgaaaaatta    540
aatcaacaaa ttgaaaattt atcaacaaaa attacaaatt tgctgatgac aaaaacaagc    600
agccaaaaag atccctcaac tctaagagct attgatttcc aatacgattt aaatacagcg    660
cgaaatgctg aggatttaga tataaagctt gctaattatt ttccagtact taaaaattta    720
ataaacagac taaataatgc tcctgagaat aaattaccta ataatttagg taatattttt    780
gaatttagct ttgcaaaaga tagttcaact aatcaatatg taagtatcca gaaccaaatt    840
ccttcgctgt ttttaaaagc agatcttagt caaagtgccc gtgaaatttt agctagccca    900
gatgaagttc agccagttat taacatttta agattaatga aaaagataa  ttcttcttat    960 tttctaaatt ttgaggattt tgttaataat ttaacactga aaatatgca  aaaagaagat    1020 ttaaatgcaa agggtcaaaa tctttctgcc tatgaatttc tagcagatat taaatctgga    1080 ttttccctg  gagacaagag atccagtcat accaaggcag aaattagtaa tctttaaat    1140 aaaaagaaa  atatttatga ctttggtaaa tacaatggaa aattcaacga ccgtcttaac    1200
tcgccaaatt tagaatatag cctagatgca gcaagcgcaa gtcttgataa aaaagataaa    1260
tcaataattt taattcccta ccgccttgaa attaaagata aatttttttgc cgatgattta    1320 tatccagata caaaagataa tattcttgta aaagaaggga ttcttaaatt aactggattt    1380
aaaaaaggtc caaaaattga tctccctaat atcaatcagc aaattttaa  aaccgaatat    1440 ttaccatttt ttgaaaaagg taagaagaa  caagcaaaat tagactatgg taatatctta    1500
aatccatata atactcaact tgccaaagtt gaagttgaag ctctttttaa agggaataaa    1560
aaccaagaaa tctatcaagc acttgatgga aattatgcct atgaattcgg ggcctttaaa    1620
tccgtgctta ttcctgaac  aggaaaaatt cagcatcctg aaaaagctga tatccaaaga    1680
tttacaagac atttagaaca agttaaattg ggttctaatt cagttttaaa tcaaccacaa    1740
acaacaaaag aacaagtaat ttcaagtctt aaaagtaata actttttaa  aaatggacat    1800 caagttgcta gttatttcca ggatttactc accaaggaca aattaacagt tctagagact    1860
ctttatgatc tagcaaaaaa atggggacta gaaactaaca gggcgcaatt cccgaaagag    1920
gttttccaat atacaaaaga tattttttgca gaagcagata aattaaaatt tttggaaggg    1980
aaaaaaaagg atccttacaa tcagataaaa gaaattcacc aactttcctt taatattta    2040 gctcgtaatg atgtaataaa atctgatgga ttttacggag ttttattatt gccccaaagt    2100
gtaaaaactg aattagaagg caaaaatgag gcgcaaattt ttgaagctct taaaaaatat    2160
tctttaattg agaactcggc ttttaaaact actattttag ataaaaatct acttgaaggg    2220 actgattta  aaaccttcgg tgatttttta aaagcatttt tccttaaagc agcccaattt    2280
aataattttg ctccttgagc aaaattagac gataatcttc agtattcatt tgaagctatc    2340
aaaaaagggg aaactacaaa agaaggtaaa agagaagaag tagataaaaa agttaaagaa    2400
ttagataata aaataaaagg tatattacct cagcccccag cagctaaacc tgaagcggct    2460
aaaccagtag cagcaaaacc tgaagcagct aaacctgaaa caacaaaacc agtagcagct    2520
aaacctgaag cagcaaaacc agtagcagca aaaccagtag cagcaaaacc agttgctact    2580
```

| | | |
|---|---|---|
| aatactaata ctaatactgg cttttcactt acaaataaac caaagaaga ctatttccca | 2640 | |
| atggcttttta gttataaatt agaatatact gacgaaaata aattaagcct aaaaacaccg | 2700 | |
| gaaattaatg tatttttaga actagttcat caaagcgagt atgaagaaca aaaaataata | 2760 | |
| aaggaactag ataaaactgt tttaaatctt caatatcaat tccaggaagt caaggtaact | 2820 | |
| agtgaacaat atcagaaact tagccaccca atgatgaccg agggatctcc taatcaaggt | 2880 | |
| aaaaaagccg aaggcgctcc taaccaaggc aaaaaagccg aaggcgcacc tagtcaaggg | 2940 | |
| aaaaaagccg aaggcgctcc taaccaaggc aaaaaagccg aaggcgcacc tagtcaaggg | 3000 | |
| aaaaaagcag agggtgcttc taatcaacaa agcacaacta ccgaattaac taattacctt | 3060 | |
| cctgaattag gtaaaaaaat tgacgaaatc attaaaaaac aaggtaaaaa ttggaaaaca | 3120 | |
| gaggttgaac taatcgagga taatatcgct ggagatgcta aattgctata ctttgtccta | 3180 | |
| agggatgatt caaaatccgg tgatcctaaa aaatcaagtc taaaagttaa ataacagta | 3240 | |
| aaacaaagta ataataatca ggaattaaaa tctaaataa | 3279 | |

```
<210> SEQ ID NO 17
<211> LENGTH: 14
<212> TYPE: PRT
<213> ORGANISM: Porcine reproductive and respiratory syndrome virus

<400> SEQUENCE: 17

Ser Ser Ser Gln Leu Gln Ser Ile Tyr Asn Leu Thr Ile Cys
1               5                   10

<210> SEQ ID NO 18
<211> LENGTH: 603
<212> TYPE: DNA
<213> ORGANISM: Porcine reproductive and respiratory syndrome virus
<220> FEATURE:
<221> NAME/KEY: CDS
<222> LOCATION: (1)..(603)

<400> SEQUENCE: 18
```

| | | |
|---|---|---|
| atg ttg ggg aaa tgc ttg acc gcg ggc tgt tgc tcg caa ttg cct ttt<br>Met Leu Gly Lys Cys Leu Thr Ala Gly Cys Cys Ser Gln Leu Pro Phe<br>1               5                   10                  15 | 48 | |
| ttg tgg tgt atc gtg ccg ttc tgt ttt gct gcg ctc gtc aac gcc agc<br>Leu Trp Cys Ile Val Pro Phe Cys Phe Ala Ala Leu Val Asn Ala Ser<br>            20                  25                  30 | 96 | |
| agc agc agc agc tcc caa ttg cag tcg att tat aac ctg acg ata tgt<br>Ser Ser Ser Ser Ser Gln Leu Gln Ser Ile Tyr Asn Leu Thr Ile Cys<br>        35                  40                  45 | 144 | |
| gag ctg aat ggc aca gat tgg ctg aat aaa aat ttt gat tgg gca gtg<br>Glu Leu Asn Gly Thr Asp Trp Leu Asn Lys Asn Phe Asp Trp Ala Val<br>    50                  55                  60 | 192 | |
| gag act ttt gtt atc ttt cct gtg ttg act cac att gtc tcc tat ggc<br>Glu Thr Phe Val Ile Phe Pro Val Leu Thr His Ile Val Ser Tyr Gly<br>65                  70                  75                  80 | 240 | |
| gcc ctc acc acc agc cat ttc ctt gac gca gtc ggt ctg atc act gtg<br>Ala Leu Thr Thr Ser His Phe Leu Asp Ala Val Gly Leu Ile Thr Val<br>                85                  90                  95 | 288 | |
| tct acc gcc gga tat tac cac ggg cgg tat gtc ttg agt agc gtc tac<br>Ser Thr Ala Gly Tyr Tyr His Gly Arg Tyr Val Leu Ser Ser Val Tyr<br>            100                 105                 110 | 336 | |
| gct gtc tgc gcc ttg gct gcg ctg att tgc ttc gtc att agg ttg acg<br>Ala Val Cys Ala Leu Ala Ala Leu Ile Cys Phe Val Ile Arg Leu Thr<br>        115                 120                 125 | 384 | |
| aaa aac tgc atg tcc tgg cgc tac tca tgt acc aga tat acc aac ttt<br> | 432 | |

```
                Lys Asn Cys Met Ser Trp Arg Tyr Ser Cys Thr Arg Tyr Thr Asn Phe
                    130                 135                 140 ctt ctg gac tcc aag ggc aaa ctc tat cgt tgg cgg tca ccc gtc atc        480
Leu Leu Asp Ser Lys Gly Lys Leu Tyr Arg Trp Arg Ser Pro Val Ile
145                 150                 155                 160 ata gag aaa ggg ggt aaa gtt gag gtt gat ggt cat ctg atc gac ctc        528
Ile Glu Lys Gly Gly Lys Val Glu Val Asp Gly His Leu Ile Asp Leu
                    165                 170                 175 aag aga gtt gtg ctt gat ggt tcc gcg gca acc cct gta acc aaa gtt        576
Lys Arg Val Val Leu Asp Gly Ser Ala Ala Thr Pro Val Thr Lys Val
                180                 185                 190 tca gcg gaa caa tgg tgt cgt ccc tag                                     603
Ser Ala Glu Gln Trp Cys Arg Pro
            195                 200

<210> SEQ ID NO 19
<211> LENGTH: 200
<212> TYPE: PRT
<213> ORGANISM: Porcine reproductive and respiratory syndrome virus

<400> SEQUENCE: 19

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
                20                  25                  30

Ser Ser Ser Ser Ser Gln Leu Gln Ser Ile Tyr Asn Leu Thr Ile Cys
            35                  40                  45

Glu Leu Asn Gly Thr Asp Trp Leu Asn Lys Asn Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr Val Leu Ser Ser Val Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
                180                 185                 190

Ser Ala Glu Gln Trp Cys Arg Pro
            195                 200

<210> SEQ ID NO 20
<211> LENGTH: 582
<212> TYPE: DNA
<213> ORGANISM: Porcine circovirus
<220> FEATURE:
<221> NAME/KEY: CDS
<222> LOCATION: (1)..(582)

<400> SEQUENCE: 20 atg aat ggc atc ttc aac acc cgc cta tcc cgc acc ttc gga tat act        48
Met Asn Gly Ile Phe Asn Thr Arg Leu Ser Arg Thr Phe Gly Tyr Thr
```

```
1               5                  10                    15
atc aag cga acc aca gtc aga acg ccc tcc tgg gcg gtg gac atg atg      96
Ile Lys Arg Thr Thr Val Arg Thr Pro Ser Trp Ala Val Asp Met Met
             20                  25                  30 aga ttc aat att aat gac ttt ctt ccc cca gga ggg ggc tca aac ccc     144
Arg Phe Asn Ile Asn Asp Phe Leu Pro Pro Gly Gly Gly Ser Asn Pro
             35                  40                  45 cgc tct gtg ccc ttt gaa tac tac aga ata aga aag gtt aag gtt gaa     192
Arg Ser Val Pro Phe Glu Tyr Tyr Arg Ile Arg Lys Val Lys Val Glu
 50                  55                  60 ttc tgg ccc tgc tcc ccg atc acc cag ggt gac agg gga gtg ggc tcc     240
Phe Trp Pro Cys Ser Pro Ile Thr Gln Gly Asp Arg Gly Val Gly Ser
 65                  70                  75                  80 agt gct gtt att cta gat gat aac ttt gta aca aag gcc aca gcc ctc     288
Ser Ala Val Ile Leu Asp Asp Asn Phe Val Thr Lys Ala Thr Ala Leu
                 85                  90                  95 acc tat gac ccc tat gta aac tac tcc tcc cgc cat acc ata acc cag     336
Thr Tyr Asp Pro Tyr Val Asn Tyr Ser Ser Arg His Thr Ile Thr Gln
             100                 105                 110 ccc ttc tcc tac cac tcc cgc tac ttt acc ccc aaa cct gtc cta gat     384
Pro Phe Ser Tyr His Ser Arg Tyr Phe Thr Pro Lys Pro Val Leu Asp
             115                 120                 125 tcc act att gat tac ttc caa cca aac aac aaa aga aac cag ctg tgg     432
Ser Thr Ile Asp Tyr Phe Gln Pro Asn Asn Lys Arg Asn Gln Leu Trp
 130                 135                 140 ctg aga cta caa act gct gga aat gta gac cac gta ggc ctc ggc act     480
Leu Arg Leu Gln Thr Ala Gly Asn Val Asp His Val Gly Leu Gly Thr
 145                 150                 155                 160 gca ttc gaa aac agt ata tac gac cag gaa tac aat atc cgt gta acc     528
Ala Phe Glu Asn Ser Ile Tyr Asp Gln Glu Tyr Asn Ile Arg Val Thr
                 165                 170                 175 atg tat gta caa ttc aga gaa ttt aat ctt aaa gac ccc cca ctt aac     576
Met Tyr Val Gln Phe Arg Glu Phe Asn Leu Lys Asp Pro Pro Leu Asn
             180                 185                 190 cct taa                                                             582
Pro

<210> SEQ ID NO 21
<211> LENGTH: 193
<212> TYPE: PRT
<213> ORGANISM: Porcine circovirus

<400> SEQUENCE: 21

Met Asn Gly Ile Phe Asn Thr Arg Leu Ser Arg Thr Phe Gly Tyr Thr
 1               5                  10                  15

Ile Lys Arg Thr Thr Val Arg Thr Pro Ser Trp Ala Val Asp Met Met
             20                  25                  30

Arg Phe As

```
            115                 120                 125
Ser Thr Ile Asp Tyr Phe Gln Pro Asn Asn Lys Arg Asn Gln Leu Trp
    130                 135                 140

Leu Arg Leu Gln Thr Ala Gly Asn Val Asp His Val Gly Leu Gly Thr
145                 150                 155                 160

Ala Phe Glu Asn Ser Ile Tyr Asp Gln Glu Tyr Asn Ile Arg Val Thr
                165                 170                 175

Met Tyr Val Gln Phe Arg Glu Phe Asn Leu Lys Asp Pro Pro Leu Asn
                180                 185                 190

Pro

<210> SEQ ID NO 22
<211> LENGTH: 1680
<212> TYPE: DNA
<213> ORGANISM: Mycoplasma hyopneumoniae
<220> FEATURE:
<221> NAME/KEY: CDS
<222> LOCATION: (1

-continued

| | | |
|---|---|---|
| gat ttt aaa acc ttc ggt gat ttt tta aaa gca ttt ttc ctt aaa gca<br>Asp Phe Lys Thr Phe Gly Asp Phe Leu Lys Ala Phe Phe Leu Lys Ala<br>210                  215                  220 | | 672 |
| gcc caa ttt aat aat ttt gct cct tgg gca aaa tta gac gat aat ctt<br>Ala Gln Phe Asn Asn Phe Ala Pro Trp Ala Lys Leu Asp Asp Asn Leu<br>225                  230                  235                  240 | | 720 |
| cag tat tca ttt gaa gct atc aaa aaa ggg gaa act aca aaa gaa ggt<br>Gln Tyr Ser Phe Glu Ala Ile Lys Lys Gly Glu Thr Thr Lys Glu Gly<br>                  245                  250                  255 | | 768 |
| aaa aga gaa gaa gta gat aaa aaa gtt aaa gaa tta gat aat aaa ata<br>Lys Arg Glu Glu Val Asp Lys Lys Val Lys Glu Leu Asp Asn Lys Ile<br>            260                  265                  270 | | 816 |
| aaa ggt ata tta cct cag ccc cca gca gct aaa cct gaa gcg gct aaa<br>Lys Gly Ile Leu Pro Gln Pro Pro Ala Ala Lys Pro Glu Ala Ala Lys<br>275                  280                  285 | | 864 |
| cca gta gca gca aaa cct gaa gca gct aaa cct gaa aca aca aaa cca<br>Pro Val Ala Ala Lys Pro Glu Ala Ala Lys Pro Glu Thr Thr Lys Pro<br>290                  295                  300 | | 912 |
| gta gca gct aaa cct gaa gca gca aaa cca gta gca gca aaa cca gta<br>Val Ala Ala Lys Pro Glu Ala Ala Lys Pro Val Ala Ala Lys Pro Val<br>305                  310                  315                  320 | | 960 |
| gca gca aaa cca gtt gct act aat act aat act aat act ggc ttt tca<br>Ala Ala Lys Pro Val Ala Thr Asn Thr Asn Thr Asn Thr Gly Phe Ser<br>                  325                  330                  335 | | 1008 |
| ctt aca aat aaa cca aaa gaa gac tat ttc cca atg gct ttt agt tat<br>Leu Thr Asn Lys Pro Lys Glu Asp Tyr Phe Pro Met Ala Phe Ser Tyr<br>            340                  345                  350 | | 1056 |
| aaa tta gaa tat act gac gaa aat aaa tta agc cta aaa aca ccg gaa<br>Lys Leu Glu Tyr Thr Asp Glu Asn Lys Leu Ser Leu Lys Thr Pro Glu<br>355                  360                  365 | | 1104 |
| att aat gta ttt tta gaa cta gtt cat caa agc gag tat gaa gaa caa<br>Ile Asn Val Phe Leu Glu Leu Val His Gln Ser Glu Tyr Glu Glu Gln<br>370                  375                  380 | | 1152 |
| aaa ata ata aag gaa cta gat aaa act gtt tta aat ctt caa tat caa<br>Lys Ile Ile Lys Glu Leu Asp Lys Thr Val Leu Asn Leu Gln Tyr Gln<br>385                  390                  395                  400 | | 1200 |
| ttc cag gaa gtc aag gta act agt gaa caa tat cag aaa ctt agc cac<br>Phe Gln Glu Val Lys Val Thr Ser Glu Gln Tyr Gln Lys Leu Ser His<br>                  405                  410                  415 | | 1248 |
| cca atg atg acc gag gga tct cct aat caa ggt aaa aaa gcc gaa ggc<br>Pro Met Met Thr Glu Gly Ser Pro Asn Gln Gly Lys Lys Ala Glu Gly<br>            420                  425                  430 | | 1296 |
| gct cct aac caa ggc aaa aaa gcc gaa ggc gca cct agt caa ggg aaa<br>Ala Pro Asn Gln Gly Lys Lys Ala Glu Gly Ala Pro Ser Gln Gly Lys<br>435                  440                  445 | | 1344 |
| aaa gcc gaa ggc gct cct aac caa ggc aaa aaa gcc gaa ggc gca cct<br>Lys Ala Glu Gly Ala Pro Asn Gln Gly Lys Lys Ala Glu Gly Ala Pro<br>450                  455                  460 | | 1392 |
| agt caa ggg aaa aaa gca gag ggt gct tct aat caa caa agc aca act<br>Ser Gln Gly Lys Lys Ala Glu Gly Ala Ser Asn Gln Gln Ser Thr Thr<br>465                  470                  475                  480 | | 1440 |
| acc gaa tta act aat tac ctt cct gaa tta ggt aaa aaa att gac gaa<br>Thr Glu Leu Thr Asn Tyr Leu Pro Glu Leu Gly Lys Lys Ile Asp Glu<br>                  485                  490                  495 | | 1488 |
| atc att aaa aaa caa ggt aaa aat tgg aaa aca gag gtt gaa cta atc<br>Ile Ile Lys Lys Gln Gly Lys Asn Trp Lys Thr Glu Val Glu Leu Ile<br>            500                  505                  510 | | 1536 |
| gag gat aat atc gct gga gat gct aaa ttg cta tac ttt gtc cta agg<br>Glu Asp Asn Ile Ala Gly Asp Ala Lys Leu Leu Tyr Phe Val Leu Arg<br>515                  520                  525 | | 1584 |

```
gat gat tca aaa tcc ggt gat cct aaa aaa tca agt cta aaa gtt aaa    1632
Asp Asp Ser Lys Ser Gly Asp Pro Lys Lys Ser Ser Leu Lys Val Lys
        530             535                 540 ata aca gta aaa caa agt aat aat aat cag gaa tta aaa tct aaa taa    1680
Ile Thr Val Lys Gln Ser Asn Asn Asn Gln Glu Leu Lys Ser Lys
545             550                 555
```

<210> SEQ ID NO 23
<211> LENGTH: 559
<212> TYPE: PRT
<213> ORGANISM: Mycoplasma hyopneumoniae

<400> SEQUENCE: 23

```
Met Glu Phe Gly Ala Phe Lys Ser Val Leu Asn Ser Trp Thr Gly Lys
1               5                   10                  15

Ile Gln His Pro Glu Lys Ala Asp Ile Gln Arg Phe Thr Arg His Leu
            20                  25                  30

Glu Gln Val Lys Leu Gly Ser Asn Ser Val Leu Asn Gln Pro Gln Thr
        35                  40                  45

Thr Lys Glu Gln Val Ile Ser Ser Leu Lys Ser Asn Asn Phe Phe Lys
    50                  55                  60

Asn Gly His Gln Val Ala Ser Tyr Phe Gln Asp Leu Leu Thr Lys Asp
65                  70                  75                  80

Lys Leu Thr Val Leu Glu Thr Leu Tyr Asp Leu Ala Lys Lys Trp Gly
                85                  90                  95

Leu Glu Thr Asn Arg Ala Gln Phe Pro Lys Glu Val Phe Gln Tyr Thr
            100                 105                 110

Lys Asp Ile Phe Ala Glu Ala Asp Lys Leu Lys Phe Leu Glu Gly Lys
        115                 120                 125

Lys Lys Asp Pro Tyr Asn Gln Ile Lys Glu Ile His Gln Leu Ser Phe
    130                 135                 140

Asn Ile Leu Ala Arg Asn Asp Val Ile Lys Ser Asp Gly Phe Tyr Gly
145                 150                 155                 160

Val Leu Leu Leu Pro Gln Ser Val Lys Thr Glu Leu Glu Gly Lys Asn
                165                 170                 175

Glu Ala Gln Ile Phe Glu Ala Leu Lys Lys Tyr Ser Leu Ile Glu Asn
            180                 185                 190

Ser Ala Phe Lys Thr Thr Ile Leu Asp Lys Asn Leu Leu Glu Gly Thr
        195                 200                 205

Asp Phe Lys Thr Phe Gly Asp Phe Leu Lys Ala Phe Phe Leu Lys Ala
    210                 215                 220

Ala Gln Phe Asn Asn Phe Ala Pro Trp Ala Lys Leu Asp Asp Asn Leu
225                 230                 235                 240

Gln Tyr Ser Phe Glu Ala Ile Lys Lys Gly Glu Thr Thr Lys Glu Gly
                245                 250                 255

Lys Arg Glu Glu Val Asp Lys Lys Val Lys Glu Leu Asp Asn Lys Ile
            260                 265                 270

Lys Gly Ile Leu Pro Gln Pro Ala Ala Lys Pro Glu Ala Ala Lys
        275                 280                 285

Pro Val Ala Ala Lys Pro Glu Ala Ala Lys Pro Glu Thr Thr Lys Pro
    290                 295                 300

Val Ala Ala Lys Pro Glu Ala Ala Lys Pro Val Ala Ala Lys Pro Val
305                 310                 315                 320

Ala Ala Lys Pro Val Ala Thr Asn Thr Asn Thr Asn Thr Gly Phe Ser
                325                 330                 335
```

```
Leu Thr Asn Lys Pro Lys Glu Asp Tyr Phe Pro Met Ala Phe Ser Tyr
            340                 345                 350

Lys Leu Glu Tyr Thr Asp Glu Asn Lys Leu Ser Leu Lys Thr Pro Glu
        355                 360                 365

Ile Asn Val Phe Leu Glu Leu Val His Gln Ser Glu Tyr Glu Glu Gln
    370                 375                 380

Lys Ile Ile Lys Glu Leu Asp Lys Thr Val Leu Asn Leu Gln Tyr Gln
385                 390                 395                 400

Phe Gln Glu Val Lys Val Thr Ser Glu Gln Tyr Gln Lys Leu Ser His
                405                 410                 415

Pro Met Met Thr Glu Gly Ser Pro Asn Gln Gly Lys Lys Ala Glu Gly
            420                 425                 430

Ala Pro Asn Gln Gly Lys Lys Ala Glu Gly Ala Pro Ser Gln Gly Lys
        435                 440                 445

Lys Ala Glu Gly Ala Pro Asn Gln Gly Lys Lys Ala Glu Gly Ala Pro
    450                 455                 460

Ser Gln Gly Lys Lys Ala Glu Gly Ala Ser Asn Gln Gln Ser Thr Thr
465                 470                 475                 480

Thr Glu Leu Thr Asn Tyr Leu Pro Glu Leu Gly Lys Lys Ile Asp Glu
                485                 490                 495

Ile Ile Lys Lys Gln Gly Lys Asn Trp Lys Thr Glu Val Glu Leu Ile
            500                 505                 510

Glu Asp Asn Ile Ala Gly Asp Ala Lys Leu Leu Tyr Phe Val Leu Arg
        515                 520                 525

Asp Asp Ser Lys Ser Gly Asp Pro Lys Lys Ser Ser Leu Lys Val Lys
    530                 535                 540

Ile Thr Val Lys Gln Ser Asn Asn Asn Gln Glu Leu Lys Ser Lys
545                 550                 555

<210> SEQ ID NO 24
<211> LENGTH: 5
<212> TYPE: PRT
<213> ORGANISM: Mycoplasma hyopneumoniae
<220> FEATURE:
<221> NAME/KEY: MISC_FEATURE
<222> LOCATION: (1)..(1)
<223> OTHER INFORMATION: Xaa at position 1 is Ala or Thr
<220> FEATURE:
<221> NAME/KEY: MISC_FEATURE
<222> LOCATION: (2)..(2)
<223> OTHER INFORMATION: Xaa at position 2 is Ala or Thr
<220> FEATURE:
<221> NAME/KEY: MISC_FEATURE
<222> LOCATION: (5)..(5)
<223> OTHER INFORMATION: Xaa at position 5 is Glu or Val

<400> SEQUENCE: 24

Xaa Xaa Lys Pro Xaa
1               5

<210> SEQ ID NO 25
<211> LENGTH: 10
<212> TYPE: PRT
<213> ORGANISM: Mycoplasma hyopneumoniae
<220> FEATURE:
<221> NAME/KEY: MISC_FEATURE
<222> LOCATION: (2)..(2)
<223> OTHER INFORMATION: Xaa at position 2 is Glu, Ser or Thr
<220> FEATURE:
<221> NAME/KEY: MISC_FEATURE
```

```
<222> LOCATION: (4)..(4)
<223> OTHER INFORMATION: Xaa at position 4 is Asn or Ser

<400> SEQUENCE: 25

Gly Xaa Pro Xaa Gln Gly Lys Lys Ala Glu
1               5                   10
```

P97 PROTEIN AND USES THEREOF AS VACCINE ADJUVANT

CROSS-REFERENCE TO RELATED APPLICATIONS

The present application claims the benefit of U.S. provisional application Ser. No. 61/639,127, and Canadian application No. 2,776,119, both filed Apr. 27, 2012, which are incorporated herein by reference in their entirety.

FIELD OF THE INVENTION

The present invention relates to vaccines, and more particularly to vaccine adjuvants that potentiate the immune response against antigens.

REFERENCE TO SEQUENCE LISTING

Pursuant to 37 C.F.R. 1.821(c), a sequence listing is submitted herewith as an ASCII compliant text file named "782 16045.2 ST25.txt", that was created on Nov. 13, 2014 and having a size of ~140 kilobytes. The content of the aforementioned file is hereby incorporated by reference in its entirety.

BACKGROUND OF THE INVENTION

Vaccines are considered to be one of the most successful and cost-effective medical interventions against infectious diseases (Hilleman M. R., *Vaccine* 18: 1436-1447, 2000). A vaccine is used to evoke an antigen-specific effectors and memory immune response against a pathogen, with minimal adverse reactions and it should lead to a specific long-term protection against this pathogen.

Traditional live anti-viral and anti-bacterial vaccines typically require no immunological adjuvants. Similarly, live microbial attenuated vaccines are generally much more immunogenic than killed pathogen or subunit protein vaccines and can be effective with no adjuvant or with adjuvants that have limited ability to stimulate immune responses. Recently developed killed pathogens, several vector types or subunit protein vaccines, while offering significant advantages over the traditional vaccines in terms of safety and cost of production, generally have limited immunogenicity compared to natural pathogens. As a result, these vaccines typically require adjuvants with significant immunostimulatory capability to reach their full potential in preventing disease.

A vaccine adjuvant is more precisely a particulate, solid or soluble agent that increases the specific immune responses to an antigen. Vaccine adjuvants can enhance the immune response to vaccine antigens in various ways. When weak antigens are available, they are very useful for augmenting the immunogenicity of these molecules, thereby enhancing their vaccinal potency. They are also used to enhance the speed, vigor, and persistence of the immune response to a strong antigen. They can also modify the nature of the immune response. Depending on which adjuvant is used to stimulate a protective immune response, humoral or cell-mediated immunity can be selected. An adjuvant can modulate antibody specificity, as well as its quantity, isotype and subclass distribution. When used in direct contact with mucous membrane (e.g., intranasal) it can effectively induce mucosal immunity. Adjuvants are also useful for potentiating the immune responses in immunologically immature, immunosuppressed or senescent individuals, acting as an immunological booster. Also, an adjuvant can effectively decrease the dose of antigen and/or the frequency of injection necessary to provide protection.

Adjuvants are immunomodulators that are typically non-covalently linked to antigens and are formulated to enhance the host immune responses. Some of these adjuvants are toxic, however, and can cause undesirable side effects, making them unsuitable for use in humans and many animals. Indeed, only few adjuvants are routinely used in human and veterinary vaccines. Also, currently available adjuvants and vaccines fail to induce a proper immune response capable of protecting against or treating certain infectious diseases, for instance those associated to Human immunodeficiency virus (HIV) or Hepatitis C virus (HCV).

Therefore, there is a need for the development of novel vaccine adjuvants and immunogenic compositions.

The present description refers to a number of documents, the content of which is herein incorporated by reference in their entirety.

SUMMARY OF THE INVENTION

More specifically, in accordance with the present invention, there is provided an immunogenic composition comprising a p97 adhesin adjuvant polypeptide, or a nucleic acid encoding said p97 adhesin adjuvant polypeptide, and a heterologous antigen.

In another aspect, the present invention provides the use of an immunogenic composition comprising a p97 adhesin adjuvant polypeptide, or a nucleic acid encoding said p97 adhesin adjuvant polypeptide, and a heterologous antigen, for inducing an immune response against said heterologous antigen in a subject.

In another aspect, the present invention provides the use of an immunogenic composition comprising a p97 adhesin adjuvant polypeptide, or a nucleic acid encoding said p97 adhesin adjuvant polypeptide, and a heterologous antigen, for the preparation of a medicament for inducing an immune response against said heterologous antigen in a subject.

In another aspect, the present invention provides a method of inducing an immune response against a heterologous antigen in a subject, the method comprising administering to said subject an effective amount of an immunogenic composition comprising a p97 adhesin adjuvant polypeptide, or a nucleic acid encoding said p97 adhesin adjuvant polypeptide, and said heterologous antigen.

In another aspect, the present invention provides the use of a p97 adhesin adjuvant polypeptide, or a nucleic acid encoding said p97 adhesin adjuvant polypeptide, as an adjuvant for a vaccine.

In another aspect, the present invention provides the use of a p97 adhesin adjuvant polypeptide, or a nucleic acid encoding said p97 adhesin adjuvant polypeptide, for the preparation of a vaccine.

In an embodiment, the above-mentioned p97 adhesin adjuvant polypeptide is (i) a polypeptide comprising the amino acid sequence of any one of SEQ ID NOs: 1 to 7; (ii) a polypeptide comprising a sequence that is at least 60% identical to the amino acid sequence of any one of SEQ ID NOs: 1 to 7 and having adjuvant properties; or (iii) a fragment of (i) or (ii) having adjuvant properties.

In a further embodiment, the above-mentioned p97 adhesin adjuvant polypeptide is (i) a polypeptide comprising the amino acid sequence of SEQ ID NO: 1 or 7; (ii) a polypeptide comprising a sequence that is at least 60% identical to the amino acid sequence of SEQ ID NO: 1 or 7 and having adjuvant properties; or (iii) a fragment of (i) or (ii) having adjuvant properties.

In a further embodiment, the above-mentioned p97 adhesin adjuvant polypeptide comprises a sequence corresponding to residues 534 to 1093 of the polypeptide of SEQ ID NO: 7.

In another embodiment, the above-mentioned p97 adhesin adjuvant polypeptide comprises a sequence corresponding to residues 899 to 1108 of the polypeptide of SEQ ID NO: 1.

In an embodiment, the above-mentioned heterologous antigen is an antigen from a human pathogen or an antigen of human origin.

In an embodiment, the above-mentioned heterologous antigen is a polypeptide.

In an embodiment, the above-mentioned p97 adhesin adjuvant polypeptide and the heterologous antigen polypeptide are linked together. In a further embodiment, the above-mentioned p97 adhesin adjuvant polypeptide is N-terminal relative to the heterologous antigen polypeptide.

In an embodiment, the above-mentioned immunogenic composition or vaccine further comprises one or more pharmaceutically acceptable excipients.

Other objects, advantages and features of the present invention will become more apparent upon reading of the following non-restrictive description of specific embodiments thereof, given by way of example only with reference to the accompanying drawings.

Figure 1A:
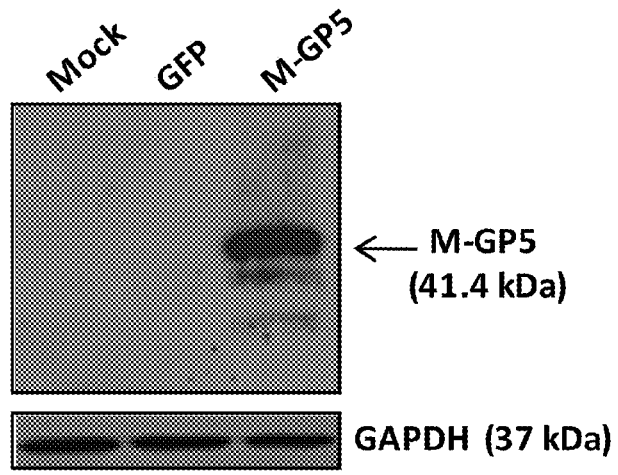
FIGS. 1A to 1E show the expression of recombinant adenoviruses (rAdVs) in vitro. Western Blot analysis of A549 cells lysates mock-infected or infected with rAdVs (MOI:10) expressing GFP, M-GP5 (FIG. 1A), Cap-GP5 (FIG. 1B), P97c-GP5 (FIG. 1C), Cap (FIG. 1D), P97c (FIG. 1E) or P97c and Cap (FIGS. 1D and 1E). Immunoblot was done with a convalescent Porcine reproductive and respiratory syndrome virus (PRRSV)-specific pig antiserum (1:5,000, FIG. 1A), a convalescent Porcine circovirus type 2b (PCV2b)-specific pig antiserum (1:10,000, FIGS. 1B and 1D) or mouse monoclonal Mycoplasma hyopneumoniae anti-P97c antibody (1:5,000, FIGS. 1C and 1E), as primary antibodies, and an anti-pig IgG-HRP (FIGS. 1A, 1B and 1D) or anti-mouse IgG-HRP (FIGS. 1C and 1E) as secondary antibody (1:10,000). Glyceraldehyde-3-phosphate dehydrogenase (GAPDH) immunostaining was used as a loading control.
Figure 1B:
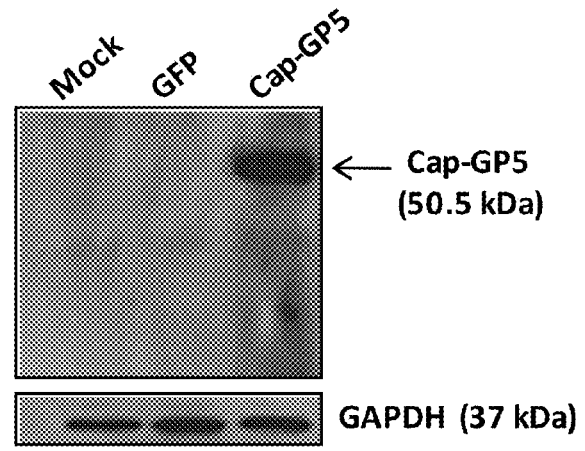
Figure 1C:
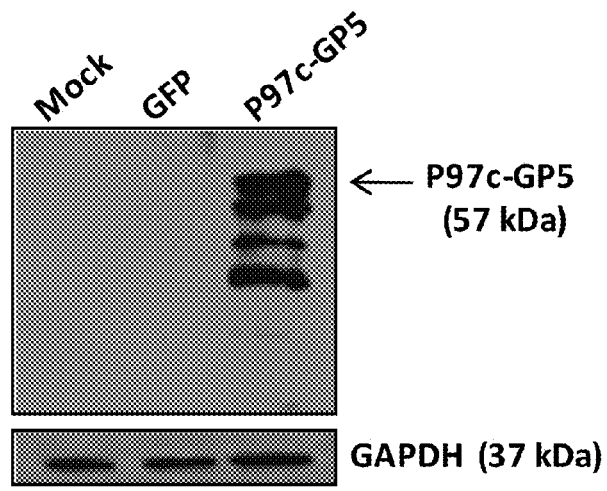
Figure 1D:
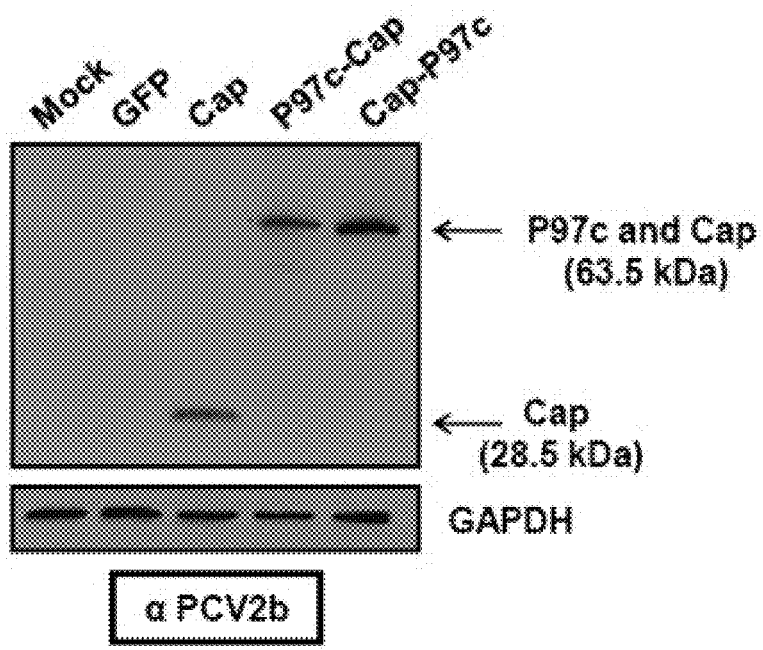
Figure 1E:
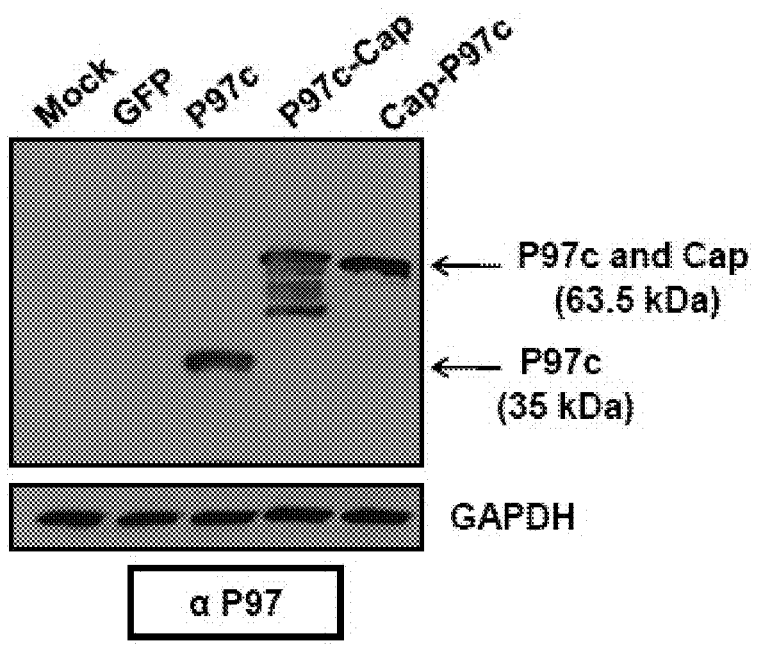

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

The p97 adhesin adjuvant polypeptide, or nucleic acid encoding same, of the present invention can be used to enhance the immunogenicity of a wide variety of antigens including, but not limited to, antigenic lipids, polypeptides, polysaccharides and polynucleotides that encode antigenic polypeptides. The adjuvant of the present invention can further be used in combination with other adjuvant formulations to further enhance the immunogenicity. Accordingly, the p97 adhesin adjuvant polypeptide and/or the p97-encoding nucleic acid is/are incorporated into a composition, e.g., an immunogenic, a vaccine or an immunomodulatory composition, together with an antigen, such as a heterologous antigen. In another aspect, the present invention provides the use of a p97 adhesin adjuvant polypeptide, or a nucleic acid encoding said p97 adhesin adjuvant polypeptide, as an adjuvant for a vaccine (immunogenic composition). In another aspect, the present invention provides the use of a p97 adhesin adjuvant polypeptide, or a nucleic acid encoding said p97 adhesin adjuvant polypeptide, as an adjuvant for the preparation of a vaccine. In an embodiment, the vaccine further comprises an antigen, in a further embodiment a heterologous antigen.

In another aspect, the present invention provides an immunogenic, a vaccine or an immunomodulatory composition comprising a fusion construct, the fusion construct comprising a p97 adhesin adjuvant polypeptide covalently linked to an antigen, or a nucleic acid encoding said fusion construct.

"p97 adhesin adjuvant polypeptide" refers to a polypeptide comprising a region of the *Mycoplasma hyopneumoniae* strain 232 or strain 25934 p97 polypeptide (FIG. 7A or 7G, SEQ ID NO: 1 or 7), or of a paralog thereof such as the p146 adhesin like-protein p97 paralog (FIG. 7B, SEQ ID NO: 2), the p102 paralog (FIG. 7C, SEQ ID NO: 3) the p97 cilium adhesin paralog (FIG. 7D, SEQ ID NO: 4), the P159 paralog (FIG. 7E, SEQ ID NO: 5), or the p216 paralog (FIG. 7F, SEQ ID NO: 6), or a variant thereof having adjuvant/immunostimulatory activity. In an embodiment, the *Mycoplasma hyopneumoniae* is *Mycoplasma hyopneumoniae* strain 232 or 25934. "p97-encoding nucleic acid" refers to a nucleic acid comprising a nucleotide sequence encoding the above-mentioned p97 adhesin adjuvant polypeptide.

The P97 adhesin protein is a proteolytically processed protein encoded by mhp183, the first gene in a two gene operon with the gene encoding the p102 paralog. It is expressed as a 125 kDa protein that undergoes a post-translational cleavage to yield the functional 97 kDa p97 protein, and is involved in the adherence of *M. hyopneumoniae* to the host respiratory cilia. It contains a 17 amino acid N-terminal hydrophobic region. It also contains two functional repeats designated R1 and R2. R1 is a domain comprising several repeats of the amino acid motif A(T)-A(T)-K-P-E(V) (SEQ ID NO: 24) (corresponding to residues 814-888 in FIG. 7A, underlined, or residues 814-858 in FIG. 7G), and is involved in the binding to cilia. The R2 region is a C-terminal domain comprising repeats (typically 3 to 5) of the amino acid motif G-A(E,S,T)-P-N(S)-Q-G-K-K-A-E (SEQ ID NO: 25) (corresponding to residues 991-1020 in FIG. 7A, italicized, or residues 955-1004 in FIG. 7G).

In an embodiment, the p97 adhesin adjuvant polypeptide comprising a region of a *M. hyopneumoniae* p97 polypeptide or the p102 paralog, or a variant thereof having adjuvant, immunostimulatory and/or immunopotentiating activity. In a further embodiment, the p97 adhesin adjuvant polypeptide comprises a region of a *M. hyopneumoniae* p97 polypeptide, or a variant thereof having adjuvant, immunostimulatory and/or immunopotentiating activity. In an embodiment, the p97 adhesin adjuvant polypeptide comprises the R1 region of a p97 adhesin protein or a paralog thereof. In another embodiment, the p97 adhesin adjuvant polypeptide comprises the R2 region of a p97 adhesin protein or a paralog thereof. In another embodiment, the p97 adhesin adjuvant polypeptide comprises the R1 and R2 regions of a p97 adhesin protein or a paralog thereof.

In embodiments, the p97 adhesin adjuvant polypeptide comprises a region or fragment of at least 50, 75, 100, 150, 200, 250, 300, 350, 400, 450, 500, 550, 600, 650, 700, 750, 800, 850, 900, 950 or 1000 amino acids of the *M. hyopneumoniae* p97 polypeptide or paralog thereof, or a variant thereof having adjuvant, immunostimulatory and/or immunopotentiating activity. In an embodiment, the region is located in the C-terminal portion of the *M. hyopneumoniae* p97 polypeptide, e.g. about the last 100, 150, 200, 250, 300, 350, 400, 450, 500, 550, 600, 650, 700, 750, 800, 850 or 900 amino acids. In another embodiment, the p97 adhesin adjuvant polypeptide comprises the full sequence of the *M. hyopneumoniae* p97 polypeptide or paralog thereof, or a variant thereof having adjuvant/immunostimulatory activity. In another embodiment, the p97 adhesin adjuvant polypeptide comprises the full sequence of the *M. hyopneumoniae* p97 polypeptide or paralog thereof, but lacking at least the N-terminal hydrophobic region, or a variant thereof having adjuvant, immunostimulatory and/or immunopotentiating activity. In another embodiment, the p97 adhesin adjuvant polypeptide comprises the amino acid sequence of SEQ ID NO: 23 (FIG. 11B). In another embodiment, the p97 adhesin adjuvant polypeptide comprises residues corresponding to about residues 799 to 1108 of the *Mycoplasma hyopneumoniae* p97 polypeptide of FIG. 7A (SEQ ID NO: 1). Amino acid numbering for p97 adhesin adjuvant polypeptides described herein uses numbering based on the reference *M. hyopneumoniae* p97 polypeptide of FIG. 7A, with residue 1 corresponding to the first methionine in this sequence. It will be understood that amino acid numbering can thus be shifted in situations where the residues corresponding to those referred to herein are within a polypeptide having more or fewer amino acids N-terminal to the region(s) where the residues reside (e.g., a different paralog), relative to the reference *M. hyopneumoniae* strain 232 p97 polypeptide (FIG. 7A), thereby resulting in different amino acid numbering. The corresponding positions in other paralogs may be easily identified, for example by aligning the sequence of a given paralog polypeptide with that depicted in FIG. 7A (e.g., using software/tools for sequence alignment such as Clustal W or EMBOSS Needle).

"Variant" as used herein refers to a p97 adhesin adjuvant polypeptide in which one or more of the amino acids of the native *hyopneumoniae* p97 polypeptide or paralog thereof has/have been modified, but which retains adjuvant, immunostimulatory and/or immunopotentiating activity. The modification may be, for example, a deletion of one or more consecutive or non-consecutive amino acids, a substitution of amino acids, one or more substitution(s) of a naturally occurring amino acid (L-amino acid) by a corresponding D-amino acid, an extension of the sequence by e.g., one, two, three or more amino acids. In an embodiment, the above-mentioned substitution(s) are conserved amino acid substitutions. As used herein, the term "conserved amino acid substitutions" (or sometimes "conservative amino acid substitutions") refers to the substitution of one amino acid for another at a given location in the p97 adhesin adjuvant polypeptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the p97 adhesin adjuvant polypeptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101): Arg (+3.0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In other embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In other embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, H is; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-naphthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cystic acid, epsilon-amino hexanoic acid, delta-amino valeric acid, or 2,3-diaminobutyric acid.

In other embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Biol.* 179: 125-142, 1984). Genetically encoded hydrophobic amino acids include Gly, Ala, Phe, Val, Leu, Ile, Pro, Met and Trp, and genetically, encoded hydrophilic amino acids include Thr, His, Glu, Gln, Asp, Arg, Ser, and Lys.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

The above classifications are not absolute and an amino acid may be classified in more than one category. In addition, amino acids can be classified based on known behavior and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid.

In addition to the substitutions outlined above, synthetic amino acids providing similar side chain functionality can also be introduced into the p97 adhesin adjuvant polypeptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g., —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties, (e.g., (—C=O)—$CH_2$—), (—CHOH)—$CH_2$—), ($CH_2$—$CH_2$—), (—C=S)—NH—), or (—NH—(—C=O) for (—C=O)—NH—)).

Other modifications are also included within the definition of variant of the p97 adhesin adjuvant polypeptide of the present invention. For example, the size of the p97 adhesin adjuvant polypeptide can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, keto-methylene pseudopeptides, β-turn dipeptide cores and β-aminoalcohols for these purposes are known to peptide chemists and are described in for example *Peptidomimetic protocols* (Methods in molecular medicine Vol. 23) W. M. Kazmierski (ed.), Humana Press and Advances in *Amino Acid Mimetics and Peptidomimetics*, Vols. 1 & 2, A. Abell (Ed).

Covalent modifications of the p97 adhesin adjuvant polypeptide are thus included within the scope of the present invention. Such modifications may be introduced into the p97 adhesin adjuvant polypeptide for example by reacting targeted amino acid residues of the polypeptide with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters, e.g. methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazole and tetranitromethane may be used to form O-acetyl tyrosinyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore aspartyl and glutamyl residues may be converted to asparaginyl and glutaminyl residues by reaction with ammonium ions. Glutaminyl and asparaginyl residues may be frequently deaminated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (e.g., $C_6$-$C_{18}$) to the peptides may confer additional biological properties such as protease resistance, plasma protein binding, increased plasma half-life, intracellular penetration, etc. The above description of modification of the p97 adhesin adjuvant polypeptide does not limit the scope of the approaches nor the possible modifications that can be engineered.

In an embodiment, the variant and/or fragment has an identity or similarity of at least 60% with a native *M. hyopneumoniae* p97 polypeptide or a paralog thereof, or with a fragment of the *M. hyopneumoniae* p97 polypeptide or a paralog thereof, and retain adjuvant, immunostimulatory and/or immunopotentiating activity. In further embodiments, the variant and/or fragment has a similarity or identity of at least 65, 70, 75, 80, 85, 90, 91, 92, 93, 94, 95, 96, 97, 98 or 99% with a native *M. hyopneumoniae* p97 polypeptide or a paralog thereof, or with a fragment of the *M. hyopneumoniae* p97 polypeptide or a paralog thereof, and retain adjuvant, immunostimulatory and/or immunopotentiating activity. In other embodiments, the variant and/or fragment has an identity or similarity of at least 60, 65, 70, 75, 80, 85, 90, 91, 92, 93, 94, 95, 96, 97, 98 or 99% with the native *M. hyopneumoniae* strain 232 or 25934 p97 polypeptide of SEQ ID NO:1 or 7, or a fragment thereof.

"Similarity" and "identity" refers to sequence similarity/identity between two polypeptide molecules. The similarity or identity can be determined by comparing each position in the aligned sequences. A degree of similarity or identity between amino acid sequences is a function of the number of matching or identical amino acids at positions shared by the sequences. As the term is used herein, an amino acid sequence is "similar" or "identical" to another sequence if the two sequences are substantially similar or identical (shares at least 60% similarity or identity) and the functional activity of the sequences is conserved. As used herein, a given percentage of similarity or identity between sequences denotes the degree of sequence identity in optimally aligned sequences. An "unrelated" or "non-homologous" sequence shares less than 40% identity, though preferably less than about 25% identity, with a sequence described herein.

Optimal alignment of sequences for comparisons of similarity or identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence similarity or identity may also be determined using the BLAST algorithm, described in Altschul et al., 1990, *J. Mol. Biol.* 215: 403-10 (using the published default settings). Software for performing BLAST analysis may be available through the National Center for Biotechnology Information web site (http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. ScL USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

In an embodiment, the adjuvant is a nucleic acid encoding the above-mentioned p97 adhesin adjuvant polypeptide, fragment thereof and/or variant thereof as defined above. In an embodiment, the nucleic acid comprises a region or fragment of the *M. hyopneumoniae* p97 nucleic acid (FIG. 7A, SEQ ID NO: 10, or FIG. 7G, SEQ ID NO: 16) or a p102 paralog (FIG. 7C, SEQ ID NO: 12), or a variant thereof having adjuvant, immunostimulatory and/or immunopotentiating activity. In a further embodiment, the p97 adhesin adjuvant polypeptide comprising a region of the *M. hyopneumoniae* p97 nucleic acid, or a variant thereof having adjuvant, immunostimulatory and/or immunopotentiating activity.

In embodiments, the p97 adhesin adjuvant nucleic acid comprises a fragment of at least 100, 150, 200, 250, 300, 350, 400, 450, 500, 550, 600, 650, 700, 750, 800, 850, 900, 950, 1000, 1100, 1200, 1300, 1400, 1500, 2000, 2500 or 3000 nucleotides of the *M. hyopneumoniae* p97 nucleic acid or paralog thereof, or a variant thereof having adjuvant/immunostimulatory activity. In an embodiment, the nucleic acid fragment encodes a region located in the C-terminal portion of the *M. hyopneumoniae* p97 polypeptide, e.g. about the last 100, 150, 200, 250, 300, 350, 400, 450, 500, 550, 600, 650, 700, 750, 800, 850 or 900 amino acids. In another embodiment, the p97 adhesin adjuvant nucleic acid comprises the full sequence of the *M. hyopneumoniae* p97 nucleic acid or paralog thereof (FIGS. 8A to 8G), or a variant thereof having adjuvant, immunostimulatory and/or immunopotentiating activity. In another embodiment, the p97 adhesin adjuvant nucleic acid comprises the full sequence of the *M. hyopneumoniae* p97 nucleic acid or paralog thereof, but lacking the nucleotide sequence encoding at least the N-terminal hydrophobic region, or a variant thereof having adjuvant, immunostimulatory and/or immunopotentiating activity. In another embodiment, the p97 adhesin adjuvant nucleic acid comprises a sequence encoding residues corresponding to about residues 534 to 1093 of the *Mycoplasma hyopneumoniae* p97 polypeptide of FIG. 7G, SEQ ID NO: 7). In an embodiment, the nucleic acid comprises a sequence corresponding to about nucleotides 1603 to 3279 of the *Mycoplasma hyopneumoniae* p97 nucleic acid of FIG. 8G, SEQ ID NO: 16). In another embodiment, the p97 adhesin adjuvant nucleic acid comprises a sequence encoding residues corresponding to about residues 799 to 1108 of the *Mycoplasma hyopneumoniae* p97 polypeptide (FIG. 7A, SEQ ID NO: 1). In an embodiment, the nucleic acid comprises a sequence corresponding to about nucleotides 2395 to 3327 of the *Mycoplasma hyopneumoniae* p97 nucleic acid (FIG. 8A).

"Variant" as used herein refers to a p97 adhesin adjuvant nucleic acid in which one or more of the nucleotides of the native *hyopneumoniae* p97 nucleic acid or paralog thereof has/have been modified, but which retains adjuvant, immunostimulatory and/or immunopotentiating activity. The modification may be, for example, a deletion of one or more consecutive or non-consecutive nucleic acids, a substitution of one or more nucleotide(s), or an extension of the sequence by e.g., one, two, three or more nucleotide(s).

In an embodiment, the variant and/or fragment has an identity or similarity of at least 60% with a native *M. hyopneumoniae* p97 nucleic acid or a paralog thereof, or with a fragment of the *M. hyopneumoniae* p97 nucleic acid or a paralog thereof, and retain adjuvant/immunostimulatory activity. In further embodiments, the variant and/or fragment has a similarity or identity of at least 65, 70, 75, 80, 85, 90, 91, 92, 93, 94, 95, 96, 97, 98 or 99% with a native *M. hyopneumoniae* p97 nucleic acid or a paralog thereof, or with a fragment of the *M. hyopneumoniae* p97 nucleic acid or a paralog thereof, and retain adjuvant, immunostimulatory and/or immunopotentiating activity. In other embodiments, the variant and/or fragment has an identity or similarity of at least 60, 65, 70, 75, 80, 85, 90, 91, 92, 93, 94, 95, 96, 97, 98 or 99% with the native *M. hyopneumoniae* p97 strain 232 or 25934 nucleic acid of SEQ ID NO:10 (FIG. 7A) or SEQ ID NO: 16 (FIG. 7G), or a fragment thereof. In an embodiment, the p97 adhesin adjuvant nucleic acid comprises the nucleotides sequences of FIG. 11A (SEQ ID NO:22). In another embodiment, the p97 adhesin adjuvant nucleic acid comprises the nucleotides sequences of FIG. 9A (SEQ ID NO:8).

By "antigen" is meant a molecule that is capable of stimulating a host's immune system to make a cellular antigen-specific immune response and/or a humoral antibody response when the antigen is presented/administered. It refers to any natural or synthetic compound or chemical entity (lipids, phospholipids, glycolipids, saccharides, nucleic acids, etc.) capable of stimulating a immune response in a host. In an embodiment, the antigen is a polypeptide (e.g., a protein or peptide derived from a pathogen or a tumor cell). A polypeptide antigen may contain one or more epitope(s). Normally, an epitope will include between about 3-15, generally about 5-15, amino acids. Epitopes of a given protein can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance (NMR). See, e.g., Epitope Mapping Protocols, supra. "Antigen" also refers to any natural or synthetic compound or chemical entity (lipids, phospholipids, glycolipids, saccharides, nucleic acids, etc.) capable of stimulating an immune response in a host.

The term "antigen" as used herein denotes both subunit antigens, i.e., antigens which are separate and discrete from a whole organism with which the antigen is associated in nature, as well as killed, attenuated or inactivated bacteria, viruses, parasites or other microbes, or tumor cell lysates. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an immunogenic protein, or antigenic determinant in vivo, such as in nucleic acid immunization applications, is also included in the definition of antigen herein. The antigenic polynucleotide can be delivered through two major routes, either using a viral or bacterial host as gene delivery vehicle (live vaccine vector) or administering the gene in a free form, e.g., inserted into a plasmid (DNA vaccine). Viral and bacterial vaccine vectors are well known in the art (see New Generation Vaccines, 3$^{rd}$ edition, 2004 and Vaccine Protocols, 2$^{nd}$ edition, Humana Press, 2003) and include, for example, Poxvirus, adenovirus, Measles virus, alphavirus, Yellow Fever virus, Semliki Forest virus, poliovirus, herpex simplex virus, vesicular stomatitis virus, *Listeria monocytogenes*, *Salmonella* and *Shigella*. The vaccine vector contains a polynucleotide antigen that is placed under the control of elements required for expression.

"Heterologous antigen" as used herein refers to an antigen that is derived from a species that is different from the p97 adhesin adjuvant polypeptide, i.e. that is not derived from *Mycoplasma hyopneumoniae*. In an embodiment, the antigen is not derived from a pathogen affecting pigs, or is not of pig origin. In an embodiment, the antigen is not derived from a pathogen affecting farm animals (pig, cow, horse, poultry, etc.), or is not of farm animal origin. In another embodiment, the antigen is not derived from a pathogen affecting non-human animals. In an embodiment, the antigen is derived from a human pathogen (e.g., a bacteria or a virus affecting humans), or is from human origin (such as a human polypeptide or a fragment thereof). In another embodiment, the antigen is not derived from PRRSV, PCV2, pseudorabies virus, swine influenza virus, *Salmonella cholerasuis, Salmonella typhimurium, Erysipelothrix rhusiopathiae, Lawsonia intracellulars, Haemophilus parasuis, Bordetella bronchiseptica, Streptococcus suis, Actinobacillus pleuropneumoniae, Escherichia coli, Pasteurella multocida, Clostridium perfringens* type A and type C, bovine herpesvirus type 1 (BHV-1), bovine viral diarrhea virus (BVDV), bovine respiratory syncitial virus (BRSV), parainfluenza virus, *Pasteurella multocida, Haemophilus somnus, Mycoplasma mycoides, Mycoplasma bovis, Mycoplasma agalactiae, Mycoplasma californicum, Mycoplasma bovirhinis, Mycoplasma dispar, Mycoplasma canis*, or *Manheimia haemolytica*.

Further, for purposes of the present invention, antigens (e.g., polypeptides or other biomolecules) can be derived from any of several known pathogens, such as viruses, bacteria, parasites and fungi, as well as any of the various tumor antigens. The antigen may also be an antigen involved in diseases or conditions for which vaccination may be useful, e.g., certain allergies and/or immune/inflammation disorders.

The immunogenic or vaccine compositions of the present invention contains an antigen capable of eliciting an immune response against a pathogen, such as an animal or human pathogen, which antigen may be derived from Human Immunodeficiency virus (HIV), such as Tat, Nef, Gag, Pol, gp120 or gp160, human herpes viruses, such as gD or derivatives thereof or Immediate Early protein such as ICP27 from HSV1 or HSV2, cytomegalovirus (such as gB or derivatives thereof), Rotavirus, Epstein Barr virus (such as gp350 or derivatives thereof), Varicella Zoster Virus (such as gpl, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, *Vaccine*, 1992, 10: 915-920) or purified or recombinant proteins thereof, such as HA, NP, NA, or M proteins, or combinations thereof).

Antigens can also be derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C, Th Ra12, Tb H9, Tb Ra35, Tb38-1, Erd 14, DPV, MTI, MSL, mTTC2 and hTCC1), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp., including *H. pylori* (for example urease, catalase, vacuolating toxin); *Pseudomonas* spp., including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC. DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leishmania* spp., including *L. major; Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans, Streptococcus* spp., including *S. pneumoniae* (for example capsular polysaccharides and conjugates thereof, PsaA, PspA, streptolysin, choline-binding proteins) and the protein antigen Pneumolysin (*Biochem Biophys Acta,* 1989, 67, 1007; Rubins et al., *Microbial Pathogenesis,* 25: 337-342), and mutant detoxified derivatives thereof (WO 90/06951; WO 99/03884), antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

The vaccine composition of the present invention may also comprise a tumor antigen and be useful for the prevention or immunotherapeutic treatment of cancers. For example, the adjuvant formulation finds utility with tumor rejection antigens such as those for prostate, breast, colorectal, lung, pancreatic, renal or melanoma cancers. Exemplary antigens include MAGE 1, 3 and MAGE 4 or other MAGE antigens, PRAME, BAGE, Lage (also known as NY-Eos-1) SAGE and HAGE or GAGE. Indeed these antigens are expressed in a wide range of tumor types such as melanoma, lung carcinoma, sarcoma and bladder carcinoma.

Other tumor-specific antigens are suitable for use in the vaccine composition of the present invention and include, but are not restricted to tumor-specific gangliosides such as GM2, and GM3 or conjugates thereof to carrier proteins; or said antigen may be a self-peptide hormone such as whole length Gonadotrophin hormone releasing hormone, a short 10 amino acid long peptide, useful in the treatment of many cancers, or in immunocastration.

Prostate antigens can also be utilized, such as Prostate specific antigen (PSA), PAP, STEAP, PSCA, PCA3, PSMA or Prostase.

Other tumor-associated antigens (TAA) useful in the context of the present invention include: Carcinoembryonic antigen (CEA), KSA (also known as EpCAM), gp100, Plu-1, HASH-1, HasH-2, Cripto, Criptin. Additionally, antigens particularly relevant for vaccines in the therapy of cancer also comprise tyrosinase and survivin).

Other antigens include Mucin-derived peptides such as Muc1, for example Muc1-derived peptides that comprise at least one repeat unit of the Muc1 peptide, preferably at least two such repeats and which is recognized by the SM3 antibody. Other mucin-derived peptides include peptides from Muc5.

The present invention is also useful in combination with breast cancer antigens such as her2/Neu, mammaglobin. Preferably the Her2/neu comprises the entire extracellular domain (comprising approximately amino acids 1-645) or fragments thereof and at least an immunogenic portion of or the entire intracellular domain approximately the C-terminal 580 amino acids. In particular, the intracellular portion should comprise the phosphorylation domain or fragments thereof.

The compositions may comprise antigens associated with tumor-support mechanisms (e.g. angiogenesis, tumor invasion), for example Angiopoietin (Ang)-1 and -2, tyrosine kinase with immunoglobulin and epidermal growth factor homology domains (Tie)-2 as well as vascular endothelial growth factor (VEGF).

The vaccine or immunogenic composition of the present invention may be used for the prophylaxis or therapy of allergy. Such composition would comprise allergen specific (for example Der p1 and Der p5) and allergen non-specific antigens (for example peptides derived from human IgE, including but not restricted to the Stanworth decapeptide. Other antigens include for example antigens derived from *Aspergillus fumigatus*.

The vaccine or immunogenic composition of the present invention may also be used for the prophylaxis or therapy of chronic disorders others than allergy, cancer or infectious diseases. Such chronic disorders are diseases such as inflammatory and autoimmune diseases, atherosclerosis, and Alzheimer. Antigens relevant for the prophylaxis and the therapy of patients susceptible to or suffering from Alzheimer neurodegenerative disease are, in particular, the N-terminal 39-43 amino acid fragment (Abeta) of the amyloid precursor protein (APP) and smaller fragments.

In embodiments, the p97 adhesin adjuvant polypeptide or nucleic acid may be covalently linked to the antigen either directly (e.g., through a peptide bond) or via a suitable linker moiety, e.g., a linker of one or more amino acids (e.g., a polyglycine linker) or another type of chemical linker (e.g., a carbohydrate linker, a lipid linker, a fatty acid linker, a polyether linker, PEG, etc. (see, e.g., Hermanson (1996) Bioconjugate techniques). Accordingly, in another aspect, the present invention provides a vaccine or immunogenic composition comprising a fusion polypeptide, the fusion polypeptide comprising a p97 adhesin adjuvant polypeptide linked to an antigen, in a further embodiment a heterologous antigen.

In an embodiment, one or more additional peptides or polypeptides may be inserted (1) between the p97 adhesin adjuvant polypeptide and the antigen (2) N-terminal to the p97 adhesin adjuvant polypeptide/antigen construct, and/or (3) C-terminal to the p97 adhesin adjuvant polypeptide/antigen construct. In an embodiment, the p97 adhesin adjuvant polypeptide and the antigen are covalently linked through a peptide bond (as a fusion protein). In an embodiment, the p97 adhesin adjuvant polypeptide is N-terminal relative to the antigen. In an embodiment, the p97 adhesin adjuvant nucleic acid is 5' relative to the nucleic acid encoding the antigen.

In an embodiment, the N and/or C-terminal end of the p97 adhesin adjuvant polypeptide/antigen construct is modified. The N- and/or C-terminal amino acids may be modified by amidation, acetylation, acylation or other modifications known in the art. In an embodiment, the amino terminal residue (i.e., the free amino group at the N-terminal end of the polypeptide) of the p97 adhesin adjuvant polypeptide/antigen construct is modified (e.g., for protection against degradation). In an embodiment, the modification is acylation with a $C_2$-$C_{16}$ acyl group, in a further embodiment, the modification is an acetylation.

In an embodiment, the carboxy terminal residue (i.e., the free carboxy group at the C-terminal end of the polypeptide) of the p97 adhesin adjuvant polypeptide/antigen construct is modified (e.g., for protection against degradation). In an embodiment, the modification is an amidation.

In an embodiment, the "immunogenic composition" or "vaccine" comprises a plurality (2, 3, 4, 5 or more) of repeats of the p97 adhesin adjuvant polypeptide or nucleic acid.

"Immunogenic composition" or "vaccine" as used herein refers to a composition or formulation comprising one or more polypeptides or a vaccine vector. Vaccination methods for treating or preventing infection in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch).

"Adjuvant" refers to a substance which, when added to an immunogenic agent such as an antigen, nonspecifically enhances or potentiates an immune response to the agent in the host upon exposure to the mixture. "Adjuvant", "immunostimulatory" and "immunopotentiating" activity as used refers to an increase in the immune response/reaction to an antigen due to the p97 adhesin adjuvant polypeptide, i.e. relative to the immune response/reaction when the antigen is used alone.

In another aspect, the present invention also provides a nucleic acid encoding the above-mentioned p97 adhesin adjuvant polypeptide/heterologous antigen construct. The invention also provides a vector comprising the above-mentioned nucleic acid. In yet another aspect, the present invention provides a cell (e.g., a host cell) comprising the above-mentioned nucleic acid and/or vector. The invention further provides a recombinant expression system, vectors and host cells, for the expression/production of encoding the above-mentioned p97 adhesin adjuvant polypeptide/heterologous antigen construct, using for example culture media, production, isolation and purification methods well known in the art.

Such vectors comprise a nucleic acid sequence capable of encoding such a p97 adhesin adjuvant polypeptide/heterologous antigen construct operably linked to one or more transcriptional regulatory sequence(s). In an embodiment, the p97 adhesin adjuvant polypeptide/heterologous antigen construct further comprises a domain which facilitates its purification (e.g., His-tag, GST-tag). Nucleic acids may be introduced into cells for expression using standard recombinant techniques for stable or transient expression.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors".

A recombinant expression vector of the present invention can be constructed by standard techniques known to one of ordinary skill in the art and found, for example, in Sambrook et al. (1989) in Molecular Cloning: A Laboratory Manual. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing DNA into mammalian cells in vivo are also known, and may be used to deliver the vector DNA of the invention to a subject for gene therapy.

"Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

The p97 adhesin adjuvant polypeptide/heterologous antigen construct of the invention can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify the p97 adhesin adjuvant polypeptide/heterologous antigen construct will depend, in part, on synthesis strategy and on factors such as net charge, hydrophobicity, hydrophilicity, and the like, and will be apparent to those of ordinary skill in the art. For affinity chromatography purification, any antibody which specifically binds the p97 adhesin adjuvant polypeptide/heterologous antigen construct, or an affinity tag attached thereto, may for example be used.

In an embodiment, the above-mentioned p97 adhesin adjuvant polypeptide/heterologous antigen construct is substantially pure. A product is "substantially pure" when it is separated from the components that naturally accompany it. Typically, a compound is substantially pure when it is at least 60%, more generally 75%, preferably over 90% and more preferably over 95, 96, 97, 98 or 99% by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by expression of a recombinant nucleic acid molecule encoding a polypeptide compound; or by chemical synthesis. Purity can be measured using any appropriate method such as column chromatography, gel electrophoresis, HPLC, etc.

The vaccine or immunogenic composition of the present invention may also further comprise one or more pharmaceutically acceptable carrier or excipient. As used herein "pharmaceutically acceptable carrier" or "excipient" includes any and all solvents, dispersion media, coatings, antibacterial and antifungal agents, isotonic and absorption delaying agents, and the like that are physiologically compatible. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (Rowe et al., Handbook of pharmaceutical excipients, 2003, 4$^{th}$ edition, Pharmaceutical Press, London UK). Except insofar as any conventional media or agent is incompatible with the active compound, use thereof in the pharmaceutical compositions of the invention is contemplated. Supplementary active compounds or multiple heterologous antigens can also be incorporated into the compositions.

The vaccine or immunogenic composition of the present invention may also further comprise one or more additional adjuvants (in addition to the p97 adhesin adjuvant polypeptide), for example adjuvants currently used in the field of vaccines such as (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), AS04 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles.

The composition of the present invention may be used for both prophylactic and therapeutic purposes. Accordingly, there is provided the use of a p97 adhesin adjuvant polypeptide, in combination with a heterologous antigen, in the manufacture of an immunogenic composition (e.g., a vaccine) for the prophylaxis and/or the treatment of viral, bacterial, fungal, parasitic infections, allergy, cancer and other disorders in which the heterologous antigen may be useful. Accordingly, the present invention provides for a method of treating a mammal susceptible to or suffering from an infectious disease or cancer, or allergy, or autoimmune disease using the above-mentioned composition or vaccine (e.g., by administering an effective amount of the composition to a subject in need thereof). In a further aspect of the present invention, there is provided a vaccine or immunogenic combination, comprising a p97 adhesin adjuvant polypeptide and a heterologous antigen, as herein described, for use as a medicament. Immunogenic/vaccine preparation is generally described in *New Trends and Developments in Vaccines*, edited by Voller et al., University Park Press, Baltimore, Md., U.S.A. 1978.

As used herein, "treatment" is an approach for obtaining beneficial or desired results, including clinical results. For purposes of this invention, beneficial or desired clinical results include, but are not limited to, (i) prevention, that is, causing the clinical symptoms not to develop, e.g., preventing disease/infection from occurring and/or developing to a harmful state; (ii) alleviation or amelioration of one or more symptoms, (iii) diminishment of extent of disease, (iv) stabilizing (i.e., not worsening) state of disease, (v) preventing spread of disease, (vi) delay or slowing of disease progression, (vii) amelioration or palliation of the disease state, and (viii) remission (whether partial or total), whether detectable or undetectable. "Treatment" can also mean prolonging survival as compared to expected survival if not receiving treatment.

Treatment may be effected in a single dose or repeated at intervals. The appropriate dosage depends on various parameters understood by skilled artisans such as the vaccine or vaccine vector itself, the route of administration or the condition of the mammal to be vaccinated (weight, age, gender, and the like).

An "effective amount" of a substance is that amount sufficient to effect beneficial or desired results, including clinical results, and, as such, an "effective amount" depends upon the context in which it is being applied. In the context of administering a vaccine composition of the present invention, an effective amount is, for example, an amount sufficient to achieve a modulation (quantitative and/or qualitative) of the immune response as compared to the immune response obtained when the antigen is administered alone (without a p97 adhesin adjuvant polypeptide). An effective amount can be administered in one or more administration(s).

The present invention is illustrated in further details by the following non-limiting examples.

EXAMPLE 1

Material and Methods

Viruses, Cells and Synthetic Genes:

The Porcine Reproductive and Respiratory Syndrome Virus (PRRSV) IAF-Klop strain (Genbank accession No U64928) was propagated and titrated in MARC-145 cells in Dulbecco's modified Eagle's medium (DMEM; Invitrogen, Carlsbad, Calif.) supplemented with 8% of fetal bovine serum (FBS; PAA Laboratories, Inc., Etobicoke, Ontario) at 37° C. in a humidified atmosphere of 5% $CO_2$ (Kheyar, A., et al., *Vaccine*, 2005. 23(31): 4016-22).

Porcine circovirus type 2b (PCV2b) FMV-06-1717 strain (Gagnon, C. A., et al., *J Vet Diagn Invest*, 2008. 20(5): p. 545-58) was propagated and titrated in PK15A cells, a sub-clone of PCV non-infected PK15 cells in Earle's minimal essential medium (EMEM; Wisent, St-Bruno, Québec, Canada), supplemented with 10% FBS, penicillin (100 U/ml)/streptomycin (100 μg/ml) (Invitrogen), 0.1 mM non-essential amino acids (Wisent), 1 mM sodium pyruvate (Wisent), 2.5 mg/ml of amphotericin B (Invitrogen), and 10 mM HEPES buffer (Wisent) at 37° C. in a humidified atmosphere (Gagnon, C. A., et al., *Can Vet J*, 2007. 48(8): 811-9).

Recombinant adenoviruses (rAdVs) were propagated and titrated in the AD-293 cells line (Agilent Technologies, Santa Clara, Calif.) in DMEM supplemented with 8% of FBS at 37° C. in a humidified atmosphere of 5% $CO_2$. A549 cells were propagated in DMEM supplemented with 8% of FBS and maintained at 37° C. in a humidified atmosphere of 5% $CO_2$. These cells were E1-deficient and were used to confirm protein expression from the rAdVs (Imler, J. L., et al., *Gene Ther*, 1996. 3(1): 75-84).

The codons most frequently used by *Sus Scrofa* cells were used to generate synthetic open reading frame: ORF5 and ORF6 of PRRSV on the basis of PRRSV IAF-Klop sequence (Genbank accession No. U64928); ORF2 of PCV2b gene on the basis of PCV2b FMV-06-1717 sequence (Gagnon, C. A., et al., *J Vet Diagn Invest*, 2008. 20(5): 545-58), P97c gene (933 C-terminal nucleotides) on the basis of *M. hyopneumoniae* VR232 sequence (Genbank accession No. U50901.1). The constructs were synthesized by the GeneArt™ Gene Synthesis Services (Invitrogen).

Fusion of Genes of Interest:

Different genes of interest were amplified by PCR and were cloned into pBluescript™ KS(+) (Stratagene, La Jolla, Calif.). When necessary, genes of interest were linked with the nucleotide sequence GTTACCACC (GTT, Jiang W, et al. *Vet Immunol Immunopathol* 2006; 113(1-2): 169-80). The open reading frames (ORF) encoding P97c, Cap, M-GP5, Cap-GP5, P97c-GP5, P97c-Cap or Cap-P97c were validated by DNA sequencing through the McGill University Sequencing Services (Montreal, Québec, Canada).

Construction of Recombinant Adenoviruses:

The rAdVs used in the studies described herein were a replication-defective E1- and E3-deleted human serotype 5. The different amplicon previously cloned into pBluescript™ KS(+) were digested with Bg/II/XhoI (New England Biolabs, Ipswich, Mass.) and subsequently cloned into the corresponding restriction sites into the transfer vector pShuttle-IRES-hrGFP-1 (Agilent Technologies). All constructs were confirmed by DNA sequencing through the McGill University Sequencing Services. The recombinant plasmids were linearized with PmeI (New England Biolabs) and rescued into the genome of the pAdEasy-1 vector (Agilent Technologies) by homologous recombination in *E. Coli* BJ5183 bacteria cells (MP biomedicals, Irvine, Calif.) by electroporation (2.5 kV, 200 Ohms and 25 μF). The integrity of the recombinant rAdVs genome was confirmed by PCR and restriction enzyme digestion. To produce rAdVs, plasmids were linearized by PacI digestion and AD-293 cells were transfected with 2 μg per well of plasmids of a 6-well plate using Poly-Fect™ transfection reagent (Qiagen, Valencia, Calif.). The transfected cells were 24 h later overlayed with agarose (Invitrogen) (0.45% in DMEM supplemented with 5% FBS) and monitored daily until the appearance of viral plaques. After three rounds of viral plaque purification, rAdVs were propagated at high titers and purified by double cesium chloride gradient, as previously described (Bourbeau D, et al., *Cancer Res* 2007; 67(7): 3387-95). The titers of rAdVs were determined in AD-293-infected cells and titers were expressed in tissue culture infectious dose 50 per ml ($TCID_{50}$/ml).

Western Blot Assay:

A549 cells were seeded in 6-well tissue culture plates and infected with rAdVs (MOI: 10). 24 h post-infection, cells from six wells were lysed and total cell protein concentrations were quantified with the DC protein assay kit (Bio-Rad, Mississauga, ON, CA). For each sample, 50 μg of total cell extract prepared as described (Gomez Corredor A and Archambault D. *J Virol* 2009; 83(24): 12842-53) was electrophoretically separated onto 12% SDS-PAGE and transferred to nitrocellulose membranes. The membranes were blocked in phosphate buffered saline (PBS) containing 0.05% Tween™-20 (PBS-T) in presence of 5% non-fat dry milk for 1 h at room temperature and then incubated overnight at 4° C. with convalescent PRRSV-specific pig antiserum (1/5000), PCV2b-specific pig antiserum (1/10000), mouse monoclonal anti-P97c antibody (MAb 8H4-G6) (1/1,000) (Okamba, F. R., et al., *Clin Vaccine Immunol*, 2007. 14(6): p. 767-74) or GAPDH 1/10,000 (Sigma-Aldrich, St. Louis, Mo.). Glyceraldehyde-3-phosphate dehydrogenase (GAPDH) immunostaining (Sigma-Aldrich, St-Louis, Mo.) was used as a loading control. Detection of the proteins was performed as described in Gomez Corredor A and Archambault D., *J Virol* 2012; 86(9):4892-905.

Recombinant Protein Production:

Plasmid pGEX-4T1 (Pharmacia Biotech, Piscataway, N.J.) encoding GP5 of PRRSV IAF-Klop isolate or P97c (amino acids 534 to 1093) of *M. hyopneumoniae* 25934 isolate (GenBank accession # AY512905) were kindly provided by Dr. Carl Gagnon and has been described in Okamba, F. R., et al., 2007, supra. Cap protein (lacking the 39 N-terminal amino acids; Zhou, J. Y., et al., *J Biotechnol*, 2005. 118(2): p. 201-11) of PCV2b FMV-06-1717 isolate was cloned into pGEX-4T1. The recombinant GP5 protein (rGP5), P97c protein (rP97c) or Cap protein (rCap) were produced in BL21(DE3) pLysS competent *E. coli* cells (Promega, Madison, Wis.) upon induction at $OD_{(600\ nm)}$ of 1.2 with 0.1 mM IPTG (isopropyl β-D-1-thiogalactopyranoside) for 4 h at 37° C. Cells were lysed and separated onto a 12% SDS-PAGE. The band corresponding to recombinant proteins was excised from the gel and electroeluted. The purified proteins were dialyzed against PBS and stored at −80° C. for further use. The protein concentration was quantified with the DC protein assay kit as described above. The nature of the eluted proteins was confirmed by Western blot as described above. These proteins were used in the ELISA.

Mice Immunization:

Animal protocols were approved by the University's Animal Protection Institutional Committee according to the regulations of the Canadian Council for Animal Care. 6 weeks old female BALB/c mice were obtained from Charles River Laboratory (St-Constant, Quebec, Canada).

In a first experiment (Experiment 1), mice were randomly divided into 4 groups of 5 mice and immunized intramuscularly (IM) at days 0 and 14 with $10^9$ TCID$_{50}$ of rAdVs expressing M-GP5, Cap-GP5, P97c-GP5 or GFP as negative control. Blood samples were collected from the mandibular vein at 0, 14, 28 and 35 days post-immunization (dpi). At each time point, serum samples were pooled for each group of mice. On 49 dpi, blood was obtained from cardiac blood puncture in mice under anaesthesia with isoflurane (Fisher Scientific, Ville St-Laurent, Qc, Canada). Following clotting, samples were centrifuged (600×g at room temperature for 10 min) and the resulting sera were stored at −20° C. until analysis.

In a second experiment (Experiment 2), mice were randomly divided into 5 groups of 6 mice and immunized IM at days 0 and 14 with $10^9$ TCID$_{50}$ of rAdVs expressing P97c, Cap, P97c-Cap, Cap-P97c or GFP as negative control. Blood samples were collected from the mandibular vein at 0, 14, 28, 35 and 49 dpi. At each time point, serum samples were pooled for each group of mice. On 56 dpi, blood was obtained from cardiac blood puncture and sera were prepared as described above.

Antibody Response:

Indirect ELISA.

The presence of serum GP5, Cap or P97c-specific antibodies was evaluated by an indirect ELISA using Immulon™ 2HB 96-well microtiter plates (Thermo Labsystems, Franklin, Mass.). Plates were coated with 0.1 µg of recombinant proteins (rGP5, rCap or rP97c) or with 1 µg of PRRSV GP5 peptide (SSSQLQSIYNLTIC, SEQ ID NO: 15) per well diluted in 0.05 M sodium carbonate buffer (pH 9.6) to a final volume of 100 µl. Following an overnight incubation at 4° C., plates were washed 4 times with PBS-T and then saturated with 150 µl of PBS-T with 1% BSA overnight at 4° C. One hundred microliters of mice serum, diluted to 1/100 (or 1/50 for IgG isotype detection) in PBS-T with 1% BSA, were added into wells and incubated for 2 h at 37° C. Plates were then washed as previously described and HRP-conjugated goat anti-mouse total IgGs (1:10,000), IgG1 (1:5,000), IgG2a (1:2,500), IgG2b (1:2,500) or IgG3 (1:500) (Santa Cruz Biotechnologies, Santa Cruz, Calif.) in PBS-T with 1% BSA, were added for 1 h at 37° C. Plates were washed and HRP signal was detected by adding 100 µl of tetramethylbenzidine (TMB, Sigma-Aldrich) per well. Reaction was stopped after 20 minutes by adding 50 µl 1M $H_2SO_4$ to each well at room temperature, and optical density (OD) was determined at a wave length of 450 nm (using Tecan™ Infinite M1000 reader, Tecan Group Ltd, Mannedorf, Switzerland). For each serum sample, O.D. was corrected by subtracting O.D. value of uncoated wells from O.D. value obtained with antigen-coated wells.

Virus-Specific Neutralization Assay (NT).

Two-fold serial dilutions of each serum sample (inactivated for 30 min at 56° C.) were done in cell culture medium. The PRRSV-specific NT was performed by a viral cytopathic effect inhibition method using four wells of indicator cells per serum dilution and an incubation time of 96 h (Dea, S., et al., *J Clin Microbiol*, 1996. 34(6): 1488-93). The neutralizing Ab (NAb) titer was expressed as the reciprocal of the highest sample dilution neutralizing 100 TCID$_{50}$ of the virus. For the PCV2b-specific NT, 25 µl of serum two-fold serial dilutions was incubated with 25 µl of 100 TCID$_{50}$ of the virus for 1 h at 37° C. The mixture was then transferred to PK15A cells plated in a 96-well plate (four wells per specimen dilution, 8×10$^4$ cells/well). The inoculum was removed 1 h later and 50 µl of fresh cell culture medium was added into each well. Cells were fixed in PBS-formaldehyde 4% after 96 h, permeabilized with 1:1 acetone/methanol solution for 15 min at −20° C., and blocked with 5% BSA in PBS for 1 h at 37° C. Cells were incubated with rabbit FITC-labeled anti-porcine secondary Ab (1/250) (MP Biomedicals) for 45 min at 37° C. Nuclei were counterstained with propidium iodide (Sigma-Aldrich). Images were taken using an inverse microscope (Nikon® TE-300) coupled to the confocal Bio-Rad® MRC-1024ES system, and analyzed with Image-J® software. For each well, the number of PCV2b-infected cells was compared to that of PK15A cells inoculated with PCV2b exposed to serum from non-immunized mice (control). NAb titers were expressed as the reciprocal of the highest dilution of the serum that inhibited more than 50% of PCV2b infection.

Statistical Analysis:

Where indicated, one-way analysis of variance (ANOVA) followed by Tukey's post-test were carried out for statistical analyses between multiple groups using GraphPad™ Prism 5 software (Windows Version 5.0, Lajolla, Calif., USA).

EXAMPLE 2

Experiment 1

Expression of Recombinant Adenoviruses

Expression of proteins was detected by western-blot 24 h after infection of A549 cells with rAdVs expressing GFP, M-GP5, Cap-GP5 or P97c-GP5. As shown in FIGS. 1A-1E, M-GP5 (FIG. 1A), Cap-GP5 (FIG. 1B), P97c-GP5 (FIG. 1C), Cap (FIG. 1D), P97c (FIG. 1E), P97c-Cap and Cap-P97c (FIGS. 1D and 1E) proteins were expressed at the expected molecular weights. No immunoreactive bands were detected with extracts from uninfected control cells or from cells infected with AdVs expressing GFP.

Antibody (Ab) Response in Mice Following Immunization

Figure 2A:
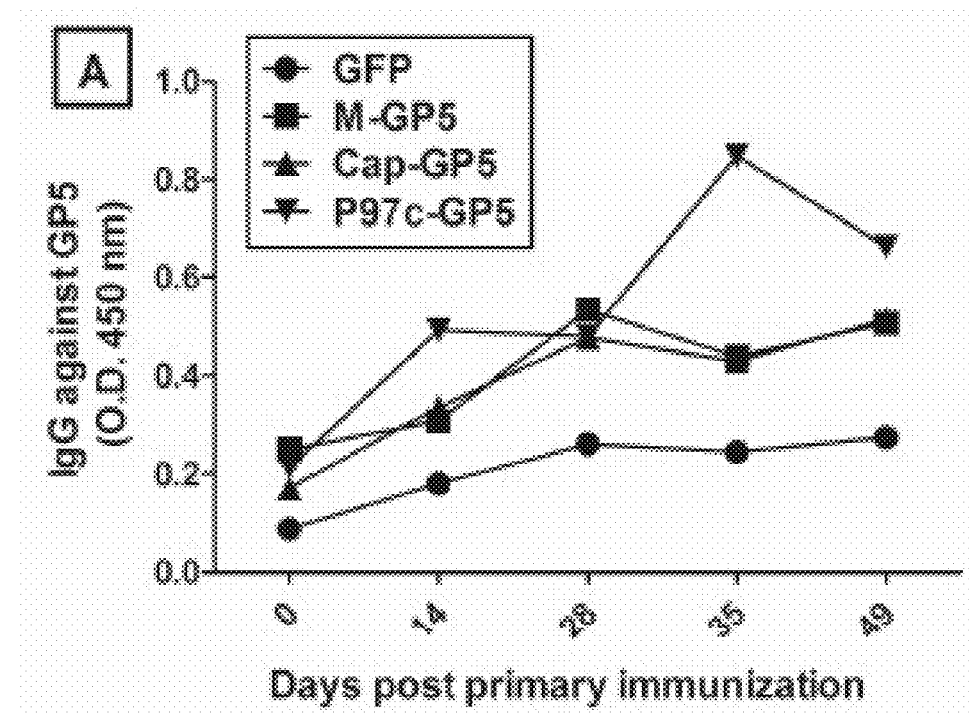
FIGS. 2A to 2C show the antibody responses in sera of mice vaccinated with the recombinant adenoviruses expressing M-GP5, Cap-GP5 or P97c-GP5. IgGs specific to GP5 (FIG. 2A), P97c (FIG. 2B) or Cap (FIG. 2C) were detected in serum samples of mice (n=5 per group) at various time points by indirect ELISA. Data are expressed as mean OD of three independent dard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.
Figure 2B:
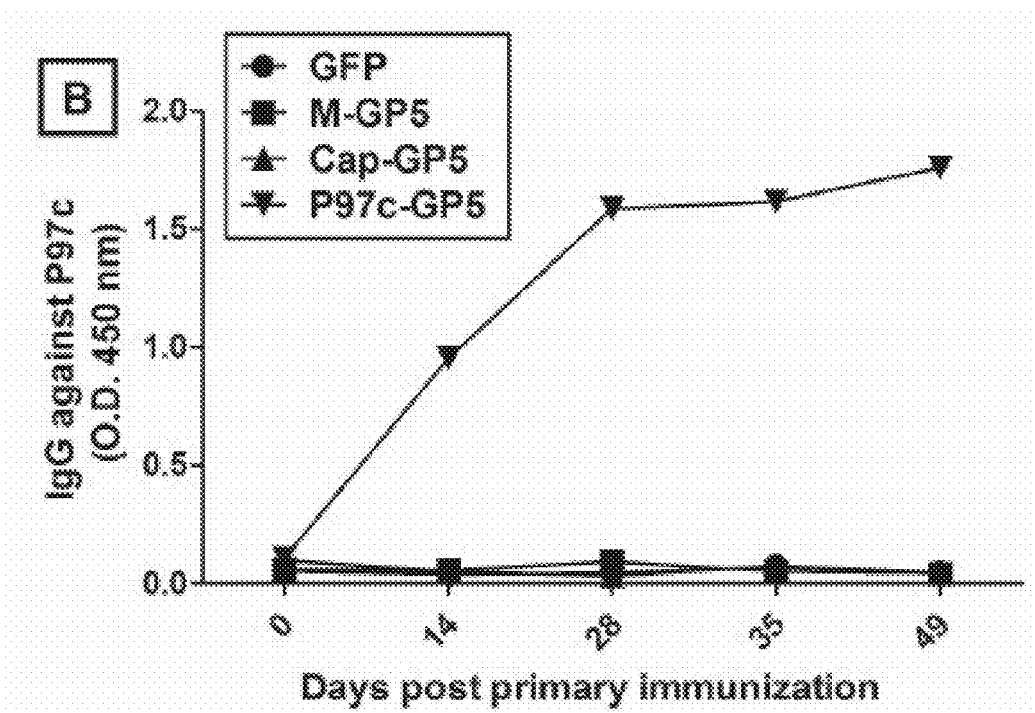
Figure 2C:
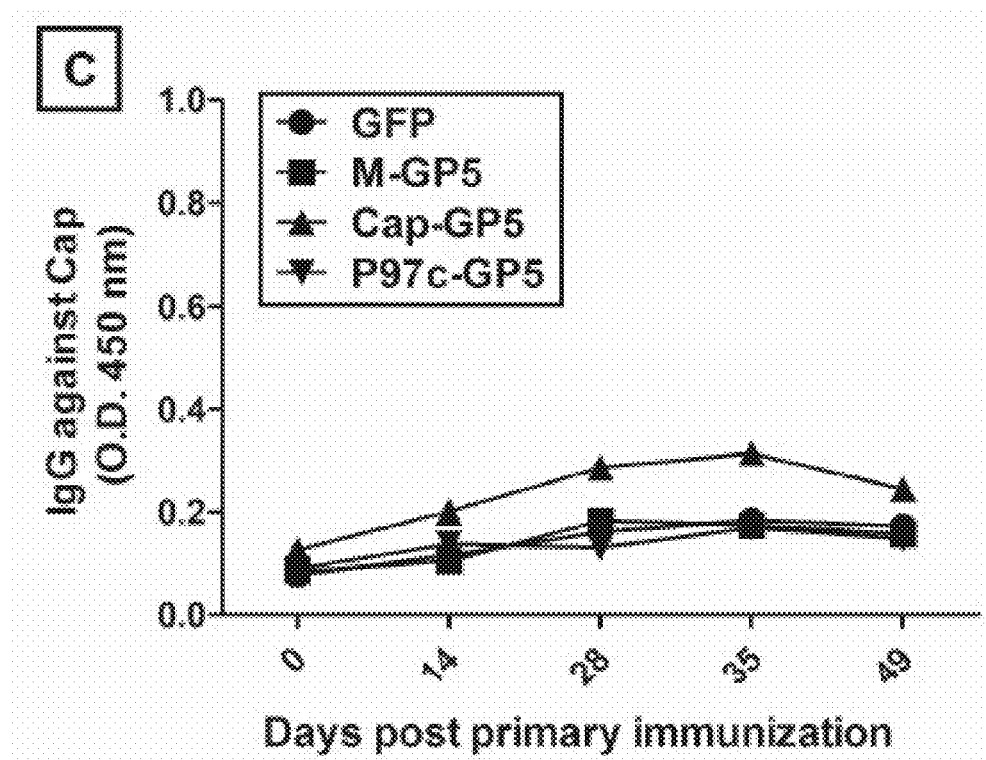

In a first experiment, the ability of AdVs expressing Cap-GP5 or P97c-GP5 fusion proteins to induce GP5-specific Abs in mice was compared to that of AdVs expressing PRRSV M-GP5. The latter group of mice was included because expression of the M-GP5 fusion protein from AdVs induces a higher GP5-specific Ab response when compared to that of GP5 alone (Jiang W et al., *Vet Immunol Immunopathol* 2006; 113(1-2):169-80; Zheng Q, et al. *Virus Genes* 2007; 35(3): 585-95). All groups of mice produced GP5-specific Abs from 14 dpi (FIG. 2A). The highest Ab level was obtained in mice of the P97c-GP5 group at 14, 35 and 49 dpi whereas Ab levels between the M-GP5 and Cap-GP5 groups were similar at any time point of the experiment. No GP5-specific NAbs were detected in any groups of mice. P97c- and Cap-specific Ab responses were also determined in these groups of mice. Anti-P97c Abs were detected at 14 dpi in mice of the P97c-GP5 group with a peak level from 28 dpi (FIG. 2B). Mice of the Cap-GP5 group developed a low level of PCV2 Cap-specific Abs (FIG. 2C) even though PCV2-specific NAbs with a mean titer of 3.4 were detected at 49 dpi in mice of this group.

EXAMPLE 3

Experiment 2

Antibody (Ab) Response Against P97c in Mice Following Immunization

Figure 3A:
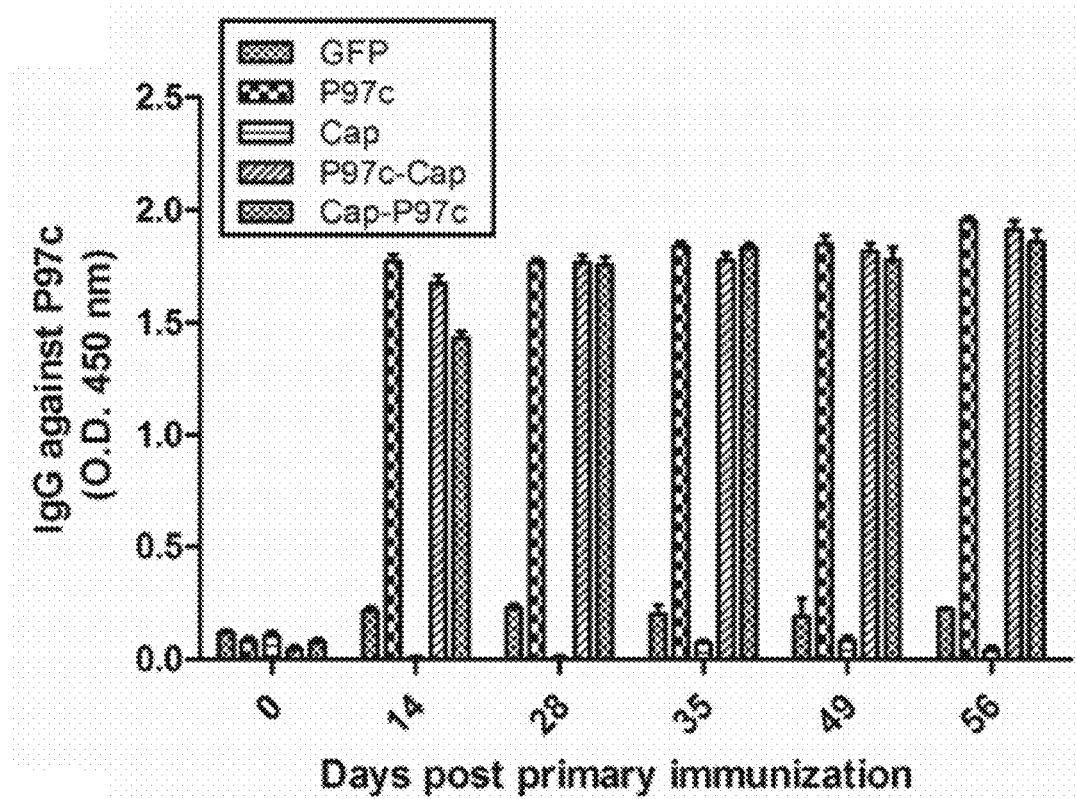
Figure 3B:
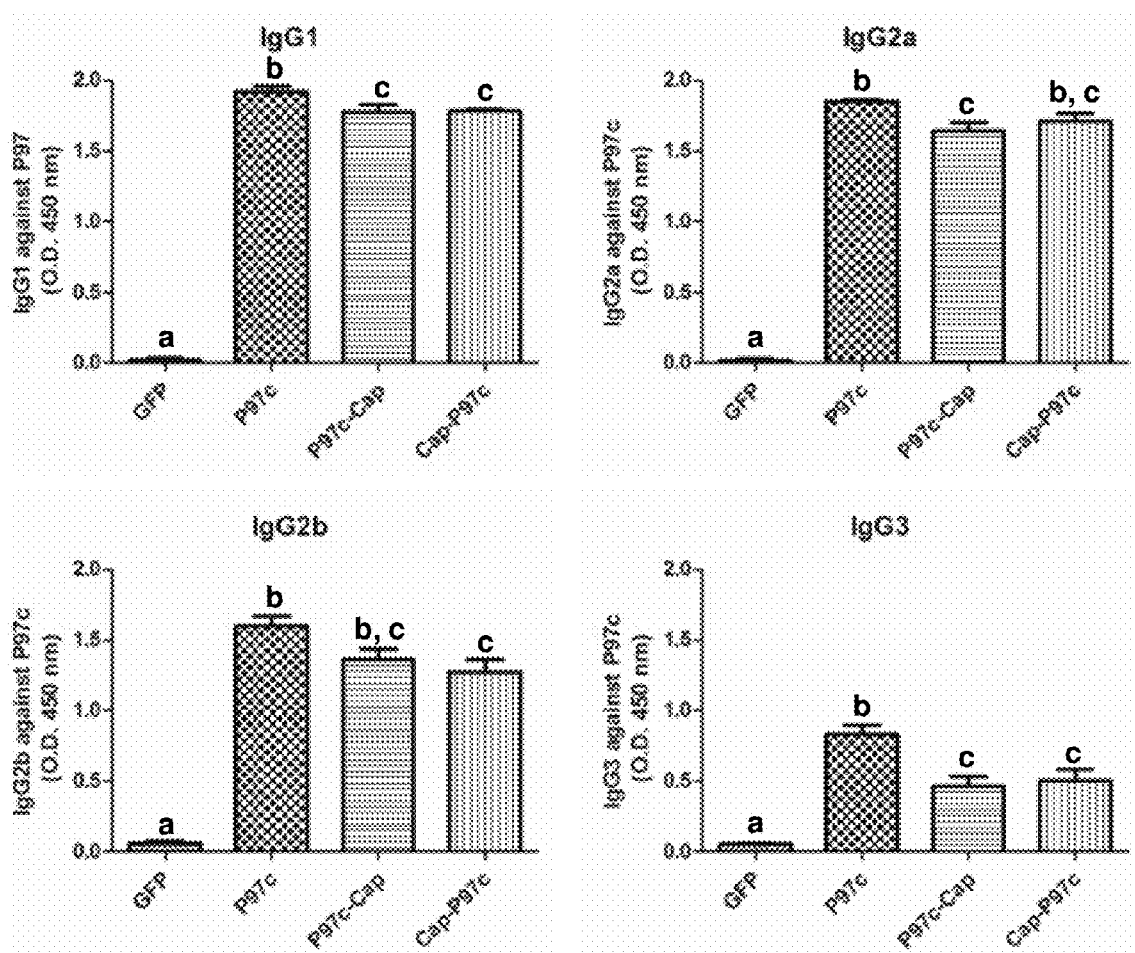

IN a second set of experiments, mice were immunized at days 0 and 14 IM with $10^9$ TCID50 with rAdVs expressing either P97c protein, Cap protein or both proteins in fusion. Specific antibody response was determined by indirect ELISA. As shown in FIG. 3A, all groups that received rAdVs expressing P97c developed a strong antibody response against P97c at 14 dpi. This strong antibody response was maximal for all groups at 14 dpi except for the Cap-P97c group in which the response was maximal at 28 dpi. IgG isotyping was performed at 49 dpi in order to define the immune profile response; IgG1 are preferentially induced when a T helper 2 (Th2)-type response is elicited whereas the presence of IgG2a, IgG2b and IgG3 is indicative of a T helper 1 (Th1)-type response. As shown in FIG. 3B, all immunized groups have developed IgG1, IgG2a, IgG2b and IgG3 against P97c. For all isotypes, there was no significant difference between groups that have received P97c-Cap or Cap-P97c (P>0.05). Groups having received P97c alone have developed a significantly higher IgG1 (P<0.05) and IgG3 (P<0.01) responses than groups who had received P97c in fusion with Cap protein. As for IgG2a, mice from the P97c group have developed a significantly higher antibodies response than those of the P97c-Cap group, and the IgG2b level was significantly higher in mice of the P97c group relative to those of the Cap-P97c group (P<0.05).

Antibody (Ab) Response Against Cap in Mice Following Immunization

Figure 4A:
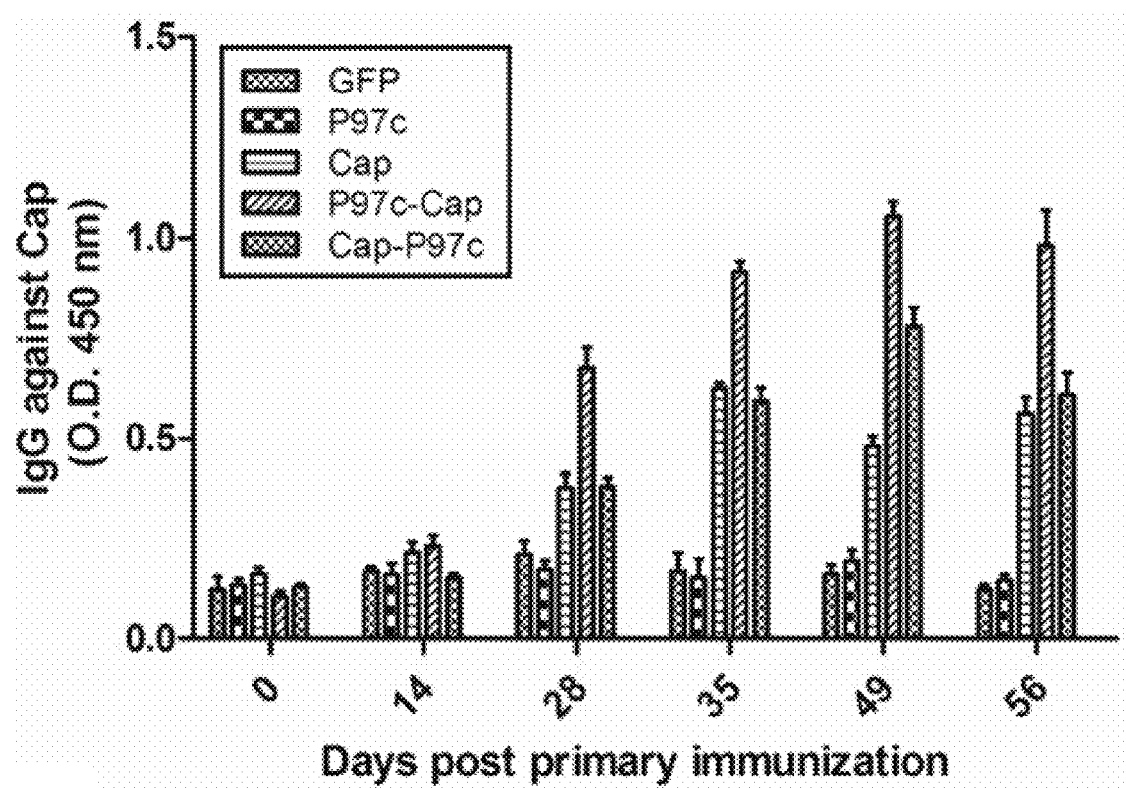
Figure 4B:
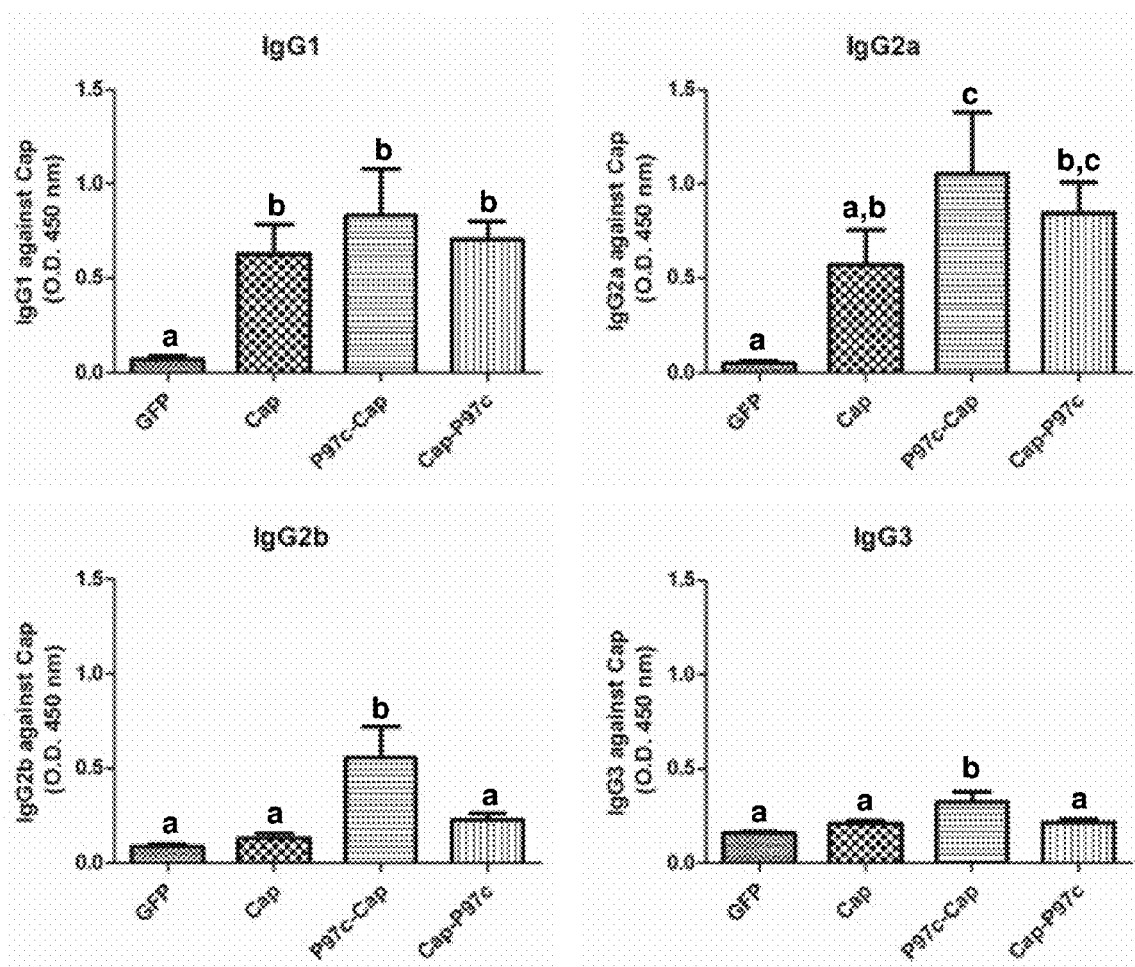

Mice immunized with rAdVs expressing Cap protein developed specific antibody against Cap at 28 dpi. This antibody response was higher with the P97c-Cap group than in Cap or Cap-P97c groups throughout the experiment. At 56 dpi, Cap and Cap-P97c groups developed the same levels of antibody (FIG. 4A). As shown in FIG. 4B, IgG1 specific to Cap protein was not significantly different between the different groups tested. However, mice form the P97c-Cap group developed significant amounts of IgG2b and IgG3.

The PCV2-specific NT was performed to determine the NAb production at 56 dpi. Mice of the Cap-P97c group showed the highest NAb response (P<0.001) with a mean NAb titer of 6.5 (Log 2) as compared to the mean NAb titer of 4.16 (Log 2) from the group of mice given the Cap protein alone (FIG. 5). Only one mouse of the P97c-Cap developed a low level of PCV2-specific NAbs with a resulting mean NAb titer of 0.33 (Log 2).

Thus, fusion of the GP5 or Cap with P97c expressed from rAdVs allowed higher immunogen-specific Ab responses when compared to those obtained in mice immunized with rAdVs expressing each immunogen alone, indicating a P97c-associated immunopotentiation/adjuvant effect.

Although the present invention has been described hereinabove by way of specific embodiments thereof, it can be modified, without departing from the spirit and nature of the subject invention as defined in the appended claims.

---

The invention claimed is:

1. An immunogenic composition comprising a p97 adhesin adjuvant polypeptide comprising a sequence having at least 80% sequence identity with the amino acid sequence of SEQ ID NO: 9 and having adjuvant properties, covalently linked to a heterologous antigen polypeptide.

2. The immunogenic composition of claim 1, wherein the p97 adhesin adjuvant polypeptide comprises the amino acid sequence of SEQ ID NO: 9.

3. The immunogenic composition of claim 1, wherein the heterologous antigen is an antigen from a human pathogen or an antigen of human origin.

4. The immunogenic composition of claim 1, wherein the p97 adhesin adjuvant polypeptide is N-terminal relative to the heterologous antigen polypeptide.

5. The immunogenic composition of claim 1, further comprising one or more pharmaceutically acceptable excipients.

6. A method of inducing an immune response against a heterologous antigen polypeptide in a subject, the method comprising administering to said subject an effective amount of an immunogenic composition comprising a p97 adhesin adjuvant polypeptide comprising a sequence having at least 80% sequence identity with the amino acid sequence of SEQ ID NO: 9 and having adjuvant properties, covalently linked to said heterologous antigen polypeptide.

7. The method of claim 6, wherein the p97 adhesin adjuvant polypeptide comprises the amino acid sequence of SEQ ID NO: 9.

8. The method of claim 6, wherein the heterologous antigen is an antigen from a human pathogen or antigen of human origin, and said subject is a human.

9. The method of claim 6, wherein the p97 adhesin adjuvant polypeptide is N-terminal relative to the heterologous antigen polypeptide.

10. The method of claim 6, wherein the immunogenic composition further comprises one or more pharmaceutically acceptable excipients.

11. The immunogenic composition of claim 1, wherein the p97 adhesin adjuvant polypeptide comprises a sequence having at least 90% sequence identity with the amino acid sequence of SEQ ID NO: 9 and having adjuvant properties.

12. The method of claim 6, wherein the p97 adhesin adjuvant polypeptide comprises a sequence having at least 90% sequence identity with the amino acid sequence of SEQ ID NO: 9 and having adjuvant properties.

* * * * *